United States Patent
Chen et al.

(10) Patent No.: US 11,396,549 B2
(45) Date of Patent: Jul. 26, 2022

(54) ANTI-COLONY STIMULATING FACTOR 1 RECEPTOR (CSF1R) ANTIBODIES AND METHODS OF USE THEREOF FOR TREATING CANCER

(71) Applicant: ELIXIRON IMMUNOTHERAPEUTICS (HONG KONG) LIMITED, Hong Kong (CN)

(72) Inventors: Hung-Kai Chen, Los Altos, CA (US); Daw-Tsun Shih, Taipei (TW); Jing-Yi Huang, Taipei (TW); Huey-Wen Hsiao, Taipei (TW); Chih-Lun Hsiao, Taipei (TW)

(73) Assignee: ELIXIRON IMMUNOTHERAPEUTICS (HONG KONG) LIMITED, Hong Kong (CN)

( * ) Notice: Subject to any disclaimer, the term of this patent is extended or adjusted under 35 U.S.C. 154(b) by 0 days.

(21) Appl. No.: 17/463,427

(22) Filed: Aug. 31, 2021

(65) Prior Publication Data
US 2021/0403583 A1    Dec. 30, 2021

Related U.S. Application Data

(63) Continuation of application No. PCT/US2020/034246, filed on May 22, 2020.

(60) Provisional application No. 62/852,418, filed on May 24, 2019.

(51) Int. Cl.
*C07K 16/28* (2006.01)

(52) U.S. Cl.
CPC ...... *C07K 16/2866* (2013.01); *C07K 2317/24* (2013.01); *C07K 2317/33* (2013.01); *C07K 2317/732* (2013.01); *C07K 2317/76* (2013.01); *C07K 2317/92* (2013.01)

(58) Field of Classification Search
CPC .......... C07K 16/2866; C07K 2317/732; C07K 2317/76
See application file for complete search history.

(56) References Cited

U.S. PATENT DOCUMENTS

| | | |
|---|---|---|
| 2008/0124330 A1 | 5/2008 | Nakano et al. |
| 2009/0297439 A1 | 3/2009 | Comoglio et al. |
| 2011/0178278 A1 | 7/2011 | Haegel et al. |
| 2011/0223107 A1 | 9/2011 | Tremblay et al. |
| 2013/0243795 A1 | 9/2013 | Chen et al. |
| 2016/0185869 A1 | 6/2016 | Sikorski et al. |
| 2017/0334999 A1 | 11/2017 | Sathyanarayanan et al. |
| 2018/0334496 A1 | 11/2018 | Perlroth et al. |

FOREIGN PATENT DOCUMENTS

WO    2018002952 A    1/2018

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Cannarile et al., "Colony-stimulating factor 1 receptor (CSF1R) inhibitors in cancer therapy." J. Immunother. Cancer. 2017, vol. 5:53.
PCT/US20/34246, "International Search Report" and "Written Opinion of the International Searching Authority" dated Oct. 21, 2020.

* cited by examiner

*Primary Examiner* — Robert S Landsman
(74) *Attorney, Agent, or Firm* — FisherBroyles, LLP; Adam K. Whiting

(57) ABSTRACT

The present disclosure provides antibodies, including antibody fusions, which specifically bind to human CSF1 receptor protein (huCSF1R) and are capable of decreasing, inhibiting, and/or fully-blocking immune regulatory effects mediated by huCSF1R, such as regulation of TAMs in the tumor microenvironment. Additionally, the antibodies include fusions with the cytokine inhibitory factor, IL10, which can replenish and/or activate CD8+ T-cell cytotoxicity in the tumor microenvironment. The present disclosure also provides methods of using the antibodies (and compositions thereof) to treat diseases and conditions responsive to decreasing, inhibiting and/or blocking immune regulatory function or activity mediated by CSF1 binding to CSF1R.

19 Claims, 31 Drawing Sheets

Specification includes a Sequence Listing.

293F/ human CSF1R

293F/ cyno CSF1R

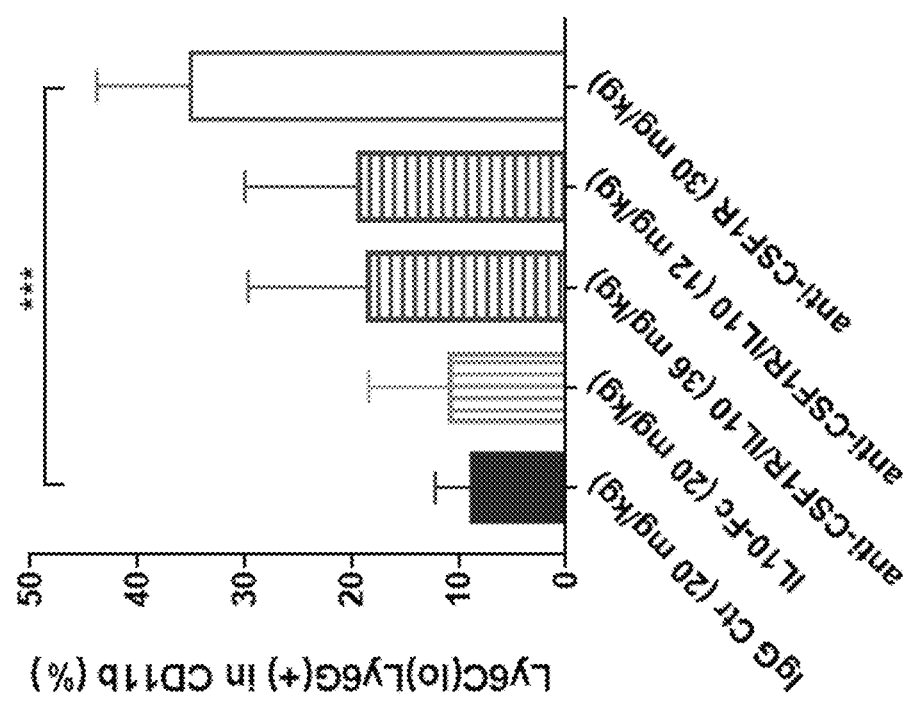

ANTI-COLONY STIMULATING FACTOR 1 RECEPTOR (CSF1R) ANTIBODIES AND METHODS OF USE THEREOF FOR TREATING CANCER

CROSS REFERENCE TO RELATED APPLICATIONS

This application is a continuation of International Application No. PCT/US2020/034246, filed May 22, 2020, which claims priority of U.S. Provisional Patent Application Ser. No. 62/852,418, filed on May 24, 2019, the entirety of which is incorporated herein by reference.

FIELD OF THE INVENTION

The present disclosure relates to antibodies and fusion proteins which bind to the CSF1R receptor and methods of using such antibodies and fusion proteins.

REFERENCE TO SEQUENCE LISTING

The official copy of the Sequence Listing is submitted concurrently with the specification as an ASCII formatted text file via EFS-Web, with a file name of "09793-003WO1_SeqList_ST25.txt", a creation date of May 21, 2020, and a size of 136,762 bytes. The Sequence Listing filed via EFS-Web is part of the specification and is incorporated in its entirety by reference herein.

BACKGROUND OF THE INVENTION

Colony stimulating factor 1 receptor or "CSF1R" (also known in the art as CD115, C-FMS, CSF-1R, CSFR, FIM2, FMS, HDLS, M-CSFR, M-CSF-R, or BANDDOS) is a cell-surface protein encoded, in humans, by the CSF1R gene (also known as "c-FMS"). CSF1R is a single pass type I membrane protein of 972 amino acid that acts as the receptor for colony stimulating factor 1 ("CSF1"), a cytokine which controls the production, differentiation, and function of macrophages. CSF1R is believed to mediate most, if not all, of the biological effects of CSF1 cytokine. CSF1R is a tyrosine-protein kinase, and binding of CSF1 activates it to undergo oligomerization and trans-phosphorylation.

CSF1R has been found to be overexpressed in many cancers and on tumor-associated macrophages (TAMs). Binding of CSF1 to CSF1R has been found to regulate the survival of TAMs, which can promote an immunosuppressive tumor microenvironment. Accordingly, inhibitors of CSF1R have been studied as possible treatments for cancer or inflammatory diseases. A number of small molecule and antibody inhibitors of CSF1R have entered clinical trials including: Pexidartinib, PLX7486, ARRY-382, JNJ-40346527, BLZ945, Emactuzumab, Cabiralizumab, AMG820, IMC-CS4.

Interleukin 10 or "IL10" (also known as human cytokine synthesis inhibitory factor, CSIF, IL-10, IL10A, GVHDS, or TGIF) is an anti-inflammatory cytokine. The human IL10 protein is a homodimer of two 178 amino acid subunits. IL10 signals through a receptor complex consisting of two IL10 receptor-1 and two IL10 receptor-2 proteins. Consequently, the functional receptor consists of four IL10 receptor molecules. IL10 binding induces STAT3 signaling via the phosphorylation of the cytoplasmic tails of IL10 receptor 1+IL10 receptor 2 by JAK1 and Tyk2, respectively. IL10 is primarily produced by monocytes and, to a lesser extent, lymphocytes, namely type-II T helper cells ($T_H2$), mast cells, $CD4^+CD25^+Foxp3^+$ regulatory T cells, and in a certain subset of activated T cells and B cells. IL10 can be produced by monocytes upon PD-1 triggering.

IL10 is known to have multiple effects in immunoregulation and inflammation. IL10 is known to downregulate the expression of Th1 cytokines, MHC class II antigens, and co-stimulatory molecules on macrophages. IL10 is also known to enhance B cell survival, proliferation, and antibody production. IL10 can block NF-κB activity, and is involved in the regulation of the JAK-STAT signaling pathway. IL10 is capable of inhibiting synthesis of pro-inflammatory cytokines such as IFN-γ, IL-2, IL-3, TNFα and GM-CSF made by cells such as macrophages and Th1 T cells. It also displays a potent ability to suppress the antigen-presentation capacity of antigen presenting cells; however, it is also stimulatory towards certain T cells (Th2) and mast cells and stimulates B cell maturation and antibody production.

IL10 has been recognized as a potential inhibitor of tumor metastasis and immunostimulatory agent useful in immuno-oncology treatments. In transgenic mice expression of IL10 or dosing with IL10 have been observed to control of primary tumor growth and decrease metastatic burden. A PEGylated version of recombinant murine IL10 has been shown to induce IFNγ and CD8+ T cell dependent anti-tumor immunity in mouse models. PEGylated recombinant human IL10 has been shown to enhance CD8+ T cell secretion of the cytotoxic molecules Granzyme B and Perforin and potentiate T cell receptor dependent IFNγ secretion. In clinical trials the PEGylated recombinant human IL10 (PEG-rHuIL-10, AM0010) has been found to exhibit substantial anti-tumor efficacy, eliciting a dose titratable induction of the immune stimulatory cytokines IFNγ, IL-18, IL-7, GM-CSF and IL-4. Treated patients also exhibited an increase of peripheral CD8+ T cells expressing markers of activation, such as PD1, lymphocyte activation gene 3 (LAG3)+ and increased Fas Ligand (FasL), and a decrease in serum TGFβ. These findings suggest that IL10 treatment results in a predominantly immunostimulatory effect in humans.

SUMMARY OF THE INVENTION

The present disclosure provides anti-CSF1R antibodies that specifically bind human CSF1R with high affinity. The antibodies are capable of decreasing, inhibiting, and/or fully-blocking immune regulatory effects mediated by CSF1R, including binding of CSF1. The present disclosure also provides fusions of an anti-CSF1R antibody with one or two IL10 polypeptides.

These anti-CSF1R/IL10 fusion proteins of the present disclosure are capable of providing a combined therapeutic effect of blocking immune regulatory effects mediated by CSF1R and providing immunostimulatory effects mediated by IL10.

In at least one embodiment, the present disclosure provides an anti-CSF1R antibody comprising (i) a first light chain complementary determining region (CDR-L1), a second light chain complementary determining region (CDR-L2), and a third light chain complementary determining region (CDR-L3), and/or (ii) a first heavy chain complementary determining region (CDR-H1), a second heavy chain complementary determining region (CDR-H2), and a third heavy chain complementary determining region (CDR-H3), wherein:

(a) CDR-H1 comprises an amino acid sequence selected from SEQ ID NO: 3, 4, 28, or 29;

(b) CDR-H2 comprises an amino acid sequence selected from SEQ ID NO: 6, 7, 31, or 32;
(c) CDR-H3 comprises an amino acid sequence selected from SEQ ID NO: 8, 9, 33, or 34;
(d) CDR-L1 comprises an amino acid sequence selected from SEQ ID NO: 13, 14, 37, or 38;
(e) CDR-L2 comprises an amino acid sequence selected from KAS, VAS, or SEQ ID NO: 15, or 39;
(f) CDR-L3 comprises an amino acid sequence selected from SEQ ID NO: 16, 17, 40, or 41.

In at least one embodiment, the present disclosure provides an anti-CSF1R antibody wherein:
(a) CDR-H1 comprises the amino acid sequence of SEQ ID NO: 3 or 4, CDR-H2 comprises the amino acid sequence of SEQ ID NO: 6 or 7, and CDR-H3 comprises the amino acid sequence of SEQ ID NO: 8 or 9; or
(b) CDR-H1 comprises the amino acid sequence of SEQ ID NO: 28 or 29, CDR-H2 comprises the amino acid sequence of SEQ ID NO: 31 or 32, and CDR-H3 comprises the amino acid sequence of SEQ ID NO: 33 or 34.

In at least one embodiment, the present disclosure provides an anti-CSF1R antibody wherein:
(a) CDR-L1 comprises the amino acid sequence of SEQ ID NO: 13 or 14, CDR-L2 comprises the amino acid sequence of KAS, or SEQ ID NO: 15, and CDR-L3 comprises the amino acid sequence of SEQ ID NO: 16 or 17; or
(b) CDR-L1 comprises the amino acid sequence of SEQ ID NO: 37 or 38, CDR-L2 comprises the amino acid sequence of VAS or SEQ ID NO: 39, and CDR-L3 comprises the amino acid sequence of SEQ ID NO: 40 or 41.

In at least one embodiment, the present disclosure provides an anti-CSF1R antibody wherein:
(a) CDR-H1 comprises the amino acid sequence of SEQ ID NO: 3, CDR-H2 comprises the amino acid sequence of SEQ ID NO: 6, CDR-H3 comprises the amino acid sequence of SEQ ID NO: 8, CDR-L1 comprises the amino acid sequence of SEQ ID NO: 13, CDR-L2 comprises the amino acid sequence of KAS, and CDR-L3 comprises the amino acid sequence of SEQ ID NO: 16;
(b) CDR-H1 comprises the amino acid sequence of SEQ ID NO: 28, CDR-H2 comprises the amino acid sequence of SEQ ID NO: 31, CDR-H3 comprises the amino acid sequence of SEQ ID NO: 33, CDR-L1 comprises the amino acid sequence of SEQ ID NO: 37, CDR-L2 comprises the amino acid sequence of VAS, and CDR-L3 comprises the amino acid sequence of SEQ ID NO: 40; (c) CDR-H1 comprises the amino acid sequence of SEQ ID NO: 4, CDR-H2 comprises the amino acid sequence of SEQ ID NO: 7, CDR-H3 comprises the amino acid sequence of SEQ ID NO: 9, CDR-L1 comprises the amino acid sequence of SEQ ID NO: 14, CDR-L2 comprises the amino acid sequence of SEQ ID NO: 15, and CDR-L3 comprises the amino acid sequence of SEQ ID NO: 17; (d) CDR-H1 comprises the amino acid sequence of SEQ ID NO: 29, CDR-H2 comprises the amino acid sequence of SEQ ID NO: 32, CDR-H3 comprises the amino acid sequence of SEQ ID NO: 34, CDR-L1 comprises the amino acid sequence of SEQ ID NO: 38, CDR-L2 comprises the amino acid sequence of VAS or SEQ ID NO: 39, and CDR-L3 comprises the amino acid sequence of SEQ ID NO: 41.

In at least one embodiment, the present disclosure provides an anti-CSF1R antibody wherein the antibody comprises a heavy chain variable domain ($V_H$) amino acid sequence having at least 90% identity to a sequence selected from SEQ ID NO: 2, 19, 23, 27, 43, or 47; and/or a light chain variable domain ($V_L$) amino acid sequence having at least 90% identity to a sequence selected from SEQ ID NO: 12, 21, 25, 36, 45, or 49; optionally, wherein:
(a) the antibody comprises a $V_H$ amino acid sequence having at least 90% identity to SEQ ID NO: 2; and/or a light chain variable domain ($V_L$) amino acid sequence having at least 90% identity to SEQ ID NO: 12;
(b) the antibody comprises a $V_H$ amino acid sequence having at least 90% identity to SEQ ID NO: 19; and/or a $V_L$ amino acid sequence having at least 90% identity to SEQ ID NO: 21;
(c) the antibody comprises a $V_H$ amino acid sequence having at least 90% identity to SEQ ID NO: 23; and/or a $V_L$ amino acid sequence having at least 90% identity to SEQ ID NO: 25;
(d) the antibody comprises a $V_H$ amino acid sequence having at least 90% identity to SEQ ID NO: 27; and/or a $V_L$ amino acid sequence having at least 90% identity to SEQ ID NO: 36;
(e) the antibody comprises a $V_H$ amino acid sequence having at least 90% identity to SEQ ID NO: 43; and/or a $V_L$ amino acid sequence having at least 90% identity to SEQ ID NO: 45; or
(f) the antibody comprises a $V_H$ amino acid sequence having at least 90% identity to SEQ ID NO: 47; and/or a $V_L$ amino acid sequence having at least 90% identity to SEQ ID NO: 49.

In at least one embodiment, the present disclosure provides an anti-CSF1R antibody wherein the antibody comprises a heavy chain (HC) amino acid sequence having at least 90% identity to a sequence selected from SEQ ID NO: 58, 60, 62, 64, 66, or 68, and/or a light chain (LC) amino acid sequence having at least 90% identity to a sequence selected from SEQ ID NO: 59, 61, 63, 65, 67, or 69; optionally, wherein the antibody comprises:
(a) the HC amino acid sequence of SEQ ID NO: 58, and the LC amino acid sequence of SEQ ID NO: 59;
(b) the HC amino acid sequence of SEQ ID NO: 60, and LC amino acid sequence of SEQ ID NO: 61;
(c) the HC amino acid sequence of SEQ ID NO: 62, and the LC amino acid sequence of SEQ ID NO: 63;
(d) the HC amino acid sequence of SEQ ID NO: 64, and the LC amino acid sequence of SEQ ID NO: 65;
(e) the HC amino acid sequence of SEQ ID NO: 66, and the LC amino acid sequence of SEQ ID NO: 67; or
(f) the HC amino acid sequence of SEQ ID NO: 68, and the LC amino acid sequence of SEQ ID NO: 69.

In at least one embodiment, the present disclosure provides an anti-CSF1R antibody wherein the antibody comprises a HC fused via a linker to an IL10 polypeptide; optionally, wherein:
(a) the linker comprises an amino acid sequence of SEQ ID NO: 78;
(b) the IL10 polypeptide comprises one, two, or four IL10 polypeptides; and/or
(c) the IL10 polypeptide comprises an amino acid sequence of SEQ ID NO: 75;
(d) the HC comprises an amino acid sequence having at least 90% identity to a sequence selected from SEQ ID NO: 50, 51, 52, 53, 54, 55, 56, or 57.

In at least one embodiment, the present disclosure provides an anti-CSF1R antibody wherein the antibody comprises a comprises a heavy chain (HC) amino acid sequence having at least 90% identity to a sequence selected from SEQ ID NO: 50, 51, 52, 53, 54, 55, 56, or 57, and a light chain (LC) amino acid sequence having at least 90% identity to a sequence selected from SEQ ID NO: 59, 61, 63, 65, 67, or 69; optionally, wherein the antibody comprises:

(a) the HC amino acid sequence of SEQ ID NO: 50, and the LC amino acid sequence of SEQ ID NO: 59;

(b) the HC amino acid sequence of SEQ ID NO: 51, and the LC amino acid sequence of SEQ ID NO: 59;

(c) the HC amino acid sequence of SEQ ID NO: 52, and LC amino acid sequence of SEQ ID NO: 61;

(d) the HC amino acid sequence of SEQ ID NO: 53, and the LC amino acid sequence of SEQ ID NO: 63;

(e) the HC amino acid sequence of SEQ ID NO: 54, and the LC amino acid sequence of SEQ ID NO: 65;

(f) the HC amino acid sequence of SEQ ID NO: 55, and the LC amino acid sequence of SEQ ID NO: 65;

(g) the HC amino acid sequence of SEQ ID NO: 56, and the LC amino acid sequence of SEQ ID NO: 67; or (h) the HC amino acid sequence of SEQ ID NO: 57, and the LC amino acid sequence of SEQ ID NO: 69.

In at least one embodiment, the present disclosure provides an anti-CSF1R antibody wherein:

(a) the antibody binds to human CSF1R with a binding affinity of $1\times10^{-8}$M or less, $1\times10^{-9}$ M or less, $1\times10^{-10}$ M or less; optionally, wherein the binding affinity is measured by equilibrium dissociation constant ($K_D$) to a huCSF1R polypeptide of SEQ ID NO: 70;

(b) the antibody binds to cynomolgus CSF1R with a binding affinity of $1\times10^{-8}$M or less, $1\times10^{-9}$ M or less, $1\times10^{-10}$ M or less; optionally, wherein the binding affinity is measured by equilibrium dissociation constant ($K_D$) to a cynoCSF1R polypeptide of SEQ ID NO: 71;

(c) the antibody decreases CSF1-induced and IL34-induced phosphorylation of huCSF1R or AKT;

(d) the antibody inhibits CSF1-dependent and IL34-induced cell proliferation by at least 65%, at least 75%, at least 85%, at least 95%, or at least 100%; optionally, wherein at a CSF1 concentration of 20 ng/mL or a IL34 concentration of 33 ng/mL the antibody has an $IC_{50}$ of 5 nM or less, 1 nM or less, 0.5 nM or less, or 0.1 nM or less;

(e) the antibody inhibits CSF1-dependent dependent survival of human CD14+ monocytes or monocyte-derived macrophages by at least 65%, at least 75%, at least 85%, at least 95%, or at least 100%; optionally, wherein at a CSF1 concentration of 100 ng/mL the antibody has an $IC_{50}$ of 5 nM or less, 1 nM or less, 0.5 nM or less, or 0.1 nM or less;

(f) the antibody increases NK-cell mediated ADCC against CSF1R expressing 293F cells by at least 10%; at least 20%, or at least 25%;

(g) the antibody decreases tumor volume in a syngeneic mouse tumor model measured at 21 days by at least 25%, at least 50%, at least 75%, or more, wherein the mouse tumor model is selected from: CT26 CRC, EMT6 TNBC, MC38 CRC, Renca RCC, LL/2 lung, Pan02 PDAC, H22 HCC, Q1 HNSCC;

(h) the antibody increases blood levels of CSF1 and IL34 in a CT26 colon tumor syngeneic mouse model by at least 50-fold, at least 100-fold, at 200-fold, or at least 500-fold;

(i) the antibody decreases TAM population in in a CT26 colon tumor syngeneic mouse model by at least 20%, at least 30%, at least 40%, at least 50%, at least 60%, or more; optionally, wherein the MDSC population is reduced less than 10%, less than 5%, or less;

(j) the antibody increases MC/9 cell proliferation by at least 25%, at least 50%, at least 100%, at least 150%, at least 200% or more;

(k) the antibody increases IFNγ and granzyme B production from activated CD8 T cells by at least 25%, at least 50%, at least 100%, or more; and/or (l) the antibody increases CD8+LAG3+PD1+ T cell blood levels in a CT26 colon tumor syngeneic mouse model by at least 2-fold, at least 4-fold, at least 6-fold, at least 8-fold, at least 10-fold, or more.

The present disclosure also provides embodiments of the anti-CSFR1 antibodies disclosed herein, including embodiments wherein: (i) the antibody is a human, humanized, or chimeric antibody; (ii) the antibody comprises a fusion to recombinant protein; optionally, a fusion to an IL10 polypeptide; (iii) the antibody is a full length antibody of class IgG, optionally, wherein the class IgG antibody has an isotype selected from IgG1, IgG2, IgG3, and IgG4; (iv) the antibody comprises an Fc region variant, optionally an Fc region variant that alters effector function and/or a variant that alters antibody half-life; (v) the antibody is an antibody fragment, optionally selected from the group consisting of F(ab')$_2$, Fab', Fab, Fv, single domain antibody (VHH), and scFv; (vi) the antibody comprises an immunoconjugate, optionally, wherein the immunoconjugate comprises a therapeutic agent for treatment of a CSF1R-mediated disease or condition; or (vii) the antibody is a multi-specific antibody, optionally a bispecific antibody.

In at least one embodiment the present disclosure provides an isolated polynucleotide or vector encoding an anti-CSF1R antibody of the present disclosure. In at least one embodiment the present disclosure provides an isolated host cell comprising a polynucleotide or vector encoding an anti-CSF1R antibody of the present disclosure. In at least one embodiment, the present disclosure also provides a method of producing an anti-CSFR1 antibody of present disclosure comprising culturing a host cell comprising a polynucleotide or vector encoding an anti-CSF1R antibody so that an antibody is produced.

In at least one embodiment, the present disclosure provides a pharmaceutical composition comprising an anti-CSF1R antibody of the present disclosure and a pharmaceutically acceptable carrier; optionally, wherein the composition further comprises an IL10 polypeptide, a chemotherapeutic agent, and/or an antibody comprising a specificity for an immune checkpoint molecule.

In at least one embodiment, the present disclosure provides a method of treating a CSF1R-mediated disease in a subject, the method comprising administering to the subject a therapeutically effective amount of an anti-CSF1R antibody of the present disclosure, or administering to the subject a therapeutically effective amount of a pharmaceutical composition of the present disclosure; optionally, wherein the disease is cancer; optionally, wherein the cancer is selected from colon cancer, pancreatic cancer, ovarian cancer, HCC, renal cancer, breast cancer, lung cancer, gastric cancer, head and neck cancer, and oral cancer.

In at least one embodiment, the present disclosure provides a method for treating cancer in a subject, comprising administering to the subject a CSF1R antagonist and an IL-10 agonist; optionally, wherein the CSF1R antagonist comprises an anti-CSF1R antibody, a shRNA, a siRNA, a miRNA, a small molecule inhibitor of CSF1R, or a combination thereof; optionally, wherein the IL-10 agonist is IL-10, an IL-10 receptor binding protein, or a combination thereof; optionally, wherein the CSF1R antagonist is an anti-CSF1R antibody of the present disclosure; optionally, wherein the CSF1R antagonist and the IL10 agonist comprise an anti-CSF1R antibody having a HC fused via a linker to an IL10 polypeptide; optionally, wherein the method further comprises administering to the subject a T cell therapy.

BRIEF DESCRIPTION OF THE FIGURES

FIG. 1A shows results of competition with $1^{st}$ mAb hy6M6 and $2^{nd}$ mAb hy6D4. FIG. 1B shows results of competition with $1^{st}$ mAb hy6M6 and $2^{nd}$ mAb hy6M6.

FIG. 2A: binding of 6D4, 6M6, or control human IgG (hIgG) to AML-5 human acute myeloid leukemia cells; FIG. 2B: binding of 6D4, 6M6, and hIgG to 293F cells overexpressed with human CSF1R; and FIG. 2C: binding of 6D4, 6M6, and hIgG to 293F cells overexpressed with cynomolgus CSF1R.

FIG. 7A: Tumor volumes of Balb/c mice implanted with CT26 at day 28 endpoint. FIG. 7B: Individual tumor volumes over time of Balb/c mice implanted with CT26 at day 0. n=8 mice per group.

FIG. 10A shows SDS-PAGE images of IL10-Fc and $(IL10)_2$-Fc; FIG. 10B shows SDS-PAGE images of 6D4/IL10, 6D4/$(IL10)_2$, 6M6/IL10, and 6M6/$(IL10)_2$ fusion protein preparations; FIG. 10C shows SDS-PAGE images of surrogate anti-mouse-CSF1R antibody, "AB98", and an AB98/IL10 fusion protein. Labels at bottom of gel lanes: N: non-reducing, R: reducing.

FIG. 13A: AML5 cells incubated with CSF1 with humanized anti-CSF1R/IL10 fusion proteins for 3 days. FIG. 13B: Human CD14+ blood monocytes incubated with CSF1 with different concentrations of control hIgG, anti-CSF1R, or anti-CSF1R/IL10 fusion proteins for 6 days. FIG. 13C: Human monocyte-derived macrophages incubated with CSF1 with different concentrations of humanized anti-CSF1R/IL10 fusion proteins for 3 days. FIG. 13D: M-NFS-60 cells incubated with CSF1 with surrogate anti-CSF1R/IL10 fusion proteins for 3 days. Cell survival and proliferation were measured by CellTiter-Glo assay.

FIG. 17A, FIG. 17B, and FIG. 17C depict plots showing results of tumor-infiltrated immune cell analysis in CT26 syngeneic tumor model. Syngeneic CT26 tumors were treated with isotype control, IL10-Fc, surrogate anti-CSF1R or anti-CSF1R/IL10. After 7-day treatment, tumors were harvested and analyzed by flow cytometry. The percentage of CD11b+(FIG. 17A), TAMs (CD11b+F4/80+) (FIG. 17B), granulocytic MDSCs (CD11b+Ly6G+) (FIG. 17C), in the tumor microenvironment were gated on CD45+ leukocytes. n=6 mice per group. Mean±SD is shown. *$p<0.05$, $p<0.01$, *$p<0.001$.

DETAILED DESCRIPTION

Figure 1A:
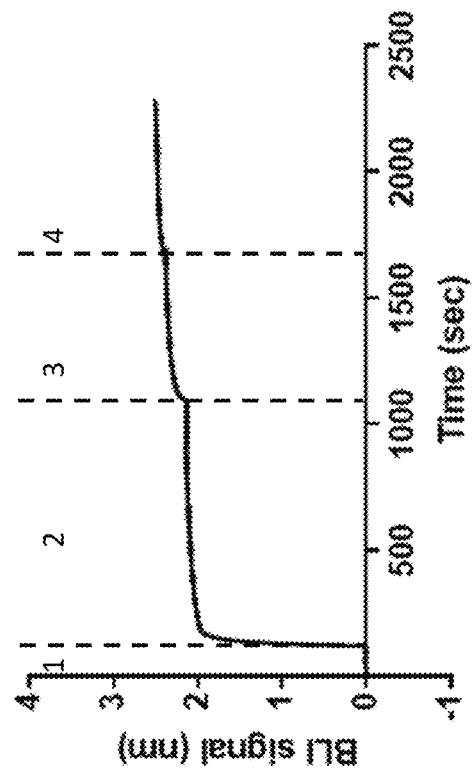
FIG. 1A and FIG. 1B depict results of ForteBio epitope binning assays showing that the two anti-CSF1R antibodies purified from hybridoma supernatant, "hy6D4," and "hy6M6," bind to different epitopes of CSF1R. Sensors went through multiple assay steps (indicated by numbers and divided by dotted lines) including step 1. baseline; step 2. biotin-CSF1R antigen capture; step 3. saturation with $1^{st}$ mAb; and step 4.

The present disclosure provides antibodies, including humanized antibodies, that specifically bind CSF1R with high affinity and thereby inhibit, decrease, and/or fully block the function of CSF1R as a cell surface receptor involved in immune regulation, particularly the function of CSF1R in regulating the survival and maintenance of tumor-associated macrophages (TAMs). TAMs are a major cellular component of tumor microenvironment (TME), and contribute significantly to tumor growth and progression. It is believed that inhibition of CSF1R signaling can deplete TAMs and thereby potentiate an anti-tumor T-cell response. In clinical trials, CSF1R inhibitors have shown limited anti-tumor effects in patients when administered as sole agents, suggesting the need for a combined use of these inhibitors with other anti-tumor therapeutic approaches. IL10 is a cytokine with anti-inflammatory and CD8+ T-cell activation properties. A strong IL-10 signal can promote tumor-specific CD8+ T-cell proliferation, revitalize exhausted T-cells, and thereby increase T-cell cytotoxicity. The present disclosure contemplates the use of anti-CSF1R antibodies in combination with IL10 agonist, including as an anti-CSF1R antibody fusion with IL10 polypeptide. As disclosed herein, the combination CSF1R inhibition to reduce immunosuppressive TAMs and a concentrated IL10 dose to enhance CD8+ T-cell cytotoxicity in the TME can provide an improved therapeutic approach to cancer treatment.

Accordingly, it is contemplated that any of the compositions or formulations comprising an anti-CSF1R antibody of the present disclosure (including anti-CSF1R antibodies fused to IL10 polypeptides) can be used as therapeutics for treatment of diseases mediated by the function of CSF1R or its target antigen, CSF1, such as cancer. Further, it is contemplated that the anti-CSF1R antibody of the present disclosure can be used as a therapeutic in combination with other therapeutics, such as antibodies that activate CD8+ T-cells, and/or target immune checkpoint molecules including, but not limited to, PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning-A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic*, Z. An, ed., J. Wiley & Sons, Hoboken, N.J. (2009); and *Phage Display*, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for the purpose of describing particular embodiments only and is not intended to be limiting. For purposes of interpreting this disclosure, the following description of terms will apply and, where appropriate, a term used in the singular form will also include the plural form and vice versa.

"CSF1R," as used herein, refers to the colony stimulating factor 1 receptor protein, and as used herein encompasses the CSF1R proteins of human, cynomolgus monkey, mouse, and any isoforms of these proteins Amino acid sequences of various exemplary CSF1R proteins are known in the art and are provided in Table 1 below and the attached Sequence Listing.

"CSF1R mediated condition" or "CSF1R mediated disease," as used herein, encompasses any medical condition associated with the specific binding of CSF1 to the cell surface receptor CSF1R. For example, specific binding of CSF1 to CSF1R acts to regulate the survival of TAMs in the tumor microenvironment. Accordingly, CSF1R mediated diseases can include, but are not limited to, any disease or condition mediated by and/or responsive to antagonists or inhibitors of CSF1R, and/or CSF1, including but not limited to cancers.

"IL10" or "IL-10," as used herein, refers to the anti-inflammatory cytokine, interleukin 10, also known as cytokine synthesis inhibitory factor (CSIF) Amino acid sequences of various exemplary IL10 polypeptides and recombinant IL10 fusion constructs are known in the art and are provided in Table 2 below and the attached Sequence Listing.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, antibody fusions (e.g., fusion proteins), multispecific antibodies (e.g., bispecific antibodies), monovalent antibodies (e.g., single-arm antibodies), multivalent antibodies, antigen-binding fragments (e.g., Fab', F(ab')$_2$, Fab, Fv, rIgG, and scFv fragments), and synthetic antibodies (or antibody mimetics).

"Anti-CSF1R antibody" or "antibody that binds CSF1R" refers to an antibody that binds CSF1R with sufficient affinity such that the antibody is useful as a therapeutic and/or diagnostic agent for targeting CSF1R. In some embodiments, the extent of binding of an anti-CSF1R specific antibody to an unrelated, non-CSF1R antigen is less than about 20%, less than about 15%, less than about 10%, or less than about 5% of the binding of the antibody to CSF1R as measured by, e.g., radioimmunoassay (RIA) or surface plasmon resonance (SPR). In some embodiments, an anti-CSF1R antibody of the present disclosure has a dissociation constant ($K_D$) of <1 μM, <100 nM, <10 nM, <1 nM, <0.1 nM, <0.01 nM, or <1 pM (e.g., $10^{-8}$ M or less, e.g., from $10^{-8}$M to $10^{-13}$ M, e.g., from $10^{-9}$M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fusion" refers to an antibody that is covalently conjugated (or fused) to a polypeptide or protein, typically via a linker to a terminus of the antibody's light chain (LC) or heavy chain (HC). Exemplary antibody fusions of the present disclosure include an anti-CSF1R antibody fused to a recombinant IL10 polypeptide via a 14 amino acid linker from the C-terminus of the antibody heavy chain to the N-terminus of the IL10 polypeptide. Antibody fusions are labeled herein with a "antibody/polypeptide" nomenclature to indicate the fusion components, such as "Ab/IL10" or "anti-CSFR1/IL10" or "6D4/IL10".

"Antibody fragment" refers to a portion of a full-length antibody which is capable of binding the same antigen as the full-length antibody. Examples of antibody fragments include, but are not limited to, Fv, Fab, Fab', Fab'-SH, F(ab')$_2$; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, β, ε, γ, and μ, respectively.

"Variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, 6$^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol. 150: 880-887 (1993); Clarkson et al., Nature 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the "complementarity determining regions" (CDRs). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. "Contact" hypervariable regions are based on an analysis of the available complex crystal structures. Residue ranges for hypervariable regions defined under these systems are noted in the table below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B[1] | H26-H35B[1] | H26-H32[1] | H30-H35B[1] |
|    | H31-H35[2]  | H26-H35[2]  | H26-H32[2] | H30-H35[2]  |
| H2 | H50-H65 | H50-H58 | H53-H55 | H47-H58 |
| H3 | H95-H102 | H95-H102 | H96-H101 | H93-H101 |

[1]Kabat numbering
[2]Chothia numbering

In addition to the systems described above, HVRs and CDRs can be identified using the international ImMunoGeneTics information system, referred to as IMGT/V-Quest, described in Brochet, X. et al., Nucl. Acids Res. 36, W503-508 (2008). PMID: 18503082; and available for use online at www.imgt.org/IMGT_vquest/input. IMGT/V-Quest analyzes alignments to closest germline V gene variable region nucleotide sequences using IMGT unique numbering to identify HVRs and CDRs.

Hypervariable regions (HVRs), as used herein, may include extended or alternative hypervariable regions as follows: 27-32, 27-36, 24-34, or 24-38 (HVR-L1); 50-52, 54-56, 50-56 or 54-60 (HVR-L2); 89-97 or 93-101 (HVR-L3); 26-33, 26-35, or 31-35 (HVR-H1); 51-58, 50-61, or 50-66 (H2); and 97-110, 97-112, 99-110, or 99-112 (H3) in the $V_H$ domain. The variable domain residues are numbered according to Kabat et al., supra, for each of these definitions.

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (CDR-H1, CDR-H2, CDR-H3), and three in the light chain variable domains, $V_L$ (CDR-L1, CDR-L2, CDR-L3). Exemplary CDRs occur at variable domain amino acid residue positions: 24-34, 27-32, 27-36, 24-38 (CDR-L1); 50-56, 50-52, 54-56, or 54-60 (CDR-L2); 89-97, or 93-101 (CDR-L3); 31-35, or 26-33 (CDR-H1), 50-66, or 51-58 (CDR-H2); and 99-112, 99-110, 97-112, or 97-110 (CDR-H3).

"Framework" or "FR" refers to variable domain residues other than the HVR residues. The FRs of a variable domain generally consist of four domains: FR1, FR2, FR3, and FR4. Accordingly, the HVR and FR sequences generally appear in the following sequence in $V_H$ (or $V_L$) : FR1-H1(L1)-FR2-H2(L2)-FR3-H3(L3)-FR4.

Unless otherwise indicated, the positions of residues in the HVRs, CDRs, FRs, and other residues in the variable domain are numbered herein according to Kabat et al., supra.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the HVRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcR, as used herein, also includes the neonatal receptor, FcRn, which is responsible for the transfer of maternal IgGs to the fetus (Guyer et al, J. Immunol. 1 17:587 (1976) and Kim et al, J. Immunol. 24:249 (1994)) and regulation of homeostasis of immunoglobulins. FcRs are reviewed, for example, in Ravetch and Kinet, Annu. Rev. Immunol 9:457-92 (1991); Capel et al, Immunomethods 4:25-34 (1994); and de Haas et al, J. Lab. Clin. Med. 126:330-41 (1995).

"Multispecific antibody" is an antibody having at least two different binding sites, each site with a different binding specificity. A multispecific antibody can be a full length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_D$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Fab fragment" refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically, the antigen binding arm is a complex of immunoglobulin polypeptide sequences, e.g., HVR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain. Generally, an Fv polypeptide further comprises a polypeptide linker between the $V_H$ and $V_L$ domains which enables the scFv to form the desired antigen binding structure.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M. In some embodiments, an antibody may have a secondary affinity for an antigen other than the antigen to which it binds specifically, where "secondary affinity" will generally refer to binding of an antibody to a secondary antigen with an affinity value of more than about 10 nM as described elsewhere herein. Where an antibody may have a secondary affinity for a secondary antigen, such an antibody will nevertheless bind specifically to the primary antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B 848:79-87.

"Effector function" refer to a biological activity attributed to the Fc region of an antibody, which varies with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-CSF1R antibody to a subject to delay development or slow progression of a disease or condition mediated by CSF1R and/or its binding to CSF1 or other ligands, or a disease or condition in which CSF1R may play a role in the pathogenesis and/or progression.

"Pharmaceutical formulation" refers to a preparation in a form that allows the biological activity of the active ingredient(s) to be effective, and which contain no additional components which are toxic to the subjects to which the formulation is administered. A pharmaceutical formulation may include one or more active agents. For example, a pharmaceutical formulation may include an anti-CSF1R antibody as the sole active agent of the formulation or may include an anti-CSF1R antibody and one or more additional active agents, an immune activator such as IL10, or an inhibitor of an immune checkpoint molecule.

"Sole active agent," as used herein, refers an active agent in a pharmaceutical formulation that is the only active agent present in that formulation that provides, or would be expected to provide, the relevant pharmacological effect to treat the subject for the condition being treated. A pharmaceutical formulation comprising a sole active agent does not exclude the presence of one or more non-active agents, such as e.g., a pharmaceutically acceptable carrier, in the formulation. A "non-active agent" is an agent that would not be expected to provide, or otherwise significantly contribute to, the relevant pharmacological effect intended to treat the subject for the condition.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Immune checkpoint molecule," as used herein, refers to a molecule that functions to regulate an immune system pathway and thereby prevent it from attacking cells unnecessarily. Many immune checkpoint molecules, both inhibitory and co-stimulatory, are targets for immunotherapy (e.g., with blocking antibodies to block immune inhibition or with agonists to promote immune stimulation) in the treatment of cancer and viral infections. Exemplary immune checkpoint molecules targeted for cancer immunotherapy include, but are not limited to, PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a CSF1R mediated disease or condition, the therapeutically effective amount of the therapeutic agent is an amount that reduces, prevents, inhibits, and/or relieves to some extent one or more of the symptoms associated with the disease, disorder, or condition. For cancer therapy, efficacy in vivo can, for example, be measured by assessing the growth of a primary tumor, occurrence and/or growth of secondary tumor(s), occurrence and/or number of metastases, duration, severity, and/or recurrence of symptoms, the response rate (RR), duration of response, and/or quality of life.

"Concurrently," as used herein, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

Detailed Description of Various Embodiments

I. CSF1R and CSF1

The sequence and annotation of human CSF1R (also referred to herein as "huCSF1R") can be found at UniProt entry P07333, and the full-length 972 amino acid sequence is set forth herein as SEQ ID NO: 70. The sequence and annotation of cynomolgus monkey CSF1R (also referred to herein as "cynoCSF1R") can be found at UniProt entry A0A2K5WG90, and the full-length 976 amino acid sequence is set forth herein as SEQ ID NO: 71. The sequence and annotation of the human CSF1, which is the cognate ligand CSF1R, can be found at NM_172212.2. A shorter recombinant CSF1 segment ("M-CSF1") comprising Glu33-Ser190 of human CSF1 with an N-terminal His9-(SGGG)2-IEGR-tag was used in the Examples described elsewhere herein.

Table 1 below provides a summary description of the sequences of the CSF1R proteins, and the recombinant M-CSF1 polypeptide construct used in the present disclosure, and their sequence identifiers. The sequences also are included in the accompanying Sequence Listing.

TABLE 1

CSF1R and CSF1 Sequences

| Name | Sequence | SEQ ID NO: |
|---|---|---|
| huCSF1R (P07333) | MGPGVLLLLLVATAWHGQGIPVIEPSVPELVVKPGATVTLRCVGNGSVEW DGPPSPHWTLYSDGSSSILSTNNATFQNTGTYRCTEPGDPLGGSAAIHLY VKDPARPWNVLAQEVVVFEDQDALLPCLLTDPVLEAGVSLVRVRGRPLMR HTNYSFSPWHGFTIHRAKFIQSQDYQCSALMGGRKVMSISIRLKVQKVIP GPPALTLVPAELVRIRGEAAQIVCSASSVDVNFDVFLQHNNTKLAIPQQS DFHNNRYQKVLTLNLDQVDFQHAGNYSCVASNVQGKHSTSMFFRVVESAY LNLSSEQNLIQEVTVGEGLNLKVMVEAYPGLQGFNWTYLGPFSDHQPEPK LANATTKDTYRHTFTLSLPRLKPSEAGRYSFLARNPGGWRALTFELTLRY PPEVSVIWTFINGSGTLLCAASGYPQPNVTWLQCSGHTDRCDEAQVLQVW DDPYPEVLSQEPFHKVTVQSLLTVETLEHNQTYECRAHNSVGSGSWAFIP ISAGAHTHPPDEFLFTPVVVACMSIMALLLLLLLLLLYKYKQKPKYQVRW KIIESYEGNSYTFIDPTQLPYNEKWEFPRNNLQFGKTLGAGAFGKVVEAT AFGLGKEDAVLKVAVKMLKSTAHADEKEALMSELKIMSHLGQHENIVNLL GACTHGGPVLVITEYCCYGDLLNFLRRKAEAMLGPSLSPGQDPEGGVDYK NIHLEKKYVRRDSGFSSQGVDTYVEMRPVSTSSNDSFSEQDLDKEDGRPL ELRDLLHFSSQVAQGMAFLASKNCIHRDVAARNVLLTNGHVAKIGDFGLA RDIMNDSNYIVKGNARLPVKWMAPESIFDCVYTVQSDVWSYGILLWEIFS LGLNPYPGILVNSKFYKLVKDGYQMAQPAFAPKNIYSIMQACWALEPTHR PTFQQICSFLQEQAQEDRRERDYTNLPSSSRSGGSGSSSSELEEESSSEH LTCCEQGDIAQPLLQPNNYQFC | 70 |
| cynoCSF1R (XP_005558297.1) | MGPGVLLLLLVVTAWHGQGIPVIEPSGPELVVKPGETVTLRCVGNGSVEW DGPISPHWTLYSDGPSSVLTTNNATFQNTRTYRCTEPGDPLGGSAAIHLY VKDPARPWNVLAKEVVVFEDQDALLPCLLTDPVLEAGVSLVRLRGRPLLR HTNYSFSPWHGFIIHRAKFIQGQDYQCSALMGGRKVMSISIRLKVQKVIP GPPALTLVPAELVRIRGEAAQIVCSASNIDVDFDVFLQHNTTKLAIPQRS DFHDNRYQKVLTLSLGQVDFQHAGNYSCVASNVQGKHSTSMFFRVVESAY LDLSSEQNLIQEVTVGEGLNLKVMVEAYPGLQGFNWTYLGPFSDHQPEPK LANATTKDTYRHTFTLSLPRLKPSEAGRYSFLARNPGGWRALTFELTLRY PPEVSVIWTSINGSGTLLCAASGYPQPNVTWLQCAGHTDRCDEAQVLQVW VDPHPEVLSQEPFQKVTVQSLLTAETLEHNQTYECRAHNSVGSGSWAFIP ISAGARTHPPDEFLFTPVVVACMSVMALLLLLLLLLLYKYKQKPKYQVRW KIIESYEGNSYTFIDPTQLPYNEKWEFPRNNLQFGKTLGAGAFGKVVEAT AFGLGKEDAVLKVAVKMLKSTAHADEKEALMSELKIMSHLGQHENIVNLL GACTHGGPVLVITEYCCYGDLLNFLRRKAEAMLGPSLSPGQDPEGGADYK NIHLEKKYVRRDSGFSSQGVDTYVEMRPVSTSSNDSFSEQDLDKEDGRPL ELWDLLHFSSQVAQGMAFLASKNCIHRDVAARNVLLTNGHVAKIGDFGLA RDIMNDSNYIVKGNARLPVKWMAPESIFDCVYTVQSDVWSYGILLWEIFS LGLNPYPGILVNSKFYKLVKDGYQMAQPAFAPKNIYSIMQACWALEPTHR PTFQQICSLLQEQAQEDRRERDYTNLPSSSRSGGSGSGSSSSSEPEEES SSEHLACCEQGDIAQPLLQPNNYQFC | 71 |
| human M-CSF1 | HHHHHHHHHSGGGSGGGIEGREEVSEYCSHMIGSGHLQSLQRLIDSQMETS CQITFEFVDQEQLKDPVCYLKKAFLLVQDIMEDTMRFRDNTPNAIAIVQLQ ELSLRLKSCFTKDYEEHDKACVRTFYETPLQLLEKVKNVFNETKNLLDKDW NIFSKNCNNSFAECSSQGHERQSEGS | 72 |

II. IL10

Table 2 below provides a summary description of the amino sequences of the human IL10 polypeptide and two recombinant IL10-Fc fusion constructs used in the Examples of the present disclosure, and their sequence identifiers. The sequences also are included in the accompanying Sequence Listing.

TABLE 2

Recombinant IL10 polypeptide (including IL10-Fc fusion) sequences

| Description | Sequence | SEQ ID NO: |
|---|---|---|
| IL10-Fc | SPGQGTQSENSCTHFPGNLPNMLRDLRDAFSRVKTFFQMKDQLDNLLLKE SLLEDFKGYLGCQALSEMIQFYLEEVMPQAENQDPDIKAHVNSLGENLKT LRLRLRRCHRFLPCENKSKAVEQVKNAFNKLQEKGIYKAMSEFDIFINYI EAYMTMKIRN*GGGGSGGGGSGGGGS*pkscdkthtcppcpapellggpsvf lfppkpkdtlmisrtpevtcvvvdvshedpevkfnwyvdgvevhnaktkp reeqynstyrvvsvltvlhqdwlngkeykckvsnkalpapiektiskakg qprepqvytlppsrdeltknqvsltclvkgfypsdiavewesngqpenny | 73 |

TABLE 2-continued

Recombinant IL10 polypeptide
(including IL10-Fc fusion) sequences

| Description | Sequence | SEQ ID NO: |
|---|---|---|
| | kttppvldsdgsfflyskltvdksrwqqgnvfscsvmhealhnhytqksl slspgk | |
| (IL10)₂-Fc | SPGQGTQSENSCTHFPGNLPNMLRDLRDAFSRVKTFFQMKDQLDNLLLKE SLLEDFKGYLGCQALSEMIQFYLEEVMPQAENQDPDIKAHVNSLGENLKT LRLRLRRCHRFLPCENKSKAVEQVKNAFNKLQEKGIYKAMSEFDIFINYI EAYMTMKIRN*GGGGSGGGGSGGGGS*PGQGTQSENSCTHFPGNLPNMLRDL RDAFSRVKTFFQMKDQLDNLLLKESLLEDFKGYLGCQALSEMIQFYLEEV MPQAENQDPDIKAHVNSLGENLKTLRLRLRRCHRFLPCENKSKAVEQVKN AFNKLQEKGIYKAMSEFDIFINYIEAYMTMKIRN*GGGGSGGGGSGGGGS*p kscdkthtcppcpapellggpsvflfppkpkdtlmisrtpevtcvvvdvs hedpevkfnwyvdgvevhnaktkpreeqynstyrvvsvltvlhqdwlngk eykckvsnkalpapiektiskakgqprepqvytlppsrdeltknqvsltc lvkgfypsdiavewesngqpennykttppvldsdgsfflyskltvdksrw qqgnvfscsvmhealhnhytqkslslspgk | 74 |
| IL-10 | SPGQGTQSENSCTHFPGNLPNMLRDLRDAFSRVKTFFQMKDQLDNLLLKE SLLEDFKGYLGCQALSEMIQFYLEEVMPQAENQDPDIKAHVNSLGENLKT LRLRLRRCHRFLPCENKSKAVEQVKNAFNKLQEKGIYKAMSEFDIFINYI EAYMTMKIRN | 75 |

Variable domain: UPPERCASE
Constant domain: lower case
Linker: UPPERCASE ITALICS
IL-10: UPPERCASE UNDERLINED
human IgG1 Fc fragment: Bold lower case

III. Anti-CSF1R Antibodies

In some embodiments, the present disclosure provides structures of anti-CSF1R antibodies in terms of the amino acid and encoding nucleotide sequences of the various well-known immunoglobulin features (e.g., CDRs, FRs, $V_H$, $V_L$ domains, and full-length heavy and light chains). Table 3 below provides a summary description of anti-CSF1R antibody sequences of the present disclosure, including antibody fusions, and their sequence identifiers. The sequences are included in the accompanying Sequence Listing.

TABLE 3

Anti-CSF1R antibody (including antibody fusion) sequences

| Description | Sequence | SEQ ID NO: |
|---|---|---|
| 6D4-V_H | GAGATCCAGCTGCAGCAGTCTGGAGCTGAGCTGGTGAAGCCTAGGGCTTC AGTGAAGATATCCTGCGAGGCTTCTGGTTACTCATTCACTGGCTACAACA TGAACTGGGTGAAGCAGAGCCCTGGAAAGAGCCTTGAGTGGATTGGAGAT ATTAATCCTTACTATGGTGCTACTACCTACAATCAGAAGTTCAAGGGCAA GGCCACATTGACTGTAGACAAATCTTCCAGCACAGCCTACATGCAGCTCA ACAGCCTGACATCTGAGGACTCTGCAGTCTATTACTGTGCAAGAAGAGGG GACTATGGTGACTACGAGGGCTGGTACTTCGATGTCTGGGGCGCAGGGAC CACGGTCACCGTCTCCTCA | 1 |
| 6D4-V_H | EIQLQQSGAELVKPRASVKISCEASGYSFTGYNMNWVKQSPGKSLEWIGD INPYYGATTYNQKFKGKATLTVDKSSSTAYMQLNSLTSEDSAVYYCARRG DYGDYEGWYFDVWGAGTTVTSS | 2 |
| 6D4-CDR-H1 (IMGT) | GYSFTGYN | 3 |
| 6D4-CDR-H1 (Kabat) | GYNMN | 4 |
| 6D4-HVR-H1 (Kabat) | GYSFTGYN | 5 |
| 6D4-CDR-H2 (IMGT) | INPYYGAT | 6 |
| 6D4-CDR-H2 (Kabat) 6D4-HVR-H2 (Kabat) | DINPYYGATTYNQKFKG | 7 |

TABLE 3-continued

Anti-CSF1R antibody (including antibody fusion) sequences

| Description | Sequence | SEQ ID NO: |
|---|---|---|
| 6D4-CDR-H3 (IMGT) | ARRGDYGDYEGWYFDV | 8 |
| 6D4-CDR-H3 (Kabat) | RGDYGDYEGWYFDV | 9 |
| 6D4-HVR-H3 (Kabat) | ARRGDYGDYEGWYFDV | 10 |
| 6D4-V$_L$ | GACATCCAGATGAACCAGTCTCCATCCAGTCTGTCTGCATCCCTTGGAGACACAATTACCATCACTTGCCATGCCAGTCAGAACATTAATGTTTGGTTAAGCTGGTACCAGCAGAAACCAGGAAATATTCCTAAACTATTGATCTATAAGGCTTCCAACTTGCACACAGGCGTCCCATCAAGGTTTAGTGGCAGTGGATCTGGAACAGGTTTCACATTAACCATCAGCAGCCTGCAGCCTGAAGACATTGCCACTTACTACTGTCAACAGGGTCAAAGTTATCCGTACACGTTCGGAGGGGGGACCAAGCTGGAAATAAAA | 11 |
| 6D4-V$_L$ | DIQMNQSPSSLSASLGDTITITCHASQNINVWLSWYQQKPGNIPKLLIYKASNLHTGVPSRFSGSGSGTGFTLTISSLQPEDIATYYCQQGQSYPYTFGGGTKLEIK | 12 |
| 6D4-CDR-L1 (IMGT) | QNINVW | 13 |
| 6D4-CDR-L1 (Kabat) 6D4-HVR-L1 (Kabat) | HASQNINVWLS | 14 |
| 6D4-CDR-L2 (IMGT) | KAS | n/a |
| 6D4-CDR-L2 (Kabat) 6D4-HVR-L2 (Kabat) | KASNLHT | 15 |
| 6D4-CDR-L3 (IMGT) | QQGQSYPYT | 16 |
| 6D4-CDR-L3 (Kabat) 6D4-HVR-L3 (Kabat) | QQGQSYPYT | 17 |
| 6D4.hu22-V$_H$ | CAGATTCAGCTGGTTCAGTCTGGCGCCGAAGTGAAGAAACCTGGCGCCTCTGTGAAGGTGTCCTGCAAGGCCAGCGGCTACAGCTTCACCGGCTACAACATGAACTGGGTCCGACAGGCCCCTGGCAAGAGCCTGGAATGGATCGGCGACATCAACCCCTACTACGGCGCCACCACCTACAACCAGAAATTCAAGGGCAGAGTGACCCTGACCGTGGACACCAGCACAAGCACCGCCTACATGGAACTGAGCAGCCTGAGAAGCGAGGACACCGCCGTGTACTACTGTGCCAGAAGAGGCGACTACGGCGATTACGAAGGCTGGTACTTCGACGTGTGGGGCCAGGGCACAATGGTCACAGTTAGCTCT | 18 |
| 6D4.hu22-V$_H$ | QIQLVQSGAEVKKPGASVKVSCKASGYSFTGYNMNWVRQAPGKSLEWIGDINPYYGATTYNQKFKGRVTLTVDTSTSTAYMELSSLRSEDTAVYYCARRGDYGDYEGWYFDVWGQGTMVTVSS | 19 |
| 6D4.hu22-V$_L$ | GACATCCAGATGACACAGAGCCCCAGCAGCCTGTCTGCCTCTGTGGGAGACAGAGTGACCATCACCTGTCACGCCAGCCAGAACATCAACGTGTGGCTGAGCTGGTATCAGCAGAAGCCTGGCAACGCCCCTAAGCTGCTGATCTACAAGGCCAGCAATCTGCACACCGGCGTGCCCAGCAGATTTTCTGGCTCTGGCAGCGGCACCGACTTCACCCTGACCATATCTAGCCTGCAGCCTGAGGACATTGCCACCTACTACTGTCAGCAGGGCCAGAGCTACCCCTACACATTTGGCGGAGGCACCAAGCTGGAAATCAAG | 20 |
| 6D4.hu22-V$_L$ | DIQMTQSPSSLSASVGDRVTITCHASQNINVWLSWYQQKPGNAPKLLIYKASNLHTGVPSRFSGSGSGTDFTLTISSLQPEDIATYYCQQGQSYPYTFGGGTKLEIK | 21 |
| 6D4.hu41-V$_H$ | GAGATTCAGCTGCAGCAGTCTGGCGCCGAAGTGAAGAAACCTGGCGCCTCCGTGAAGATCAGCTGTGAAGCCAGCGGCTACAGCTTCACCGGCTACAACATGAACTGGGTCAAGCAGGCCCCTGGCAAGAGCCTGGAATGGATCGGCGACATCAACCCCTACTACGGCGCCACCACCTACAACCAGAAGTTCAAGGGCAGAGCCACACTGACCGTGGACACCAGCACAAGCACCGCCTACATGGAACTGA | 22 |

TABLE 3-continued

Anti-CSF1R antibody (including antibody fusion) sequences

| Description | Sequence | SEQ ID NO: |
|---|---|---|
| | GCAGCCTGAGAAGCGAGGACACCGCCGTGTACTACTGTGCCAGAAGAGGC GACTACGGCGATTACGAAGGCTGGTACTTCGACGTGTGGGGCCAGGGCAC AATGGTCACAGTTAGCTCT | |
| 6D4.hu41-$V_H$ | EIQLQQSGAEVKKPGASVKISCEASGYSFTGYNMNWVKQAPGKSLEWIGD INPYYGATTYNQKFKGRATLTVDTSTSTAYMELSSLRSEDTAVYYCARRG DYGDYEGWYFDVWGQGTMVTVSS | 23 |
| 6D4.hu41-$V_L$ | GACATCCAGATGACACAGAGCCCCAGCAGCCTGTCTGCCTCTGTGGGAGA CAGAGTGACCATCACCTGTCACGCCAGCCAGAACATCAACGTGTGGCTGA GCTGGTATCAGCAGAAGCCTGGCAACGCCCCTAAGCTGCTGATCTACAAG GCCAGCAATCTGCACACCGGCGTGCCCAGCAGATTTTCTGGCTCTGGCAG CGGCACCGACTTCACCTTCACCATATCTAGCCTGCAGCCTGAGGACATTG CCACCTACTACTGTCAGCAGGGCCAGAGCTACCCCTACACATTTGGCGGA GGCACCAAGCTGGAAATCAAG | 24 |
| 6D4.hu41-$V_L$ | DIQMTQSPSSLSASVGDRVTITCHASQNINVWLSWYQQKPGNAPKLLIYK ASNLHTGVPSRFSGSGSGTDFTFTISSLQPEDIATYYCQQGQSYPYTFGG GTKLEIK | 25 |
| 6M6-$V_H$ | GATGTTCAACTCCAGCAGTCTGGGACTGTGCTGGCACGGCCTGGGGCTTC AGTGAAGATGTCCTGCAAGGCTTCTGGCTACACCTTTACCAGCTACTGGA TACACTGGGTAAAACAGAGGCCTGGACAGGGTCTGGAATGGATTGGCGCT ATTTATCCTGGAAATAGAGATACTAACTACAACCAGAAGTTCAAGGGCAA GGCCAAACTGACTACAGTCACATCTGCCAGCACTGCCTACATGGAGCTCA GCAGCCTGACAAATGAGGACTCTGCGGTCTATTACTGTACGGGGGCCTTT GCTGGTTACTACGACTGGTACTTCGATGTCTGGGGCGCAGGGACCACGGT CACCGTCTCCTCA | 26 |
| 6M6-$V_H$ | DVQLQQSGTVLARPGASVKMSCKASGYTFTSYWIHWVKQRPGQGLEWIGA IYPGNRDTNYNQKFKGKAKLTTVTSASTAYMELSSLTNEDSAVYYCTGAF AGYYDWYFDVWGAGTTVTVSS | 27 |
| 6M6-CDR-H1 (IMGT) | GYTFTSYW | 28 |
| 6M6-CDR-H1 (Kabat) | SYWIH | 29 |
| 6M6-HVR-H1 (Kabat) | GYTFTSYWIH | 30 |
| 6M6-CDR-H2 (IMGT) | IYPGNRDT | 31 |
| 6M6-CDR-H2 (Kabat) 6M6-HVR-H2 (Kabat) | AIYPGNRDTNYNQKFKG | 32 |
| 6M6-CDR-H3 (IMGT) 6M6-HVR-H3 (Kabat) | TGAFAGYYDWYFDV | 33 |
| 6M6-CDR-H3 (Kabat) | AFAGYYDWYFDV | 34 |
| 6M6-$V_L$ | GACATTGTGCTGACCCAATCTCCAGCTTCTTTGGCTGTGTCTCTAGGGCA GAGGGCCACCATCTCCTGCAAGGCCAGCCAAGGTGTTGATTATGCTGGTG ATAGTTATATGAACTGGTACCAACAGAAACCAGGACAGCCACCCAAACTC CTCATCTATGTTGCATCCGATCTGGATTCTGGGATCCCAGCCAGGTTTAG TGGCAGTGGGTCTGGGACAAACTTCACCCTCAACATCCATCCTGTGGAGG AGGAGGATGCTGCAACCTATTACTGTCAGCAAAGTTATGAGGATCCTCGG ACGTTCGGTGGAGGCACCACGCTGGAAATCCAA | 35 |
| 6M6-$V_L$ | DIVLTQSPASLAVSLGQRATISCKASQGVDYAGDSYMNWYQQKPGQPPKL LIYVASDLDSGIPARFSGSGSGTNFTLNIHPVEEEDAATYYCQQSYEDPR TFGGGTTLEIQ | 36 |
| 6M6-CDR-L1 (IMGT) | QGVDYAGDSY | 37 |

TABLE 3-continued

Anti-CSF1R antibody (including antibody fusion) sequences

| Description | Sequence | SEQ ID NO: |
|---|---|---|
| 6M6-CDR-L1 (Kabat)<br>6M6-HVR-L1 (Kabat) | KASQGVDYAGDSYMN | 38 |
| 6M6-CDR-L2 (IMGT) | VAS | n/a |
| 6M6-CDR-L2 (Kabat)<br>6M6-HVR-L2 (Kabat) | VASDLDS | 39 |
| 6M6-CDR-L3 IMGT | QQSYEDPRT | 40 |
| 6M6-CDR-L3 (Kabat)<br>6M6-HVR-L3 (Kabat) | QQSYEDPRT | 41 |
| 6M6.hu12-$V_H$ | CAAGTTCAGCTGCAGCAGTCTGGCGCCGAAGTGAAAAAACCTGGCGCCTC<br>CGTGAAGATGAGCTGCAAGGCCAGCGGCTACACCTTCACCAGCTACTGGA<br>TTCACTGGGTCCGACAGGCCCCTGGACAAGGCTTGGAATGGATGGGCGCC<br>ATCTATCCCGGCAACCGGGACACCAACTACAACCAGAAATTCAAGGGCAG<br>AGTGACCCTGACCACCGACACATCTGCCAGCACCGCCTACATGGAACTGA<br>GCAGCCTGAGAAGCGAGGACACCGCCGTGTACTACTGTACAGGCGCCTTT<br>GCCGGCTACTACGACTGGTACTTTGACGTGTGGGGCCAGGGCACCACCGT<br>GACAGTTAGTTCT | 42 |
| 6M6.hu12-$V_H$ | QVQLQQSGAEVKKPGASVKMSCKASGYTFTSYWIHWVRQAPGQGLEWMGA<br>IYPGNRDTNYNQKFKGRVTLTTDTSASTAYMELSSLRSEDTAVYYCTGAF<br>AGYYDWYFDVWGQGTTVTVSS | 43 |
| 6M6.hu12-$V_L$ | GACATTGTGCTGACACAGAGCCCCGATAGCCTGGCCGTGTCTCTGGGAGA<br>AAGAGCCACCATCAACTGCAAGGCCAGCCAGGGCGTTGACTACGCCGGCG<br>ACAGCTACATGAACTGGTATCAGCAGAAGCCCGGCCAGCCTCCTAAGCTG<br>CTGATCTACGTGGCCAGCGATCTGGACAGCGGCATCCCCGATAGATTTTC<br>CGGCTCTGGCTCCGGCACCGACTTCACCCTTACAATCAGTTCCCTGCAGG<br>CCGAGGACGTGGCCACCTACTATTGTCAGCAGAGCTACGAGGACCCCAGA<br>ACCTTTGGCGGCGGAACCACACTGGAAATCAAG | 44 |
| 6M6.hu12-$V_L$ | DIVLTQSPDSLAVSLGERATINCKASQGVDYAGDSYMNWYQQKPGQPPKL<br>LIYVASDLDSGIPDRFSGSGSGTDFTLTISSLQAEDVATYYCQQSYEDPR<br>TFGGGTTLEIK | 45 |
| 6M6.hu41-$V_H$ | CAAGTTCAGCTGCAGCAGTCTGGCGCCGTGGTCAAAAAACCTGGCGCCTC<br>CGTGAAGATGAGCTGCAAGGCCAGCGGCTACACCTTCACCAGCTACTGGA<br>TTCACTGGGTCAAGCAGGCCCCTGGACAGGGCCTTGAATGGATCGGAGCC<br>ATCTATCCCGGCAACCGGGACACCAACTACAACCAGAAGTTCAAGGGCAG<br>AGCCACACTGACCACCGATACCTCTGCCAGCACCGCCTACATGGAACTGA<br>GCAGCCTGACCAGCGAGGACACCGCCGTGTATTACTGTACAGGCGCCTTC<br>GCCGGCTACTACGACTGGTACTTTGATGTGTGGGGCCAGGGCACCACCGT<br>GACAGTTAGTTCTG | 46 |
| 6M6.hu41-$V_H$ | QVQLQQSGAVVKKPGASVKMSCKASGYTFTSYWIHWVKQAPGQGLEWIGA<br>IYPGNRDTNYNQKFKGRATLTTDTSASTAYMELSSLTSEDTAVYYCTGAF<br>AGYYDWYFDVWGQGTTVTVSS | 47 |
| 6M6.hu41-$V_L$ | GACATTGTGCTGACACAGAGCCCCGATAGCCTGGCCGTGTCTCTGGGAGA<br>AAGAGCCACCATCAACTGCAAGGCCAGCCAGGGCGTTGACTACGCCGGCG<br>ACAGCTACATGAACTGGTATCAGCAGAAGCCCGGCCAGCCTCCTAAGCTG<br>CTGATCTACGTGGCCAGCGATCTGGATAGCGGCGTGCCCGATAGATTTTC<br>TGGCAGCGGCTCTGGCACCGACTTCACCCTGACAATTAGCTCCCTGCAGG<br>CCGAGGATGTGGCCACCTACTACTGTCAGCAGAGCTACGAGGACCCCAGA<br>ACCTTTGGCGGCGGAACCACACTGGAAATCAAG | 48 |
| 6M6.hu41-$V_L$ | DIVLTQSPDSLAVSLGERATINCKASQGVDYAGDSYMNWYQQKPGQPPKL<br>LIYVASDLDSGVPDRFSGSGSGTDFTLTISSLQAEDVATYYCQQSYEDPR<br>TFGGGTTLEIK | 49 |
| 6D4/IL10-VH | EIQLQQSGAELVKPRASVKISCEASGYSFTGYNMNWVKQSPGKSLEWIGD<br>INPYYGATTYNQKFKGKATLTVDKSSSTAYMQLNSLTSEDSAVYYCARRG<br>DYGDYEGWYFDVWGAGTTVTVSSastkgpsvfplapssksstsggtaalgc | 50 |

TABLE 3-continued

Anti-CSF1R antibody (including antibody fusion) sequences

| Description | Sequence | SEQ ID NO: |
|---|---|---|
| | lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwingkeykckvsnkalpapiektiskakgqpr epqvytlppsreemtknqvsltclvkgfypsdiavewesngqpennykttt ppvldsdgsfflyskltvdksrwqqgnvfscsvmhealhnhytqkslsls pgk*LGGGGSGGGGSGGGGS*PGQGTQSENSCTHFPGNLPNMLRDLRDAFSR VKTFFQMKDQLDNLLLKESLLEDFKGYLGCQALSEMIQFYLEEVMPQAEN QDPDIKAHVNSLGENLKTLRLRLRRCHRFLPCENKSKAVEQVKNAFNKLQ EKGIYKAMSEFDIFINYIEAYMTMKIRN | |
| 6D4/(IL10)<sub>2</sub>-VH | EIQLQQSGAELVKPRASVKISCEASGYSFTGYNMNWVKQSPGKSLEWIGD INPYYGATTYNQKFKGKATLTVDKSSSTAYMQLNSLTSEDSAVYYCARRG DYGDYEGWYFDVWGAGTTVTVSSastkgpsvfplapsskstsggtaalgc lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwingkeykckvsnkalpapiektiskakgqpr epqvytlppsreemtknqvsltclvkgfypsdiavewesngqpennykttt ppvldsdgsfflyskltvdksrwqqgnvfscsvmhealhnhytqkslsls pgk*LGGGGSGGGGSGGGGS*PGQGTQSENSCTHFPGNLPNMLRDLRDAFSR VKTFFQMKDQLDNLLLKESLLEDFKGYLGCQALSEMIQFYLEEVMPQAEN QDPDIKAHVNSLGENLKTLRLRLRRCHRFLPCENKSKAVEQVKNAFNKLQ EKGIYKAMSEFDIFINYIEAYMTMKIRN*GGGGSGGGGSGGGGS*PGQGTQS ENSCTHFPGNLPNMLRDLRDAFSRVKTFFQMKDQLDNLLLKESLLEDFKG YLGCQALSEMIQFYLEEVMPQAENQDPDIKAHVNSLGENLKTLRLRLRRC HRFLPCENKSKAVEQVKNAFNKLQEKGIYKAMSEFDIFINYIEAYMTMKI RN | 51 |
| 6D4.hu22/IL10-VH | QIQLVQSGAEVKKPGASVKVSCKASGYSFTGYNMNWVRQAPGKSLEWIGD INPYYGATTYNQKFKGRVTLTVDTSTSTAYMELSSLRSEDTAVYYCARRG DYGDYEGWYFDVWGQGTMVTVSSastkgpsvfplapsskstsggtaalgc lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwingkeykckvsnkalpapiektiskakgqpr epqvytlppsreemtknqvsltclvkgfypsdiavewesngqpennykttt ppvldsdgsfflyskltvdksrwqqgnvfscsvmhealhnhytqkslsls pgk*LGGGGSGGGGSGGGGS*PGQGTQSENSCTHFPGNLPNMLRDLRDAFSR VKTFFQMKDQLDNLLLKESLLEDFKGYLGCQALSEMIQFYLEEVMPQAEN QDPDIKAHVNSLGENLKTLRLRLRRCHRFLPCENKSKAVEQVKNAFNKLQ EKGIYKAMSEFDIFINYIEAYMTMKIRN | 52 |
| 6D4.hu41/IL10-VH | EIQLQQSGAEVKKPGASVKISCEASGYSFTGYNMNWVKQAPGKSLEWIGD INPYYGATTYNQKFKGRATLTVDTSTSTAYMELSSLRSEDTAVYYCARRG DYGDYEGWYFDVWGQGTMVTVSSastkgpsvfplapsskstsggtaalgc lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwingkeykckvsnkalpapiektiskakgqpr epqvytlppsreemtknqvsltclvkgfypsdiavewesngqpennykttt ppvldsdgsfflyskltvdksrwqqgnvfscsvmhealhnhytqkslsls pgk*LGGGGSGGGGSGGGGS*PGQGTQSENSCTHFPGNLPNMLRDLRDAFSR VKTFFQMKDQLDNLLLKESLLEDFKGYLGCQALSEMIQFYLEEVMPQAEN QDPDIKAHVNSLGENLKTLRLRLRRCHRFLPCENKSKAVEQVKNAFNKLQ EKGIYKAMSEFDIFINYIEAYMTMKIRN | 53 |
| 6M6/IL10-VH | DVQLQQSGTVLARPGASVKMSCKASGYTFTSYWIHWVKQRPGQGLEWIGA IYPGNRDTNYNQKFKGKAKLTTVTSASTAYMELSSLTNEDSAVYYCTGAF AGYYDWYFDVWGAGTTVTVSSastkgpsvfplapsskstsggtaalgclv kdyfpepvtvswnsgaltsgvhtfpavlqssglyslssvvtvpssslgtq tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwingkeykckvsnkalpapiektiskakgqprep qvytlppsreemtknqvsltclvkgfypsdiavewesngqpennykttpp vldsdgsfflyskltvdksrwqqgnvfscsvmhealhnhytqkslslspg k*LGGGGSGGGGSGGGGS*PGQGTQSENSCTHFPGNLPNMLRDLRDAFSRVK TFFQMKDQLDNLLLKESLLEDFKGYLGCQALSEMIQFYLEEVMPQAENQD PDIKAHVNSLGENLKTLRLRLRRCHRFLPCENKSKAVEQVKNAFNKLQEK GIYKAMSEFDIFINYIEAYMTMKIRN | 54 |
| 6M6/(IL10)<sub>2</sub>-VH | DVQLQQSGTVLARPGASVKMSCKASGYTFTSYWIHWVKQRPGQGLEWIGA IYPGNRDTNYNQKFKGKAKLTTVTSASTAYMELSSLTNEDSAVYYCTGAF AGYYDWYFDVWGAGTTVTVSSastkgpsvfplapsskstsggtaalgclv kdyfpepvtvswnsgaltsgvhtfpavlqssglyslssvvtvpssslgtq | 55 |

TABLE 3-continued

Anti-CSF1R antibody (including antibody fusion) sequences

| Description | Sequence | SEQ ID NO: |
|---|---|---|
| | tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwingkeykckvsnkalpapiektiskakgqprep qvytlppsreemtknqvsltclvkgfypsdiavewesngqpennykttpp vldsdgsfflysklltvdksrwqqgnvfscsvmhealhnhytqkslslspg k*LGGGGSGGGGSGGGGS*PGQGTQSENSCTHFPGNLPNMLRDLRDAFSRVK TFFQMKDQLDNLLLKESLLEDFKGYLGCQALSEMIQFYLEEVMPQAENQD PDIKAHVNSLGENLKTLRLRLRRCHRFLPCENKSKAVEQVKNAFNKLQEK GIYKAMSEFDIFINYIEAYMTMKIRN*GGGGSGGGGSGGGGS*PGQGTQSEN SCTHFPGNLPNMLRDLRDAFSRVKTFFQMKDQLDNLLLKESLLEDFKGYL GCQALSEMIQFYLEEVMPQAENQDPDIKAHVNSLGENLKTLRLRLRRCHR FLPCENKSKAVEQVKNAFNKLQEKGIYKAMSEFDIFINYIEAYMTMKIRN | |
| 6M6.hu12/IL10-VH | QVQLQQSGAEVKKPGASVKMSCKASGYTFTSYWIHWVRQAPGQGLEWMGA IYPGNRDTNYNQKFKGRVTLTTDTSASTAYMELSSLRSEDTAVYYCTGAF AGYYDWYFDVWGQGTTVTVSSastkgpsvfplapsskstsggtaalgclv kdyfpepvtvswnsgaltsgvhtfpavlqssglyslssvvtvpssslgtq tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwingkeykckvsnkalpapiektiskakgqprep qvytlppsreemtknqvsltclvkgfypsdiavewesngqpennykttpp vldsdgsfflysklltvdksrwqqgnvfscsvmhealhnhytqkslslspg k*LGGGGSGGGGSGGGGS*PGQGTQSENSCTHFPGNLPNMLRDLRDAFSRVK TFFQMKDQLDNLLLKESLLEDFKGYLGCQALSEMIQFYLEEVMPQAENQD PDIKAHVNSLGENLKTLRLRLRRCHRFLPCENKSKAVEQVKNAFNKLQEK GIYKAMSEFDIFINYIEAYMTMKIRN | 56 |
| 6M6.hu41/IL10-VH | QVQLQQSGAVVKKPGASVKMSCKASGYTFTSYWIHWVKQAPGQGLEWIGA IYPGNRDTNYNQKFKGRATLTTDTSASTAYMELSSLTSEDTAVYYCTGAF AGYYDWYFDVWGQGTTVTVSSastkgpsvfplapsskstsggtaalgclv kdyfpepvtvswnsgaltsgvhtfpavlqssglyslssvvtvpssslgtq tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwingkeykckvsnkalpapiektiskakgqprep qvytlppsreemtknqvsltclvkgfypsdiavewesngqpennykttpp vldsdgsfflysklltvdksrwqqgnvfscsvmhealhnhytqkslslspg k*LGGGGSGGGGSGGGGS*PGQGTQSENSCTHFPGNLPNMLRDLRDAFSRVK TFFQMKDQLDNLLLKESLLEDFKGYLGCQALSEMIQFYLEEVMPQAENQD PDIKAHVNSLGENLKTLRLRLRRCHRFLPCENKSKAVEQVKNAFNKLQEK GIYKAMSEFDIFINYIEAYMTMKIRN | 57 |
| 6D4-HC | EIQLQQSGAELVKPRASVKISCEASGYSFTGYNMNWVKQSPGKSLEWIGD INPYYGATTYNQKFKGKATLTVDKSSSTAYMQLNSLTSEDSAVYYCARRG DYGDYEGWYFDVWGAGTTVTVSSastkgpsvfplapsskstsggtaalgc lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwingkeykckvsnkalpapiektiskakgqpr epqvytlppsreemtknqvsltclvkgfypsdiavewesngqpennyktt ppvldsdgsfflysklltvdksrwqqgnvfscsvmhealhnhytqkslsls pgk | 58 |
| 6D4-LC | DIQMNQSPSSLSASLGDTITITCHASQNINVWLSWYQQKPGNIPKLLIYK ASNLHTGVPSRFSGSGSGTGFTLTISSLQPEDIATYYCQQGQSYPYTFGG GTKLEIKRtvaapsvfifppsdeqlksgtasvvcllnnfypreakvqwkv dnalqsgnsqesvteqdskdstyslsstltlskadyekhkvyacevthqg lsspvtksfnrgec | 59 |
| 6D4.hu22-HC | QIQLVQSGAEVKKPGASVKVSCKASGYSFTGYNMNWVRQAPGKSLEWIGD INPYYGATTYNQKFKGRVTLTVDTSTSTAYMELSSLRSEDTAVYYCARRG DYGDYEGWYFDVWGQGTMVTVSSastkgpsvfplapsskstsggtaalgc lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwingkeykckvsnkalpapiektiskakgqpr epqvytlppsreemtknqvsltclvkgfypsdiavewesngqpennyktt ppvldsdgsfflysklltvdksrwqqgnvfscsvmhealhnhytqkslsls pgk | 60 |
| 6D4.hu22-LC | DIQMTQSPSSLSASVGDRVTITCHASQNINVWLSWYQQKPGNAPKLLIYK ASNLHTGVPSRFSGSGSGTDFTLTISSLQPEDIATYYCQQGQSYPYTFGG GTKLEIKRtvaapsvfifppsdeqlksgtasvvcllnnfypreakvqwkv dnalqsgnsqesvteqdskdstyslsstltlskadyekhkvyacevthqg lsspvtksfnrgec | 61 |

TABLE 3-continued

Anti-CSF1R antibody (including antibody fusion) sequences

| Description | Sequence | SEQ ID NO: |
|---|---|---|
| 6D4.hu41-HC | EIQLQQSGAEVKKPGASVKISCEASGYSFTGYNMNWVKQAPGKSLEWIGD INPYYGATTYNQKFKGRATLTVDTSTSTAYMELSSLRSEDTAVYYCARRG DYGDYEGWYFDVWGQGTMVTVSSastkgpsvfplapsskstsggtaalgc lvkdyfpepvtvswnsgaltsgvhtfpavlqssglyslssvvtvpssslg tqtyicnvnhkpsntkvdkkvepkscdkthtcppcpapellggpsvflfp pkpkdtlmisrtpevtcvvvdvshedpevkfnwyvdgvevhnaktkpree qynstyrvvsvltvlhqdwlngkeykckvsnkalpapiektiskakgqpr epqvytlppsreemtknqvsltclvkgfypsdiavewesngqpennyktt ppvldsdgsfflyskltvdksrwqqgnvfscsvmhealhnhytqkslsls pgk | 62 |
| 6D4.hu41-LC | DIQMTQSPSSLSASVGDRVTITCHASQNINVWLSWYQQKPGNAPKLLIYK ASNLHTGVPSRFSGSGSGTDFTFTISSLQPEDIATYYCQQGQSYPYTFGG GTKLEIKRtvaapsvfifppsdeqlksgtasvvcllnnfypreakvqwkv dnalqsgnsqesvteqdskdstyslsstltlskadyekhkvyacevthqg lsspvtksfnrgec | 63 |
| 6M6-HC | DVQLQQSGTVLARPGASVKMSCKASGYTFTSYWIHWVKQRPGQGLEWIGA IYPGNRDTNYNQKFKGKAKLTTVTSASTAYMELSSLTNEDSAVYYCTGAF AGYYDWYFDVWGAGTTVTVSSastkgpsvfplapsskstsggtaalgclv kdyfpepvtvswnsgaltsgvhtfpavlqssglyslssvvtvpssslgtq tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwlngkeykckvsnkalpapiektiskakgqprep qvytlppsreemtknqvsltclvkgfypsdiavewesngqpennykttpp vldsdgsfflyskltvdksrwqqgnvfscsvmhealhnhytqkslslspg k | 64 |
| 6M6-LC | DIVLTQSPASLAVSLGQRATISCKASQGVDYAGDSYMNWYQQKPGQPPKL LIYVASDLDSGIPARFSGSGSGTNFTLNIHPVEEEDAATYYCQQSYEDPR TFGGGTTLEIQRtvaapsvfifppsdeqlksgtasvvcllnnfypreakv qwkvdnalqsgnsqesvteqdskdstyslsstltlskadyekhkvyacev thqglsspvtksfnrgec | 65 |
| 6M6.hu12-HC | QVQLQQSGAEVKKPGASVKMSCKASGYTFTSYWIHWVRQAPGQGLEWMGA IYPGNRDTNYNQKFKGRVTLTTDTSASTAYMELSSLRSEDTAVYYCTGAF AGYYDWYFDVWGQGTTVTVSSastkgpsvfplapsskstsggtaalgclv kdyfpepvtvswnsgaltsgvhtfpavlqssglyslssvvtvpssslgtq tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwlngkeykckvsnkalpapiektiskakgqprep qvytlppsreemtknqvsltclvkgfypsdiavewesngqpennykttpp vldsdgsfflyskltvdksrwqqgnvfscsvmhealhnhytqkslslspg k | 66 |
| 6M6.hu12-LC | DIVLTQSPDSLAVSLGERATINCKASQGVDYAGDSYMNWYQQKPGQPPKL LIYVASDLDSGIPDRFSGSGSGTDFTLTISSLQAEDVATYYCQQSYEDPR TFGGGTTLEIKRtvaapsvfifppsdeqlksgtasvvcllnnfypreakv qwkvdnalqsgnsqesvteqdskdstyslsstltlskadyekhkvyacev thqglsspvtksfnrgec | 67 |
| 6M6.hu41-HC | QVQLQQSGAVVKKPGASVKMSCKASGYTFTSYWIHWVKQAPGQGLEWIGA IYPGNRDTNYNQKFKGRATLTTDTSASTAYMELSSLTSEDTAVYYCTGAF AGYYDWYFDVWGQGTTVTVSSastkgpsvfplapsskstsggtaalgclv kdyfpepvtvswnsgaltsgvhtfpavlqssglyslssvvtvpssslgtq tyicnvnhkpsntkvdkkvepkscdkthtcppcpapellggpsvflfppk pkdtlmisrtpevtcvvvdvshedpevkfnwyvdgvevhnaktkpreeqy nstyrvvsvltvlhqdwlngkeykckvsnkalpapiektiskakgqprep qvytlppsreemtknqvsltclvkgfypsdiavewesngqpennykttpp vldsdgsfflyskltvdksrwqqgnvfscsvmhealhnhytqkslslspg k | 68 |
| 6M6.hu41-LC | DIVLTQSPDSLAVSLGERATINCKASQGVDYAGDSYMNWYQQKPGQPPKL LIYVASDLDSGVPDRFSGSGSGTDFTLTISSLQAEDVATYYCQQSYEDPR TFGGGTTLEIKRtvaapsvfifppsdeqlksgtasvvcllnnfypreakv qwkvdnalqsgnsqesvteqdskdstyslsstltlskadyekhkvyacev thqglsspvtksfnrgec | 69 |

Variable domain: UPPERCASE
Constant domain: lower case
Linker: UPPERCASE ITALICS
IL-10: UPPERCASE UNDERLINED
human IgG1 Fc fragment: Bold lower case 1. Anti-CSF1R Antibody Binding Affinity and Functional Characteristics In some embodiments, the anti-CSF1R antibodies provided herein have an equilibrium dissociation constant ($K_D$) for binding to CSF1R of <100 nM, <10 nM, <1 nM, <0.1 nM, <0.01 nM, or <0.001 nM (e.g., $10^{-8}$ M or less, from $10^{-8}$ M to $10^{-13}$ M, e.g., from $10^{-9}$ M to $10^{-13}$ M.

It is contemplated that the various anti-CSF1R antibodies generated as disclosed herein include antibodies capable of high-affinity binding to hu-CSF1R, cy-CSF1R, and both hu-CSF1R and cy-CSF1R. More specifically, in some embodiments, the anti-CSF1R antibodies of the present disclosure bind to hu-CSF1R with a binding affinity of $1\times10^{-8}$M or less, $1\times10^{-9}$M or less, $1\times10^{-10}$ M or less, or $1\times10^{-11}$M or less. In some embodiments, the binding affinity is measured as the equilibrium dissociation constant ($K_D$) for binding to the huCSF1R polypeptide of SEQ ID NO: 70. In some embodiments, the anti-CSF1R antibodies of the present disclosure bind to cy-CSF1R with a binding affinity of $1\times10^{-8}$M or less, $1\times10^{-9}$M or less, $1\times10^{-10}$ M or less, or $1\times10^{-11}$M or less. In some embodiments, the binding affinity is measured as the equilibrium dissociation constant ($K_D$) for binding to the cynoCSF1R polypeptide of SEQ ID NO: 71. In some embodiments, the anti-CSF1R antibodies of the present disclosure bind to both huCSF1R and cynoCSF1R with a binding affinity of $1\times10^{-8}$M or less, $1\times10^{-9}$M or less, $1\times10^{-10}$M or less, or $1\times10^{-11}$M or less. In some embodiments, the binding affinity is measured as the equilibrium dissociation constant ($K_D$) for binding to the huCSF1R polypeptide of SEQ ID NO: 70 and the cynoCSF1R polypeptide of SEQ ID NO:75.

Generally, binding affinity of a ligand to its receptor can be determined using any of a variety of assays and expressed in terms of a variety of quantitative values. Specific CSF1R binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/012359), immunoprecipitation assays, fluorescent immunoassays, protein A immunoassays, flow cytometric and fluorescence activated cell sorting (FACS) assays, and the like.

Accordingly, in some embodiments, the binding affinity is expressed as $K_D$ values and reflects intrinsic binding affinity (e.g., with minimized avidity effects). The anti-CSF1R antibodies of the present disclosure exhibit strong binding affinities for the huCSF1R polypeptide of SEQ ID NO: 70, for example, exhibiting $K_D$ values of between 10 nM and 1 µM. Accordingly, anti-CSF1R antibodies of the present disclosure may compete with antibodies having lower affinity for the same or overlapping epitopes of CSF1R.

In some embodiments, the anti-CSF1R antibodies provided herein decrease, inhibit, and/or fully-block CSF1 binding to CSF1R, and immune regulation and/or immune signaling mediated by CSF1 binding to CSF1R, including the maintenance of TAMs in the tumor microenvironment. The ability of the antibodies to inhibit these immune regulatory and immune signaling pathways mediated by CSF1 binding to CSF1R can be assayed in vitro using known cell-based assays including those assays described in the Examples of the present disclosure.

Additionally, the anti-CSF1R antibodies provided herein comprise antibody fusions with IL10, and accordingly can provide effects mediated by IL-10 agonist activity including activating CD8+ T-cells in the tumor microenvironment. The ability of the anti-CSF1R antibody fusions with IL10 to provide IL10 agonist effects can be assayed in vitro using known cell-based assays including those cell-based assays described in the Examples of the present disclosure.

Accordingly, in some embodiments, the CSF1R antibodies of the present disclosure are characterized by one or more of following functional properties based on the ability to decrease, inhibit, and/or fully-block intracellular signaling by CSF1R-mediated pathways.

In at least one embodiment, the anti-CSF1R antibody binds to human CSF1R with a binding affinity of $1\times10^{-8}$ M or less, $1\times10^{-9}$M or less, $1\times10^{-10}$ M or less; optionally, wherein the binding affinity is measured by equilibrium dissociation constant ($K_D$) to a huCSF1R polypeptide of SEQ ID NO: 70.

In at least one embodiment, the anti-CSF1R antibody, the antibody binds to cynomolgus CSF1R with a binding affinity of $1\times10^{-8}$M or less, $1\times10^{-9}$ M or less, $1\times10^{-10\circ}$ M or less; optionally, wherein the binding affinity is measured by equilibrium dissociation constant ($K_D$) to a cynoCSF1R polypeptide of SEQ ID NO: 71.

In at least one embodiment, the anti-CSF1R antibody, the antibody decreases CSF1-induced and IL34-induced phosphorylation of huCSF1R or AKT.

In at least one embodiment, the anti-CSF1R antibody, the antibody inhibits CSF1-dependent and IL34-induced cell proliferation by at least 65%, at least 75%, at least 85%, at least 95%, or at least 100%; optionally, wherein at a CSF1 concentration of 20 ng/mL or a IL34 concentration of 33 ng/mL the antibody has an $IC_{50}$ of 5 nM or less, 1 nM or less, 0.5 nM or less, or 0.1 nM or less.

In at least one embodiment, the anti-CSF1R antibody, the antibody inhibits CSF1-dependent dependent survival of human CD14+ monocytes or monocyte-derived macrophages by at least 65%, at least 75%, at least 85%, at least 95%, or at least 100%; optionally, wherein at a CSF1 concentration of 100 ng/mL the antibody has an $IC_{50}$ of 5 nM or less, 1 nM or less, 0.5 nM or less, or 0.1 nM or less.

In at least one embodiment, the anti-CSF1R antibody, the antibody increases NK-cell mediated ADCC against CSF1R expressing 293F cells by at least 10%; at least 20%, or at least 25%.

In at least one embodiment, the anti-CSF1R antibody, the antibody decreases tumor volume in a syngeneic mouse tumor model measured at 21 days by at least 25%, at least 50%, at least 75%, or more, wherein the mouse tumor model is selected from: CT26 CRC, EMT6 TNBC, MC38 CRC, Renca RCC, LL/2 lung, Pan02 PDAC, H22 HCC, Q1 HNSCC.

In at least one embodiment, the anti-CSF1R antibody, the antibody increases blood levels of CSF1 and IL34 in a CT26 colon tumor syngeneic mouse model by at least 50-fold, at least 100-fold, at 200-fold, or at least 500-fold.

In at least one embodiment, the anti-CSF1R antibody, the antibody decreases TAM population in in a CT26 colon tumor syngeneic mouse model by at least 20%, at least 30%, at least 40%, at least 50%, at least 60%, or more; optionally, wherein the MDSC population is reduced less than 10%, less than 5%, or less.

In at least one embodiment, the anti-CSF1R antibody, the antibody increases MC/9 cell proliferation by at least 25%, at least 50%, at least 100%, at least 150%, at least 200% or more.

In at least one embodiment, the anti-CSF1R antibody, the antibody increases IFNγ and granzyme B production from activated CD8 T cells by at least 25%, at least 50%, at least 100%, or more.

In at least one embodiment, the anti-CSF1R antibody, the antibody increases CD8+LAG3+PD1+ T cell blood levels in a CT26 colon tumor syngeneic mouse model by at least 2-fold, at least 4-fold, at least 6-fold, at least 8-fold, at least 10-fold, or more.

2. Anti-CSF1R Antibody Fragments

In some embodiments, the anti-CSF1R antibody of the present disclosure can be an antibody fragment. Antibody fragments useful with the binding determinants the present disclosure include, but are not limited to, Fab, Fab', Fab'-SH, F(ab')$_2$, Fv, scFv fragments, monovalent, single domain antibody, one-armed or single-arm antibody, and other fragments described herein and known in the art. Accordingly, in some embodiments of the anti-CSF1R antibodies of the present disclosure, the antibody is an antibody fragment selected from the group consisting of F(ab')$_2$, Fab', Fab, Fv, single domain antibody (VHH), single-arm antibody, and scFv.

For a review of various antibody fragments, see e.g., Hudson et al. Nat. Med. 9: 129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO93/16185; and U.S. Pat. Nos. 5,571,894 and 5,587,458. For a description of Fab and F(ab')$_2$ fragments comprising salvage receptor binding epitope residues and having increased in vivo half-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med. 9: 129-134 (2003); and Hollinger et al, Proc. Natl, Acad, Sci. USA 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., E. coli or phage), as described herein.

3. Chimeric, Humanized, and Human Ami-CSF1R Antibodies

In some embodiments, the anti-CSF1R antibody of the present disclosure can be a chimeric antibody. (See e.g., chimeric antibodies as described in U.S. Pat. No. 4,816,567; and Morrison et al., Proc. Natl. Acad. Sci. USA, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched: antibody in which the class or subclass has been changed from that of" the parent antibody. It is contemplated that chimeric antibodies can include antigen-binding fragments thereof.

In some embodiments, the anti-CSF1R antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat'l Acad. Sci. USA 86: 10029-10033 (1989); U.S. Pat. Nos. 5,821,337, 7,527,791, 6,982,321, and 7,087,409; Kashmiri et al, Methods 36:25-34 (2005) (describing SDR (a-HVR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol, 151:2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271:2261 1-22618 (1996)).

In some embodiments, the anti-CSF1R antibody of the present disclosure can be a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor J. Immunol, 133:3001 (1984); Brodeur et al., Monoclonal Antibody Production Techniques and Applications, pp. 51-63 (Marcel Dekker, Inc., New York, 1987); and Boerner et al., J. Immunol., 147: 86 (1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Variants of Anti-CSF1R Antibodies

In at least one embodiment, improved variants of anti-CSF1R antibodies may be isolated by screening combinatorial libraries for antibodies with the desired improved functional characteristic, such as binding affinity or cross-reactivity. For example, a variety of methods are Known in the art for generating phage display libraries and screening such libraries for variant antibodies possessing the improved binding characteristics. Other methods for producing such library-derived antibodies can be found in e.g., Hoogenboom et al., Methods in Molecular Biology 178: 1-37 (O'Brien et al., ed., Human Press, Totowa, N.J., 2001); McCafferty et al., Nature 348:552-554; Clackson et al., Nature 352: 624-628 (1991); Marks et al., J. Mol. Biol. 222: 581-597 (1992); Marks and Bradbury, m Methods in Molecular Biology 248: 161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 1 19-132(2004).

6. Multispecific Antibodies

In at least one embodiment, it is contemplated that an anti-CSF1R antibody of the present disclosure can be a multispecific antibody, e.g., a bispecific antibody. In some embodiments, the multispecific antibody has at least two different binding sites, each with a binding specificity for a different antigen, at least one of which specifically binds CSF1R. In at least one embodiment, it is contemplated that the multispecific antibody is a bispecific antibody comprising a specificity for CSF1R and a specificity for another antigen that mediates immune regulation, immune signaling, and/or is expressed on a cancer or tumor cell. For example, the other specificity could be for an immune checkpoint molecule, such as PD1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, or ICOS.

Techniques for making multispecific antibodies include, but are not limited to, recombinant co-expression of two immunoglobulin heavy chain-light chain pairs having different specificities (see e.g., Milstein and Cuello, Nature 305: 537 (1983), WO 93/08829, and Traunecker et al., EMBOJ. 10: 3655 (1991)). "Knob-in-hole" engineering can also be used to generate bispecific antibodies useful with the anti-CSF1R antibodies of the present disclosure. Techniques for knob-in-hole engineering are known in the art and described in e.g., U.S. Pat. No. 5,731,168.

Multispecific antibodies can also be made by engineering "electrostatic steering" effects that favor formation of Fc-heterodimeric antibody molecules rather than homodimers TWO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol, 148(5): 1547-1553 (1992)); using "diabody" technology for making bispecific antibody fragments (see, e.g., Hollinger et al., Proc. Natl. Acad. Sci. USA, 90:6444-6448 (1993)); using single-chain Fv (scFv) dimers (see, e.g. Gruber et al., J, Immunol, 152:5368 (1994)); or tri-specific antibodies (see e.g., Tutt et al., Immunol. 147: 60 (1991).

6. Variants of Anti-CSF1R Antibodies

In some embodiments, variants of the anti-CSF1R antibodies of the present disclosure are contemplated having improved characteristics such as binding affinity and/or other biological properties of the antibody. Variants can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of CSF1R antigen binding, A. Substitution, Insertion, and Deletion Variants In some embodiments, anti-CSF1R antibody variants having one or more amino acid substitutions in addition to those described herein are provided. Sites for mutagenesis can include the HVRs and FRs, Typical "conservative" amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class Amino acid side chains are typically grouped according to the following classes or common properties: (1) hydrophobic: Met, Ala, Val, Len, Ile, Norleucine; (2) neutral hydrophilic: Cys, Ser, Thr, Asn, Gin; (3) acidic: Asp, Glu; (4) basic: His, Lys, Arg; (5) chain orientation influencing: Gly, Pro; and (6) aromatic: Trp, Tyr, Phe. Techniques are well-known in the art for amino acid substitution into an antibody and subsequent screening for desired function, e.g., retained/improved antigen binding, decreased immunogenicity, or improved ADCC or CDC.

Amino acid substitution variants can also include variants having one or more substitutions in hypervariable regions of a parent antibody. Generally, the resulting variant(s) selected for further study will have modifications of certain biological properties (e.g., increased affinity, reduced immunogenicity) relative to the parent antibody and/or will retain certain biological properties of the parent antibody. An exemplary substitutional variant is an affinity matured antibody, which may be conveniently generated, using phage display-based affinity maturation techniques. Briefly, one or more HVR residues are mutated and the variant antibodies displayed on phage and screened for a particular biological activity (e.g., binding affinity).

One useful method for identifying residues or regions of an antibody that may be targeted for mutagenesis is "alanine scanning mutagenesis" (see e.g., Cunningham. and Wells (1989) Science, 244: 1081-1085). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions, Alternatively, or additionally, a crystal structure of an antigen-antibody complex to identify contact points between the antibody and antigen can be determined. Such contact residues and neighboring residues may be targeted or eliminated as candidates for substitution. Variants inlay be screened to determine whether they contain the desired properties.

Amino acid sequence insertions which can be prepared include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule can include a fusion of the N- or C-terminus of the antibody to an enzyme or a polypeptide which increases antibody serum half-life.

Other residue substitutions can be made in HVRs to improve antibody affinity. Such alterations may be made in "hotspots," i.e., residues encoded by codons that undergo mutation at high frequency during the somatic maturation process (see, e.g., Chowdhury, Methods Mol. Biol. 207: 179-196 (2008)) with the resulting variant $V_H$ or $V_L$ being tested for binding affinity. In one embodiment, affinity maturation can be carried out by constructing and reselecting from secondary libraries (see e.g., in Hoogenboom et al., Methods in Molecular Biology 178: 1-37 (O'Brien et al., ed., Human Press, Totowa, N.J., (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted. Generally, substitutions, insertions, or deletions can be made within one or more HVRs so long as such alterations do not substantially reduce the ability of the antibody to bind antigen. For example, conservative alterations e.g., conservative substitutions as provided herein) that do not substantially reduce binding affinity may be made in HVRs. Such alterations may be outside of HVR "hotspots."

In some embodiments, it is contemplated that the anti-CSF1R antibody described herein can be substituted at specific non-HVR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541, In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

B. Glycosylation Variants

In some embodiments, the anti-CSF1R antibody of the present disclosure is altered to increase or decrease the extent to which the antibody is glycosylated. Addition or deletion of glycosylation sites to an antibody can be carried out by altering the amino acid sequence such that one or more glycosylation sites is created or removed. In embodiments where the antibody comprises an Fc region, the carbohydrate attached to the Fc region can be altered. Typically, native antibodies produced by mammalian cells comprise a branched, biantennary oligosaccharide attached by an N-linkage to the asparagine at about position 297 ("N297") of the CH2 domain of the Fc region (see, e. g., Wright et al. TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties.

In some embodiments, the anti-CSF1R antibody of the present disclosure can be a variant comprising a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain attached to residue N297, relative to the sum of all glyco-structures attached at N297 (e.g., complex, hybrid and high mannose structures) as measured by MALDI-TOF mass spectrometry (see e.g., WO 2008/077546).

In some embodiments, the fucosylation variants can provide improved ADCC function of the variant antibody. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/01115614; US2002/0164328; US2004/0093621; US2004/0132140; US2004/0110704; US 2004/0110282; US2004/0109865; WO2000/61739; WO2001/29246; WO2003/085119; WO2003/084570; WO2005/035586; WO2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Cell lines useful for producing defucosylated antibodies include Led 3 CHO cells deficient in protein fucosylation (see e.g., Ripka et al. Arch. Biochem. Biophys. 249:533-545 (1986); US2003/0157108, and WO2004/056312), and knockout cell lines, such as alpha-1,6-fucosyltransferase gene, PUTS, knockout CHO cells (see, e.g., Yamane-Ohnuki et al. Biotech. Bioeng. 87: 614 (2004); Kanda, Y. et al., Biotechnol. Bioeng., 94(4); 680-688 (2006); and WO2003/085107).

C. Fc Region Variants

In some embodiments, an anti-CSF1R antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-CSF1R antibodies of the present disclosure are described below.

In some embodiments, the anti-CSF1R antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important. Fc region variant antibodies having reduced effector or effectorless function can result from amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581).

Some Fc region variants are capable of providing improved or diminished binding to FcRs (see e.g., U.S. Pat. No. 6,737,056; WO 2004/056312; and Shields et J. Biol. Chem. 9(2): 6591-6604 (2001)). Some Fc region variants capable of providing improved ADCC comprise one or more amino acid substitutions at e.g., positions 298, 333, and/or 334 of the Fc region (based on EU numbering). Fc region variants having altered (i.e., either improved or diminished) Clq binding and/or Complement Dependent Cytotoxicity (CDC), as described in e.g., U.S. Pat. No. 6,194,551, WO99/51642, and Idusogie et al., Immunol. 164: 4178-4184 (2000).

Some Fc region variants are capable of providing increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., US 765892182 (Dall'Acqua et al.). Additional examples of Fc region variants can be found in e.g., U.S. Pat. Nos. 5,648,260 and 5,624,821; and WO94/29351.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC, NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., Proc. Nat'l Acad. Sci. USA 83:7059-7063 (1986)) and Hellstrom, et al., Proc. Nat'l Acad. Sci, USA 82: 1499-1502 (1985): U.S. Pat. No. 5,821,337 (see Bruggemann, M. et al., J. Exp. Med. 166: 1351-1361 (1987)). Alternatively, non-radioactive assay methods may be employed (see, for example, ACTI™ nonradioactive cytotoxicity assay for flow cytometry (CellTechnology, Inc. Mountain View, Calif.; and Cyto-Tox96® non-radioactive cytotoxicity assay (Promega, Madison, We. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al, Proc. Nat'l Acad. Sci, USA 95:652-656 (1998). Clq binding assays may also be carried out to confirm that the antibody is unable to bind Clq and hence lacks CDC activity. See, e.g., Clq and C3c binding ELISA in WO2006/029879 and WO2005/100402. To assess complement activation, a CDC assay may be performed (see, e.g., Gazzano-Santoro et al., J. Immunol. Methods 202: 163 (1996); Cragg, M. S. et al., Blood 101: 1045-1052 (2003); and Cragg, M. S. and M. J. Glennie, S W 103:2738-2743 (2004)). FcRn binding and in vivo clearance/half-life determinations can be performed using methods known in the art (see, e.g., Petkova, et al., Intl, Immunol. 18(12): 1759-1769 (2006)).

D. Non-protein Antibody Derivatives—Immunoconjugates

In some embodiments, the anti-CSF1R antibody of the present disclosure may be further modified (i.e., derivatized) with non-proteinaceous moieties, Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1, 3-dioxolane, poly-1, 3, 6-trioxane, ethylene; maleic anhydride copolymer, poly-amino acid homo-polymers or random co-polymers, and dextran poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to the particular properties or functions of the antibody, e.g., whether the antibody derivative will be used in a therapy under defined conditions.

In some embodiments, the anti-CSF1R antibody of the present disclosure can also be an immunoconjugate, wherein the immunoconjugate comprises an anti-CSF1R antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes. In some embodiments, the immunoconjugate is an antibody-drug conjugate (ADC) in which an anti-CSF1R antibody, as described herein, is conjugated to one or more drugs. In some embodiments, an immunoconjugate of the present disclosure comprises an anti-CSF1R antibody as described herein conjugated to a drug or therapeutic agent for the treatment of a CSF1R-mediated disease or condition.

In some embodiments, an anti-CSF1R antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, restrictocin, phenomycin, enomycin, and the tricothecenes.

In some embodiments, an immunoconjugate of the present disclosure comprises an anti-CSF1R antibody as described herein conjugated to a radioactive isotope (i.e., a radioconjugate). A variety of radioactive isotopes are available for the production of such radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu. In some embodiments, the immunoconjugate may comprise a radioisotope for scintigraphic detection, or a spin label for NMR detection or MRI. Suitable radioisotopes or spin labels can include, as $^{123}$I, $^{131}$I, $^{111}$In, $^{13}$C, $^{19}$F, $^{15}$N, $^{17}$O, various isotopes of Gd, Mn, and Fe.

Immunoconjugates of an anti-CSF1R antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene). Reagents for preparing immunoconjugates of the present disclosure can also include commercially available "cross-linking" reagents such as: BMPS, EMCS, GMBS, HBVS, LC-SMCC, MBS, MPBH, SBAP, SIA, STAB, SMCC, SMPB, SMPH, sulfo-FMCS, sulfo-GMBS, sulfo-KMUS, sulfo-MBS, sulfo-SIAB, sulfo-SMCC, and sulfa-SMPB, and SVSB (succinimidyl-(4-vinylsulfone)benzoate) (see e.g., Pierce Biotechnology, Inc., Rockford, IL., U.S.A.).

IV. Recombinant Methods and Compositions

The anti-CSF1R antibody of the present disclosure can be produced using recombinant methods and materials well-known in the art of antibody production. In some embodiments, the present disclosure provides an isolated nucleic acid encoding an anti-CSF1R antibody. The nucleic acid can encode an amino acid sequence comprising the $V_L$ and/or an amino acid sequence comprising the $V_H$ of the antibody (e.g., the light and/or heavy chains of the antibody). In some embodiments, one or more vectors (e.g., expression vectors) comprising nucleic acid sequences encoding an anti-CSF1R antibody of the present disclosure are provided. In some embodiments, a host cell comprising nucleic acid sequences encoding an anti-CSF1R antibody of the present disclosure are provided. In one embodiment, the host cell has been transformed with a vector comprising a nucleic acid that encodes an amino acid sequence comprising the $V_L$, of the antibody and an amino acid sequence comprising the $V_H$ of the antibody. In another embodiment, the host cell has been transformed with a first vector comprising a nucleic acid that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In one embodiment, a method of making an anti-CSF1R antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-CSF1R antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech. 22: 1409-1414 (2004), and Li et al., Nat. Biotech. 24:210-215 (2006)).

Suitable host cells for the expression of glycosylated anti-CSF1R antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-CSF1R antibodies of the present disclosure include Chinese hamster ovary (CHO) cells, including DHFR-CHO cells (see e.g., Urlaub et al., Proc. Natl. Acad. Sci. USA 77:4216 (1980)); myeloma cell lines such as Y0, NS0 and Sp2/0; monkey kidney CV1 line transformed by SV40 (COS-7); human embryonic kidney line (293 or 293 cells as described, e.g., in Graham et al., J. Gen Vinyl. 36:59 (1977)); baby hamster kidney cells (BHK) mouse Sertoli cells (TM4 cells as described, e.g., in Mather, Biol. Reprod. 23:243-251 (1980)); monkey kidney cells (CVI); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells (see e.g., in Mather et al., Annals N Y. Acad. Sci. 383:44-68 (1982) and U.S. Pat. No. 6,235,498); Medical Research Council 5 (MRC 5) cells (such as e.g., those available from ATCC and also referred to as CCL-171); and Foreskin 4 (FS-4) cells (see e.g., in Vilcek et al. Ann. N. Y. Acad. Sci, 284:703-710 (1977), Gardner & Vilcek. J. Gen. Viral. 44:161-168 (1979), and Pang et al. Proc. Natl. Acad. Sci, U.S.A. 77:5341-5345 (1980)). For a general review of useful mammalian host cell lines suitable for antibody production, see, e.g., Yazaki and Wu, Methods in Molecular Biology, Vol. 248 (B.K.C. Lo, ed., Humana Press, Totowa, N.J.), pp. 255-268 (2003).

V. Pharmaceutical Compositions and Formulations of Anti-CSF1R Antibodies

The present disclosure also provides pharmaceutical compositions and pharmaceutical formulations comprising an anti-CSF1R antibody. In some embodiments, the present disclosure provides a pharmaceutical formulation comprising an anti-CSF1R antibody as described herein and a pharmaceutically acceptable carrier. In some embodiments, the anti-CSF1R antibody is the sole active agent of the pharmaceutical composition. Such pharmaceutical formulations can be prepared by mixing an anti-CSF1R antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267,958).

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl (alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

It is also contemplated that the formulations disclosed herein may contain active ingredients in addition to the anti-CSF1R, as necessary for the particular indication being treated in the subject to whom the formulation is administered. Preferably, any additional active ingredient has activity complementary to that of the anti-CSF1R antibody and the activities do not adversely affect each other.

As disclosed elsewhere herein, including the Examples, it has been shown that the anti-CSF1R antibodies of the present disclosure can be used in combination with an IL10 polypeptide to provide improved therapeutic effect in treating cancers. Accordingly, in some embodiments the present disclosure provides a pharmaceutical composition or formulation useful for treating a cancer comprising a CSF1R antagonist (such as an anti-CSF1R) and an IL10 agonist (such as an IL10). In addition, to the use of the anti-CSF1R antibodies of the present disclosure as CSF1R antagonist in such a pharmaceutical formulation or composition, it is also contemplated that other antagonists can be used, including but not limited to a shRNA, a siRNA, a miRNA, a small molecule inhibitor of CSF1R, or a combination thereof. Small molecule inhibitors of CSF1R useful in such pharmaceutical compositions or formulations can include known compounds in clinical development including, but not limited to, Pexidartinib, ARRY-382, PRV-6527, BLZ-945, DCC-3014, and PLX-7486. Besides the anti-CSF1R antibodies of the present disclosure, other known anti-CSF1R antibodies useful in such a combination pharmaceutical composition or formulation with an IL10 can include any known antibodies that bind CSF1R, including those in clinical development for cancer treatment such as Emactuzumab, Cabiralizumab, AMG820, and LY3022855.

As described elsewhere herein, in some embodiments the present disclosure provides pharmaceutical composition or formulation for use in a combination therapy comprising a CSF1R antagonist and an IL10 agonist. In some embodiments, this combination can be provided as a single pharmaceutical composition or formulation comprising an anti-CSF1R antibody fusion having an anti-CSF1R antibody covalently fused to a IL10 through a polypeptide linker, such as 14 amino acid linker of SEQ ID NO: 78. Examples demonstrating such anti-CSF1R antibody fusions (e.g., 6D4/IL10, 6D4/(IL10)$_2$, 6D4.hu22/IL10, etc.) and their use in pharmaceutical compositions for reducing tumor volume in a range of syngeneic mouse cancer models is provided elsewhere herein.

In some embodiments, the pharmaceutical composition comprises the anti-CSF1R antibody and an additional active agent for cancer treatment such as an immune checkpoint inhibitor. Checkpoint inhibitors useful in such embodiments include, but are not limited to, a second antibody comprising a specificity for an antigen that is an immune checkpoint molecule. In some embodiments, the second antibody comprises a specificity for an immune checkpoint molecule selected from PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS. In at least one embodiment, the pharmaceutical composition comprising an anti-CSF1R antibody and an additional active agent, wherein the additional active agent is an antibody comprising a specificity for the immune checkpoint molecule PD1. Exemplary antibodies comprising a specificity for PD1 that are useful in the pharmaceutical composition embodiments disclosed herein include, but are not limited to, dostarlimab, pembrolizumab, nivolumab, and pidilizumab.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

IV. Uses and Methods of Treatment

It is contemplated that any of the compositions or formulations comprising an anti-CSF1R antibody of the present disclosure can be used for any methods or uses, such as in therapeutic methods that utilize their ability to specifically bind to CSF1R and thereby inhibit, decrease, and/or fully block the function of CSF1R as a receptor involved in immune regulation or signaling, particularly the function of CSF1R regulating the survival and maintenance of tumor-associated macrophages (TAMs). TAMs are a major cellular component of tumor microenvironment (TME), and contribute significantly to tumor growth and progression. Inhibition of CSF1R signaling can deplete TAMs and thereby induce an increase in anti-tumor T-cell response.

There are a range of diseases, disorders, and conditions that can potentially be treated by inhibiting, decreasing, and/or fully blocking the immune regulatory and/or immune signaling activity of CSF1R, particularly, the effect of CSF1R on TAMs. Diseases, disorders, and conditions include, but are not limited to, cancers, including but not limited to colon cancer, pancreatic cancer, ovarian cancer, HCC, renal cancer, breast cancer, lung cancer, gastric cancer, head and neck cancer, or oral cancer. It is contemplated that any of the compositions or formulations comprising an anti-CSF1R antibody of the present disclosure, including anti-CSF1R antibody fusions with IL-10 polypeptide, can be used for a method or use for the treatment of any of the above-listed cancers. In some embodiments, the cancer is selected from colon cancer, pancreatic cancer, ovarian cancer, HCC, renal cancer, breast cancer, lung cancer, gastric cancer, head and neck cancer, or oral cancer. In some embodiments, the present disclosure provides a method of treating cancer in a subject, the method comprising administering to the subject in need thereof a therapeutically effective amount of an anti-CSF1R antibody of the present disclosure or administering to a subject a therapeutically effective amount of a pharmaceutical composition comprising an anti-CSF1R antibody of the present disclosure and a pharmaceutically acceptable carrier.

As disclosed herein, including in the Examples below, the anti-CSF1R antibodies of the present disclosure have the ability to decrease, inhibit, and/or block CSF1 binding to CSF1R, and thereby alter CSF1 interaction with the immune signaling pathways mediated by CSF1R. Accordingly, in some embodiments, the present disclosure provides a method of treating a CSF1R-mediated disease or condition in a subject, the method comprising administering to the subject a therapeutically effective amount of an anti-CSF1R antibody of the present disclosure or administering to a subject in need thereof a therapeutically effective amount of a pharmaceutical composition comprising an anti-CSF1R antibody of the present disclosure and a pharmaceutically acceptable carrier. Similarly, in some embodiments, the present disclosure provides a method of treating a disease mediated by binding to CSF1R expressed on cells in a subject, the method comprising administering to the subject, the method comprising administering to the subject a therapeutically effective amount of an anti-CSF1R antibody of the present disclosure or administering to a subject in need thereof a therapeutically effective amount of a pharmaceutical composition comprising an anti-CSF1R antibody of the present disclosure and a pharmaceutically acceptable carrier.

Administration of the anti-CSF1R antibody, composition, or pharmaceutical formulation in accordance with the method of treatment provides an antibody-induced therapeutic effect that protects the subject from and/or treats the progression of a CSF1R-mediated disease in a subject. In some embodiments, the method of treatment can further comprise administration of one or more additional therapeutic agents or treatments known to those of skill in the art to prevent and/or treat the CSF1R-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

The cytokine IL-10 exhibits anti-inflammatory and CD8+ T-cell activation properties. A strong IL-10 signal can promote tumor-specific CD8+ T-cell proliferation, revitalize exhausted T-cells, and thereby increase T-cell cytotoxicity. Accordingly, in at least one embodiment, the present disclosure contemplates a method of treatment that uses an CSF1R antagonist (e.g., anti-CSF1R antibody) in combination with an IL10 agonist. In at least one embodiment, this combination therapy can be carried out using an anti-CSF1R antibody fusion with an IL10 polypeptide. As disclosed herein, the combination of CSF1R inhibition to reduce immunosuppressive TAMs together with a concentrated IL10 signal nearby in the TME to enhance CD8+ T-cell cytotoxicity can provide an improved cancer therapy. Accordingly, in any of the embodiments of methods of treating a CSF1R-mediated disease (e.g., cancer) using an anti-CSFR1 antibody of the present disclosure, it is contemplated that the anti-CSF1R antibody can be an antibody fusion (or fusion protein) with an IL10 polypeptide as disclosed elsewhere herein.

It is also contemplated that other CSF1 antagonists can be used in such a combination treatment with an IL10, including but not limited to a shRNA, a siRNA, a miRNA, or a small molecule inhibitor of CSF1R, or a combination thereof. Small molecule inhibitors of CSF1R useful in such a method can include known CSF1R inhibitor compounds in clinical development such as Pexidartinib, ARRY-382, PRV-6527, BLZ-945, DCC-3014, and PLX-7486. Additionally, other known CSF1R antagonist antibodies can be used in such a combination treatment with an IL10 including known antibodies that block CSF1R, including those in clinical development for cancer treatment such as Emactuzumab, Cabiralizumab, AMG820, and LY3022855.

In some embodiments of the methods of treatment of the present disclosure, the anti-CSF1R antibody or pharmaceutical formulation comprising an anti-CSF1R antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion.

In some embodiments, a pharmaceutical formulation of the anti-CSF1R antibody is formulated such that the antibody is protected from inactivation m the gut. Accordingly, the method of treatments can comprise oral administration of the formulation.

In some embodiments, use of the compositions or formulations comprising an anti-CSF1R antibody of the present disclosure as a medicament are also provided. Additionally, in some embodiments, the present disclosure also provides for the use of a composition or a formulation comprising an anti-CSF1R antibody in the manufacture or preparation of a medicament, particularly a medicament for treating, preventing or inhibiting a CSF1R-mediated disease. In a further embodiment, the medicament is for use in a method for treating, preventing or inhibiting a CSF1R-mediated disease comprising administering to an individual having a CSF1R-mediated disease an effective amount of the medicament. In certain embodiments, the medicament further comprises an effective amount of at least one additional therapeutic agent, or treatment. In at least one embodiment, the additional therapeutic agent or treatment is an IL10 agonist, such as an IL10 polypeptide, that is administered in combination with an anti-CSF1R antibody (rather than as an antibody fusion).

As disclosed elsewhere herein, it is also contemplated that additional therapeutic agents or treatments that can be used in such medicaments with anti-CSF1R antibodies of the present disclosure can include but are not limited to therapeutic antibodies comprising a specificity for an immune checkpoint molecule such as PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS. Exemplary antibodies comprising a specificity for an immune checkpoint molecule include, but are not limited to an anti-PD1 antibody selected from dostarlimab, pembrolizumab, nivolumab, and pidilizumab.

In a further embodiment, the medicament is for use in treating, inhibiting or preventing a CSF1R-mediated disease, such as a cancer, in a subject comprising administering to the subject an amount effective of the medicament to treat, inhibit or prevent the CSF1R-mediated disease.

The appropriate dosage of the anti-CSF1R antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-CSF1R antibody included in the compositions and formulations described herein, can be suitably administered to the patient at one time, or over a series of treatments. Various dosing schedules including but not limited to single or multiple administrations over various timepoints, bolus administration, and pulse infusion are contemplated herein.

Depending on the type and severity of the disease, about 1 µg/kg to 15 mg/kg of anti-CSF1R antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg, to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the CSF1R-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-CSF1R antibody comprises a daily dosage from about 1 mg/kg to about 100 me/kg. In some embodiments, the dosage of anti-CSF1R antibody comprises a daily dosage of at least about 1 mg/kg, at least about 5 mg; kg, at least about 10 mg; kg, at least about 20 mg/kg, or at least about 30 mg/kg.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1

Generation of Anti-CSF1R Antibodies

This example illustrates the use of hybridoma technology to generate two exemplary anti-CSF1R monoclonal antibodies of the present disclosure, hy6D4 and hy6M6.

A. Generation of Hybridoma Cell Lines Producing Anti-CSF1R Antibodies

Materials and methods: 13 mice were immunized with a recombinant human CSF1R extracellular domain (ECD)-Fc fusion protein (R&D Systems). The splenocytes from immunized mice were isolated and fused with a mouse myeloma cell line using PEG based standard protocols to generate hybridomas. Hybridomas were plated in flat bottom 96 well microtiter plate, followed by 2-4 weeks incubation in selective medium. The stable subclones are then cultured in vitro to produce antibody in tissue culture medium for characterization. As described below, the culture supernatant of hybridomas was screened for binding to human CSF1R (SEQ ID NO: 70) and the ability to inhibit ligand-induced AML5 proliferation. Antibodies purified from the selected hybridoma supernatants were further analyzed for CSF1R epitope binding characteristics, the ability to block ligand binding to human CSF1R, the ability to bind cynomolgus CSF1R, and the ability to inhibit ligand-induced CSF1R phosphorylation.

B. CSF1R Specific ELISA

Materials and methods: Recombinant human CSF1R-His (Biolegend), or CSF1R-Fc fusion protein were immobilized on 96 well microtiter plate at a concentration of 1 µg/mL in Coating Solution (SeraCare) overnight at 4° C. The wells were washed with wash solution (0.05% Tween20 in imidazole-buffered saline) and blocked with 1% BSA. Hybridoma culture supernatants or serial dilutions of antibodies were added to wells. After incubation at 37° C. for 1 h, the wells were washed with wash solution. Peroxidase-conjugated goat anti-human kappa light chain antibody (Bethyl) was applied to each well at 37° C. for 1 h incubation. After washing, the wells were developed with TMB substrate for 5-10 min at RT and then stopped with 1 N HCl. Thereafter absorbance was measured at 450 nm and 650 nm. The $EC_{50}$ values were calculated through GraphPad Prism7.

Results: As shown in Table 4, the antibodies of the hybridoma clones labeled as "hy6D4" and "hy6M6" exhibited strong sub-nanomolar binding to the recombinant human CSF1R in monomer and fusion dimer forms.

TABLE 4

Binding activity of antibodies to human CSF1R

| mAb | EC$_{50}$ (M) | |
| --- | --- | --- |
|  | CSF1R-His (monomer) | CSF1R-Fc (dimer) |
| hy6D4 | $5.31 \times 10^{-10}$ | $3.81 \times 10^{-10}$ |
| hy6M6 | $1.12 \times 10^{-10}$ | $6.53 \times 10^{-11}$ |

C. Inhibition of Ligand-Binding to CSF1R Using Competition ELISA

Materials and methods: Recombinant human CSF1R-Fc fusion protein was immobilized on 96 well microtiter plate at a concentration of 1 µg/mL in Coating Solution (SeraCare) overnight at 4° C. The wells were washed with wash solution and blocked with 1% BSA at RT. Serial dilutions of the antibodies were added to wells. Then 2.5 ug/mL biotinylated CSF1-His (Biolegend) was added and incubated for 1 h at 37° C. After washing, Streptavidin-HRP (Jackson ImmunoResearch) was applied to wells at RT for 1 h incubation. After washing, the wells were developed with TMB substrate for 5-10 min at RT and the stopped with 1 N HCl. Thereafter absorbance was measured at 450 nm and 650 nm. The IC$_{50}$ values were calculated through GraphPad Prism7.

Results: As shown in Table 5, the anti-CSF1R antibodies hy6D4 and hy6M6 exhibited strong (nanomolar level) blocking activity against the ligand, CSF1 binding to its cognate receptor, CSF1R.

TABLE 5

Blocking activity of antibodies to interaction of CSF1R and CSF1

| mAb | IC$_{50}$ (M) |
| --- | --- |
| hy6D4 | $1.76 \times 10^{-9}$ |
| hy6M6 | $1.04 \times 10^{-9}$ |

D. Epitope Binning Studies

Materials and methods: Epitope binning studies were performed by Bio-Layer Interferometry (BLI, ForteBio Octet RED96). Streptavidin-coated Octet biosensor tips (ForteBio) were used to epitope bin a set of anti-CSF1R antibodies (6D4 and 6M6). In the beginning, 10 µg/mL of the biotinylated recombinant human CSF1R-His (Biolegend) was loaded onto streptavidin sensor tips to acquire 2 nm shift. Following 100 s and 120 s baseline steps, 5 µg/mL of a primary saturating anti-CSF1R antibody purified from hybridoma supernatant (hy6M6) was individually loaded in an association step for 600s onto the tips. Further, 5 µg/mL of the secondary competing anti-CSF1R antibody (either hy6M6 or hy6D4) was also incubated with biosensor tips for 600s association. If the signal showed mass accumulation to the tips, it was considered to bind to a different epitope.

Figure 1B:
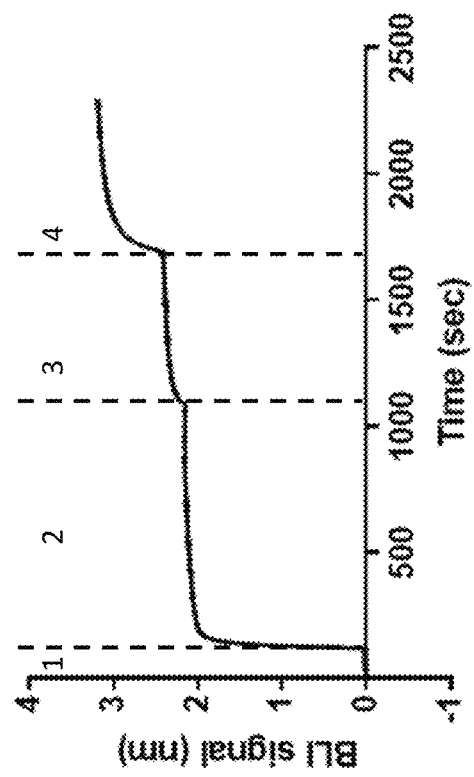

Results: As shown by the plots depicted in FIG. 1A and FIG. 1B, the sensors went through multiple assay steps (indicated by numbers and divided by dotted lines) including: step 1-baseline; step 2-biotin-CSF1R antigen capture; step 3-saturation with 1$^{st}$ mAb (hy6M6); and step 4-competition with 2$^{nd}$ mAb hy6D4 (FIG. 1A) or hy6M6 (FIG. 1B). The shift in the plot of FIG. 1A at step 4 that is not present in step 4 of FIG. 1B, clearly indicates that the two anti-CSF1R antibodies from purified supernatants, hy6D4 and hy6M6, bind to different epitopes on the CSF1R polypeptide

Example 2

Preparation of Chimeric Anti-CSF1R Antibodies, 6D4 and 6M6

This example illustrates the use recombinant genetic technologies to prepare from the two antibodies, hy6D4 and hy6M6, two exemplary chimeric anti-CSF1R monoclonal antibodies of the present disclosure, 6D4 and 6M6.

A. Construction, Expression and Purification of Chimeric Antibodies

Materials and Methods:

Total RNA was extracted from hybridoma clones hy6D4 and hy6M6 by RNeasy Mini Kit (Qiagen). The coding sequences of the variable region of the Igh and Igl/Igk genes were obtained by 5' RACE method (Takara Bio). The primer used for IgG1 VH amplification was: GATTACGC-CAAGCTTATAGACAGATGGGGGTGTCGTTTTGGC (SEQ ID NO: 76). The primer used for Kappa VL amplification was: GATTACGCCAAGCTTGGATA-CAGTTGGTGCAGCATC (SEQ ID NO: 77). Framework and complementarity determining regions (CDRs) were determined using IMGT/V-Quest program (www.imgt.org/IMGT_vquest/vquest). The antibody variable region constructs were cloned into a cDNA expression vector reformatted to a chimeric antibody comprising a human IgG1 heavy chain constant region, and a human κ light chain constant region.

The chimeric antibodies were transiently expressed in ExpiCHO-S cells (Thermo Scientific). During exponential growing phage, 6×10$^6$ ExpiCHO-S cells were transiently transfected with 20 µg of the vectors encoding chimeric antibodies by ExpiFectamine CHO Transfection Kit (Thermo Scientific). 18-22 hours after transfection, Expi-Fectamine CHO Enhancer and ExpiCHO Feed were added to the flask. The cells were cultured for 8 days. The supernatant of each culture was centrifuged and subsequently filtered through a 0.45 µm filter.

The chimeric antibodies, referred to herein as "6D4" and "6M6," were purified from transfected cell supernatants with Protein A Sepharose Fast Flow beads (GE Healthcare). Antibody loaded columns were washed with 20 column volumes of PBS, and then eluted with 3 beads volume of 0.1 M Glycine (pH 2.5) directly into 1/10 volume of 1M Tris buffer (pH 9.0). Antibody containing fractions were pooled and dialyzed against PBS. The quality of purified antibodies was examined by SDS-PAGE in the presence and absence of a reducing agent. The amino acid sequences of the chimeric antibodies 6D4 and 6M6 are provided in Table 3 and the accompanying sequence listing.

B. Cellular binding and species cross-reactivity studies using flow cytometry

Materials and methods: The gene segments encoding full-length human CSF1R amino acid sequence of SEQ ID NO: 70 or the cynomolgus CSF1R amino acid sequence of SEQ ID NO: 71 were obtained using Thermo gene synthesis service and cloned in a mammalian expression vector pCDNA3.4. Freestyle 293-F cells (Thermo Scientific) were transfected with CSF1R expression vector by polyethylenimine (PEI) method and selected with Geneticin (Thermo Scientific) to establish CSF1R stable cell lines. AML5 human acute myeloid leukemia cells (ACC 247, DSMZ) or CSF1R-overexpressing 293F cells were incubated with control human IgG1 (BioXcell), or anti-CSF1R mAb (1 µg/10$^6$ cells) for 1 h at 4° C. After washing with FACS buffer (2%

FBS in PBS), the cells were stained with anti-human IgG—Alexa Fluor 647 and analyzed by Attune NxT Flow Cytometer (Thermo Scientific).

Figure 2A:
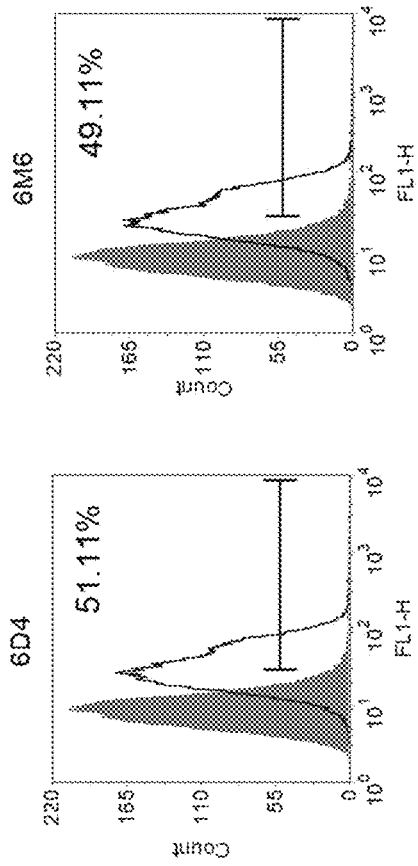
FIG. 2A, FIG. 2B, and FIG. 2C depict histograms showing the cross-species binding of the chimeric anti-CSF1R antibodies, "6D4" and "6M6" to human and cynomolgus CSF1R proteins in representative flow cytometry experiments carried out as described in Example 2.
Figure 2B:
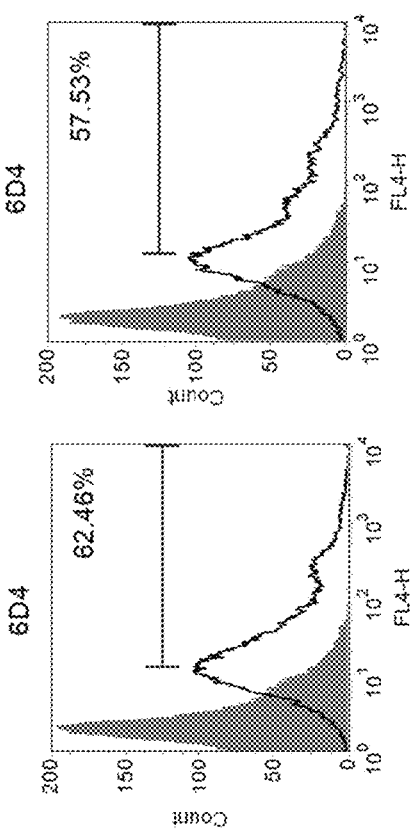
Figure 2C:
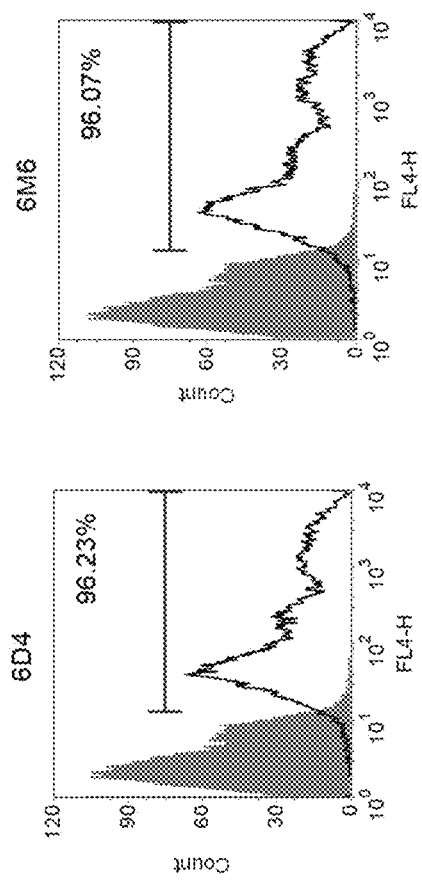

Results: As shown in FIGS. 2A, 2B, and 2C, the chimeric anti-CSF1R antibodies, 6D4 and 6M6 exhibit specific binding to AML5 cells (FIG. 2A) and 293F cells (FIG. 2B) that express human CSF1R. 6D4 and 6M6 also exhibit specific binding to 293F cells that express the cynomolgus CSF1R (FIG. 2C).

C. Inhibition of Ligand-Induced CSF1R Phosphorylation by Chimeric Anti-CSF1R Antibodies, 6D4 and 6M6

Materials and methods: AML5 cells were cultured according to DSMZ protocol and maintained in log phase. AML5 cells ($2\times10^6$) were incubated with control hIgG1, or anti-CSF1R mAb (1 μg/mL) in 1 mL assay medium (MEMα containing Glutamax) for 5-10 min at RT. The cells then were stimulated with 50 ng/mL CSF1 (R&D Systems) or 50 ng/mL IL-34 (R&D Systems) for 5 min at 37° C. After the incubation, cells were then lysed, and total proteins were extracted. 50 μg proteins were analyzed by probing Western blots with antibodies against total CSF1R (Cell Signaling), phospho-CSF1R (Tyr723) (Cell Signaling), total AKT (Cell Signaling), phospho-AKT (Tyr723) (Cell Signaling), or β-actin (Cell Signaling).

Figure 3B:
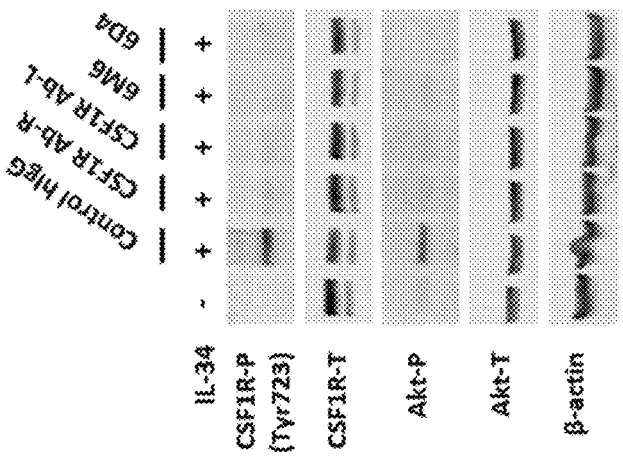
FIG. 3A and FIG. 3B depict Western blot gel images showing the attenuation of ligand induced CSF1R and AKT phosphorylation in AML5 cells in the presence of anti-CSF1R antibodies. As described in Example 2, AML5 cells were pre-treated for 5 min with control hIgG, commercial anti-CSF1R antibodies, "CSF1R Ab-R" and "CSF1R Ab-L," chimeric anti-CSF1R antibody, 6D4 or 6M6, and then stimulated for 5 min with either CSF1 (FIG. 3A), or IL-34 (FIG. 3B). Cell lysates were probed in Western blot for total (T) and phosphor (P) CSF1R and AKT.
Figure 3A:
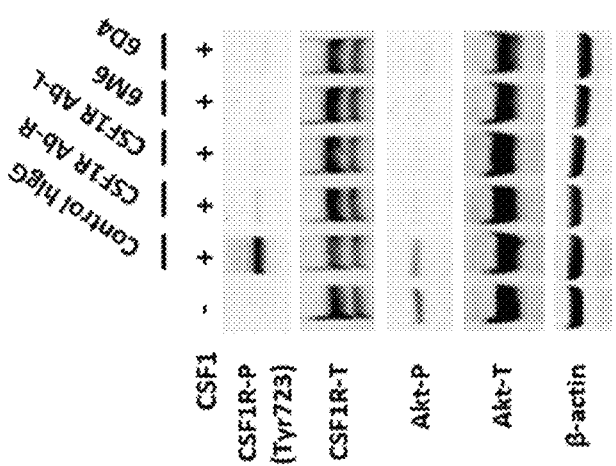

Results: As shown in FIGS. 3A and 3B, the chimeric anti-CSF1R antibodies, 6D4 and 6M6, inhibited the ligand-induced phosphorylation of CSF1R expressed on AML5 cells, where the ligand used was CSF1 (FIG. 3A) or IL-34 (FIG. 3B).

D. Inhibition of Ligand-Dependent AML5 Cell Proliferation by Anti-CSF1R Antibodies, 6D4 and 6M6

Materials and methods: In the proliferation assay, AML-5 cells ($1.5\times10^4$ per well) were incubated with serious dilutions of control hIgG1, or anti-CSF1R antibodies in assay medium (MEMα containing Glutamax) in 96-well plate. CSF1 (20 ng/mL) or IL-34 (33 ng/mL) were then added to seeded cells for 72 hours stimulation. AML-5 cell proliferation was measured using CellTiter-Glo assay (Promega).

Figure 4A:
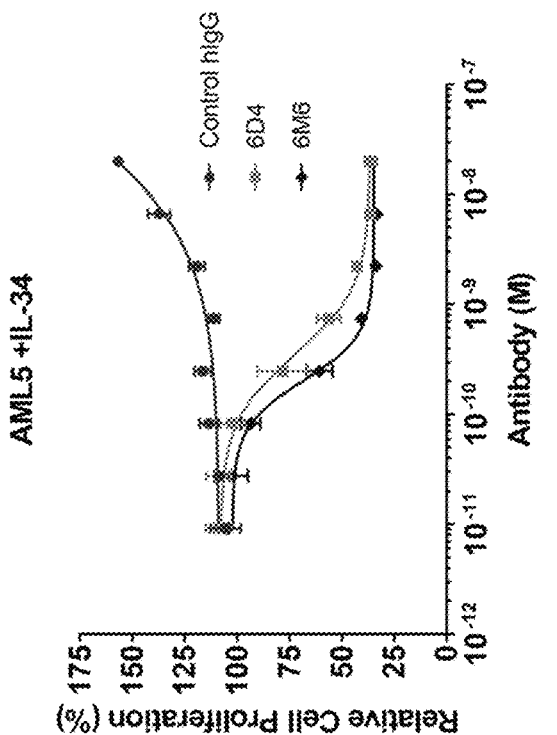
FIG. 4A, FIG. 4B, FIG. 4C, and FIG. 4D depict plots showing the inhibition of CSF1 or IL-34 ligand-dependent cell proliferation in presence of the chimeric anti-CSF1R antibodies, 6D4 and 6M6. As described in Example 2, AML5 cells were incubated for 3 days with CSF1 (FIG. 4A) or IL-34 (FIG. 4B) and different concentrations of the control, hIgG, the chimeric anti-CSF1R antibodies, 6D4 and 6M6; or AML5 cells were incubated for 3 days with CSF1 and humanized anti-CSF1R antibodies, "6D4.hu22," "6D4.hu41" (FIG. 4C) or "6M6.hu12" and "6M6.hu41" (FIG. 4D). Cell proliferation was measured by CellTiter-Glo assay.
Figure 4B:
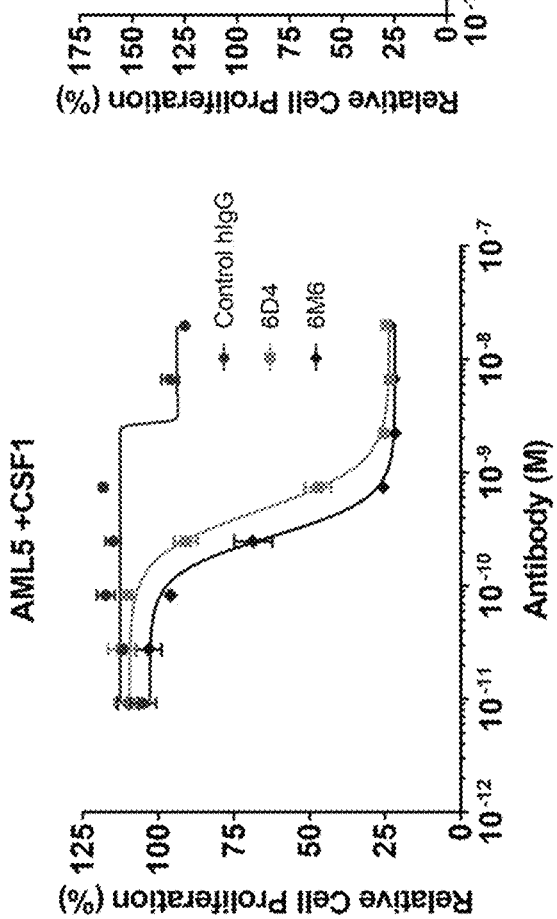

Results: As shown in FIGS. 4A and 4B, the chimeric anti-CSF1R antibodies, 6D4 and 6M6, inhibited ligand-dependent proliferation of AML5 cells induced by the ligands CSF1 (FIG. 4A) or IL-34 (FIG. 4B). The $IC_{50}$ values determined from the FIG. 4A and FIG. 4B plots for 6D4 and 6M6 are shown in Table 6.

TABLE 6

CSF1 and IL-34 ligand-dependent inhibition

| | $IC_{50}$ (M) | |
|---|---|---|
| mAb | CSF1-dependent | IL-34-dependent |
| 6D4 | $4.62 \times 10^{-10}$ | $3.49 \times 10^{-10}$ |
| 6M6 | $2.73 \times 10^{-10}$ | $2.01 \times 10^{-10}$ |

E. Inhibition of CSF1-Dependent Cell Survival of Monocytes and Macrophages by Anti-CSF1R Antibodies, 6D4 and 6M6

Human peripheral blood was obtained from healthy donors. peripheral blood mononuclear cells (PBMC) were immediately isolated by density gradient centrifugation using Ficoll-Paque Plus (GE Healthcare). CD14+ monocytes were isolated by using anti-human CD14 conjugated magnetic beads (Miltenyi Biotec). In the cell survival assay, CD14+ monocytes ($1\times10^4$ per well) were incubated with serious dilutions of control hIgG1, or anti-CSF1R antibodies in culture medium (RPMI1640 containing 10% FBS) in 96-well plate. CSF1 (100 ng/mL) was then added to cells. Cell survival was measured 6 days post stimulation using CellTiter-Glo assay (Promega).

To generate monocyte-derived macrophages, human CD14+ monocytes were cultured at $2\times10^6$ cells/mL in RPMI1640 supplemented with 10% FBS and 100 ng/mL CSF1 for 6 days. In the proliferation assay, the differentiated macrophages ($2\times10^4$ per well) were incubated with serious dilutions of control hIgG1, or anti-CSF1R antibodies in culture medium (RPMI1640 containing 10% FBS) in 96-well plate. CSF1 (10 ng/mL) was then added to cells. Cell survival was measured 72 hours post stimulation using CellTiter-Glo assay (Promega).

Figure 5B:
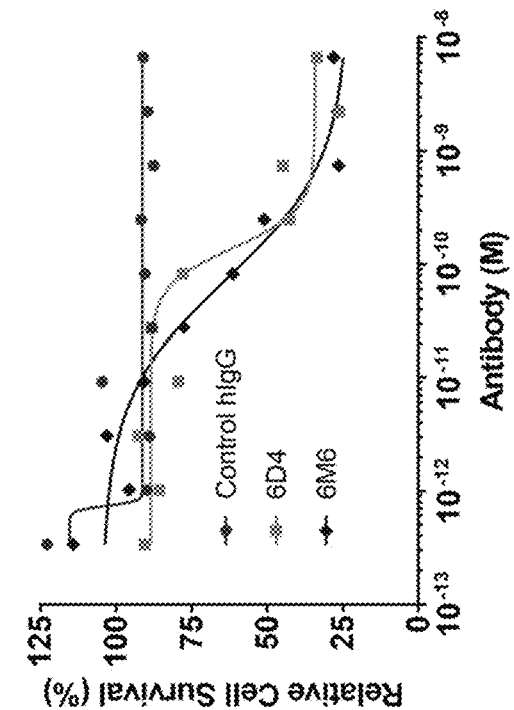
FIG. 5A, FIG. 5B, FIG. 5C and FIG. 5D depict plots showing the inhibition of CSF1-dependent cell survival in presence of anti-CSF1R antibodies. Human CD14+ blood monocytes (FIG. 5A) or monocyte-derived macrophages (FIG. 5B) were incubated with CSF1 and different concentrations of control hIgG, chimeric anti-CSF1R antibodies 6D4 and 6M6; or human CD14+ blood monocytes were incubated with different concentrations of chimeric anti-CSF1R antibody 6D4 and humanized antibodies, 6D4.hu22 and 6D4.hu41 (FIG. 5C) or chimeric anti-CSF1R antibody 6M6 and humanized antibodies, 6M6.hu12 and 6M6.hu41 (FIG. 5D). Cell survival was measured by CellTiter-Glo assay.
Figure 5A:
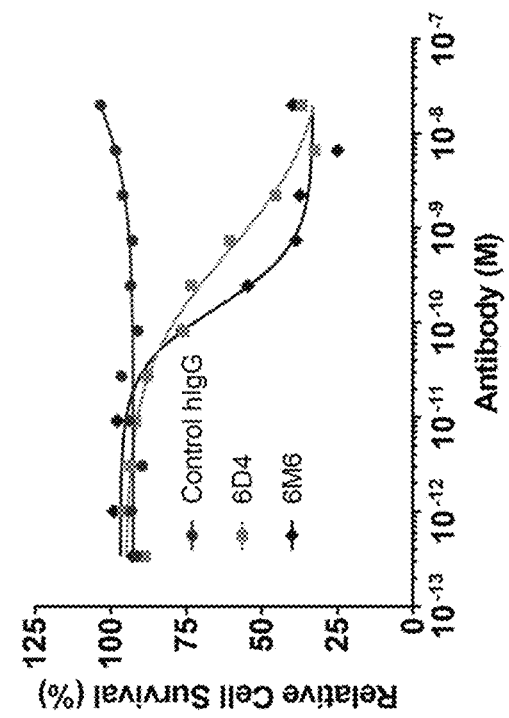

Results: As shown in FIGS. 5A and 5B, the chimeric anti-CSF1R antibodies, 6D4 and 6M6, inhibited the CSF1-dependent survival of human CD14+ monocytes and macrophages derived from the monocytes. The $IC_{50}$ values determined from the FIGS. 5A and 5B plots for 6D4 and 6M6 are shown in Table 7.

TABLE 7

Inhibition of CSF1-dependent survival of monocytes and macrophages

| | $IC_{50}$ (M) | |
|---|---|---|
| mAb | CD14 + monocytes | Macrophages |
| 6D4 | $5.58 \times 10^{-10}$ | $1.38 \times 10^{-10}$ |
| 6M6 | $1.44 \times 10^{-10}$ | $0.72 \times 10^{-10}$ |

F. Determination of CSF1R Binding Affinity of Anti-CSF1R Antibodies

Kinetic rate constants, ka and kd, for binding of 6D4 and 6M6 to CSF1R were measured by Bio-Layer Interferometry (BLI) (ForteBio Octet RED96). The BLI assay was performed using AHC (Anti-hIgG Fc Capture) biosensors (ForteBio) to capture each anti-CSF1R antibody (2 μg/mL) to acquire a 0.5 nm shift and then the biosensors were dipped into varying concentrations (i.e. 0, 0.549, 1.65, 4.94, 14.8, 44.4, 133.3 and 400 nM) of recombinant CSF1R-His protein in running buffer containing PBS-Tween 20 (0.1%), BSA (0.1%). Rate constants were calculated by curve fitting analyses (1:1 Langmuir model) of binding response with a 5-minute association and 15-minute dissociation interaction time.

Results: The binding constant, KD, and the rate constants, ka and kd, determined for binding of the chimeric anti-CSF1R antibodies, 6D4 and 6M6, to hu-CSF1R are shown in Table 8.

TABLE 8

Binding kinetics of antibodies to human CSF1R

| mAb | $K_a$ (1/Ms) | $K_d$ (1/s) | $K_D$ (M) |
|---|---|---|---|
| 6D4 | $2.77 \times 10^5$ | $9.46 \times 10^{-4}$ | $3.42 \times 10^{-9}$ |
| 6M6 | $6.88 \times 10^5$ | $2.23 \times 10^{-4}$ | $3.25 \times 10^{-10}$ |

G. Antibody-Dependent Cell-Mediated Cytotoxicity (ADCC) Assay

Human NK cells were isolated from PBMC by using NK Cell Isolation Kit (Miltenyi Biotec). In 96-well plate, 293F/huCSF1R target cells ($5\times10^3$ cells/well) were pre-incubated for 30 minutes with 3 μg/mL of the anti-CSF1R antibody. NK effector cells ($1\times10^5$ cells/well) at an effector: target (E:T) ratio of 20:1 were then add to the culture and incubated for 5 h at 37° C. The cytotoxicity was determined using the CytoTox-Glo Cytotoxicity Assay (Promega).

Figure 6:
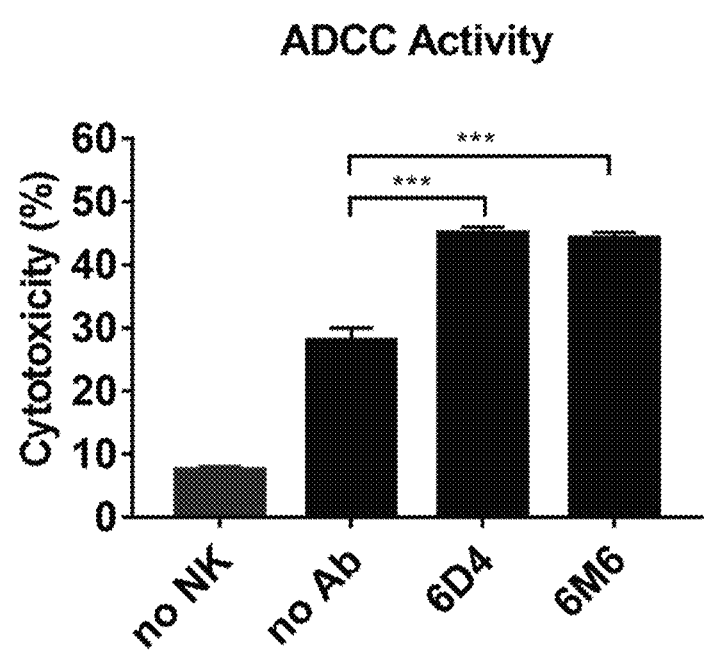
FIG. 6 shows the enhancement of natural killer (NK)-cell mediated antibody-dependent cellular cytotoxicity (ADCC) in presence of anti-CSF1R antibodies. Fresh isolated NK effector cells and 293F/CSF1R target cells were mixed at an E:T ratio of 20:1 in the presence of anti-CSF1R antibodies and incubate at 37° C. for 5 hr. Cytotoxicity was determined by CytoTox-Glo Cytotoxicity Assay (Promega).

Results: As shown in FIG. 6, the anti-CSF1R antibodies, 6D4 and 6M6, both induce enhanced natural killer (NK)-cell mediated antibody-dependent cellular cytotoxicity (ADCC).

Example 3

Preparation and Functional Analysis of Humanized Anti-CSF1R Antibodies

This example illustrates studies in which exemplary humanized anti-CSF1R antibodies of the present disclosure were prepared and functionally characterized.

A. Humanization of 6D4 and 6M6

The anti-CSF1R antibodies 6D4 and 6M6 were humanized by changing certain amino acid residues in the framework regions (FR) of the heavy and light chain variable regions (VH and VL) while maintaining the CDRs. A total of four humanized VH region and three humanized VL regions were designed for 6D4 or 6M6. The resulting 12 humanized antibodies were functionally assayed for binding to CSF1R, thermostability, non-specific binding to baculovirus, aggregation potential and capillary electrophoresis. Two humanized versions of 6D4, "6D4.hu22" and "6D4.hu41" and two humanized versions of 6M6, "6M6.hu12" and "6M6.hu41" were selected for further functional characterization. The amino acid sequences of the four humanized antibodies are provided in Table 3 and the accompanying Sequence Listing.

B. CSF1R Specific ELISA

Materials and methods: Recombinant human CSF1R-His (Biolegend), or CSF1R-Fc fusion protein, were immobilized on 96 well microtiter plate at a concentration of 1 µg/mL in Coating Solution (SeraCare) overnight at 4° C. The wells were washed with wash solution (0.05% Tween20 in imidazole-buffered saline) and blocked with 1% BSA. Serial dilutions of the antibodies were added to wells. After incubation at 37° C. for 1 h, the wells were washed with wash solution. Peroxidase-conjugated goat anti-human kappa light chain antibody (Bethyl) was applied to each well at 37° C. for 1 h incubation. After washing, the wells were developed with TMB substrate for 5-10 min at RT and then stopped with 1 N HCl. Thereafter absorbance was measured at 450 nm and 650 nm. The $EC_{50}$ values were calculated through GraphPad Prism7.

Results: As shown in Table 9, the humanized antibodies of 6D4.hu22 and 6D4.hu41, and 6M6.hu12 and 6M6.hu41 exhibited sub-nanomolar binding to the recombinant human CSF1R in monomer and fusion dimer forms, that was comparable or better than the chimeric parent antibodies, 6D4 and 6M6.

TABLE 9

Binding activity of antibodies to human CSF1R

| mAb | $EC_{50}$ (M) | |
|---|---|---|
| | CSF1R-His (monomer) | CSF1R-Fc (dimer) |
| 6D4 | $5.31 \times 10^{-10}$ | $3.81 \times 10^{-10}$ |
| 6D4.hu22 | $2.11 \times 10^{-10}$ | $1.45 \times 10^{-10}$ |
| 6D4.hu41 | $2.03 \times 10^{-10}$ | $1.39 \times 10^{-10}$ |
| 6M6 | $1.12 \times 10^{-10}$ | $6.53 \times 10^{-11}$ |
| 6M6.hu12 | $1.03 \times 10^{-10}$ | $6.13 \times 10^{-11}$ |
| 6M6.hu41 | $1.07 \times 10^{-10}$ | $6.50 \times 10^{-11}$ |

C. Inhibition of CSF1-Dependent AML5 Cell Proliferation by Humanized Anti-CSF1R Antibodies, 6D4.hu22, 6D4.hu41, 6M6.hu12, and 6M6.hu41

Materials and methods: AML-5 cells ($1.5 \times 10^4$ per well) were incubated with serious dilutions of control hIgG1, or anti-CSF1R antibodies in assay medium (MEMα containing Glutamax) in 96-well plate. CSF1 (20 ng/mL) was then added to seeded cells for 72 hours stimulation. AML-5 cell proliferation was measured using CellTiter-Glo assay (Promega).

Figure 4D:
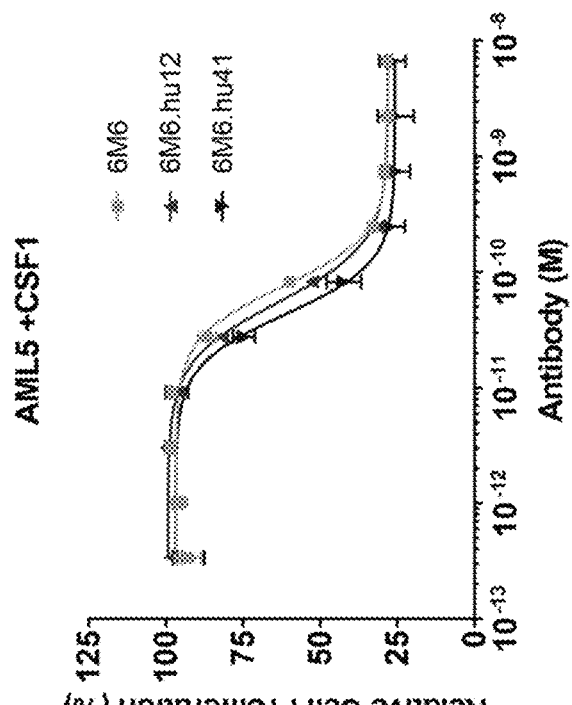
Figure 4C:
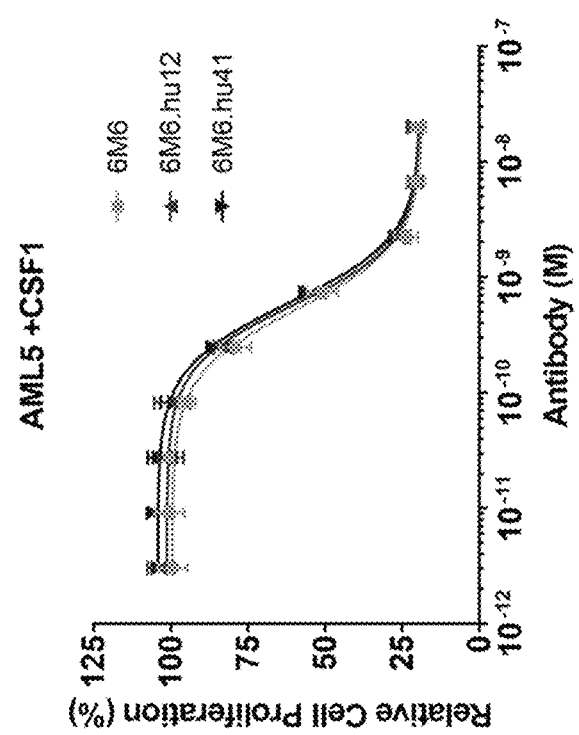

Results: As shown in FIGS. 4C and 4D, the humanized anti-CSF1R antibodies, 6D4.hu22, 6D4.hu41, 6M6.hu12, and 6M6.hu41, inhibited ligand-dependent proliferation of AML5 cells induced by the ligand CSF1. The $IC_{50}$ values determined from the FIG. 4C and FIG. 4D plots for 6D4.hu22, 6D4.hu41, 6M6.hu12, and 6M6.hu41, shown in Table 10, are comparable to the values for the parent chimeric antibodies.

TABLE 10

CSF1 ligand-dependent inhibition

| mAb | $IC_{50}$ (M) CSF1-dependent |
|---|---|
| 6D4 | $4.62 \times 10^{-10}$ |
| 6D4.hu22 | $5.71 \times 10^{-10}$ |
| 6D4.hu41 | $5.97 \times 10^{-10}$ |
| 6M6 | $2.73 \times 10^{-10}$ |
| 6M6.hu12 | $5.46 \times 10^{-10}$ |
| 6M6.hu41 | $4.30 \times 10^{-10}$ |

D. Inhibition of CSF1-Dependent Cell Survival of Monocytes by Humanized Anti-CSF1R Antibodies, 6D4.hu22, 6D4.hu41, 6M6.hu12, and 6M6.hu41

Human PBMC were isolated by density gradient centrifugation using Ficoll-Paque Plus (GE Healthcare). CD14+ monocytes were isolated by using anti-human CD14 conjugated magnetic beads (Miltenyi Biotec). In the cell survival assay, CD14+ monocytes ($1 \times 10^4$ per well) were incubated with serious dilutions of control hIgG1, or anti-CSF1R antibodies in culture medium (RPMI1640 containing 10% FBS) in 96-well plate. CSF1 (100 ng/mL) was then added to cells. Cell survival was measured 6 days post stimulation using CellTiter-Glo assay (Promega).

Figure 5D:
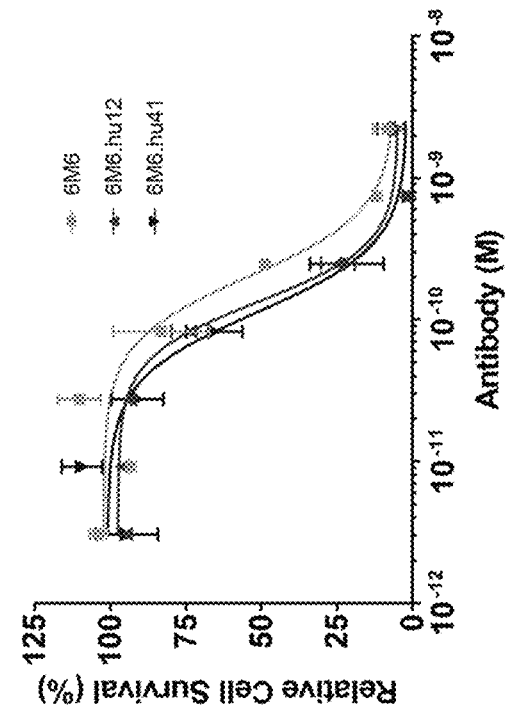
Figure 5C:
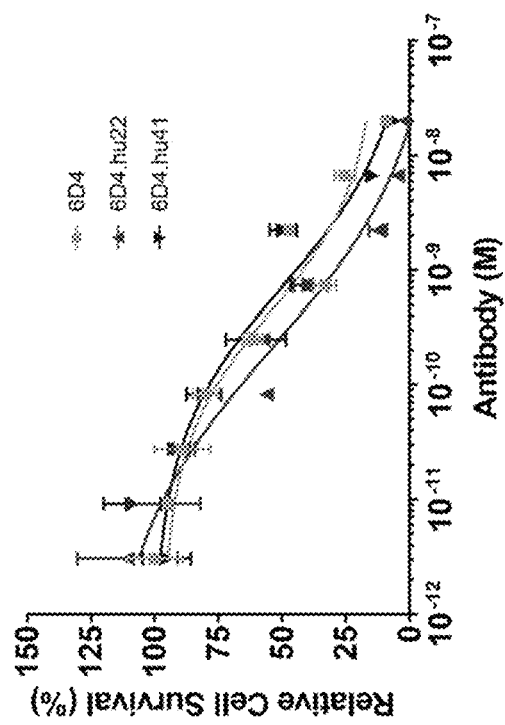

Results: As shown in FIGS. 5C and 5D, the humanized anti-CSF1R antibodies, 6D4.hu22, 6D4.hu41, 6M6.hu12, and 6M6.hu41, inhibited the CSF1-dependent survival of human CD14+ monocytes. The $IC_{50}$ values determined from the FIGS. 5C and 5D plots for 6D4 and 6M6.

Example 4

Anti-CSF1R Combination Immunotherapy with IL10 Agonist

This example illustrates studies in which exemplary anti-CSF1R antibodies are used in combination with an IL10 agonist to treat tumors.

A. Preparation of IL10 Agonists

Materials and methods: Recombinant IL10-Fc (SEQ ID NO: 73) and $(IL10)_2$-Fc (SEQ ID NO: 74) fusion proteins were designed by genetically fusing human IL-10 to the N-terminus of the human IgG1-Fc separated by a 14 amino acid linker GGGGSGGGGSGGGG (SEQ ID NO: 78). The desired genes encoding the fusion proteins, were preceded by an IL-2 secretion sequence for production of the recombinant protein. The genes were obtained using a gene synthesis service (Thermo Scientific). The gene segment was cloned in a mammalian expression vector, and the recombinant IL10-Fc and (IL10)$_2$-Fc proteins were expressed in transfected ExpiCHO cells. Successful preparation of the IL10-Fc and (IL10)$_2$-Fc fusion proteins was confirmed by SDS-PAGE.

B. Anti-Tumor Activity of Anti-CSF1R and IL-10 in Syngeneic CT26 Colon Cancer Model Materials and methods: BALB/c mice (6-8 weeks old, female) were implanted subcutaneously with 5×10$^5$ CT26.WT cells (ATCC CRL-2638). After 7 days, mice were randomized into treatment groups when tumor volume reached 50-100 mm$^3$. Mice were then injected intraperitoneally twice weekly with 30 mg/kg rat IgG isotype control (BioXcell), 30 mg/kg anti-CSF1R (clone AFS98, BioXcell), 20 mg/kg human Fc control (BioXcell), or 20 mg/kg IL10-Fc fusion protein (SEQ ID NO: 73). Tumor volume was measured twice per week by caliper measurements until end of the study. The blood samples were collected weekly. Concentrations of mouse CSF1, IL-34, IL-18 and CXCL9 in plasma were measured by ELISA kits (Biolegend).

Figure 7A:
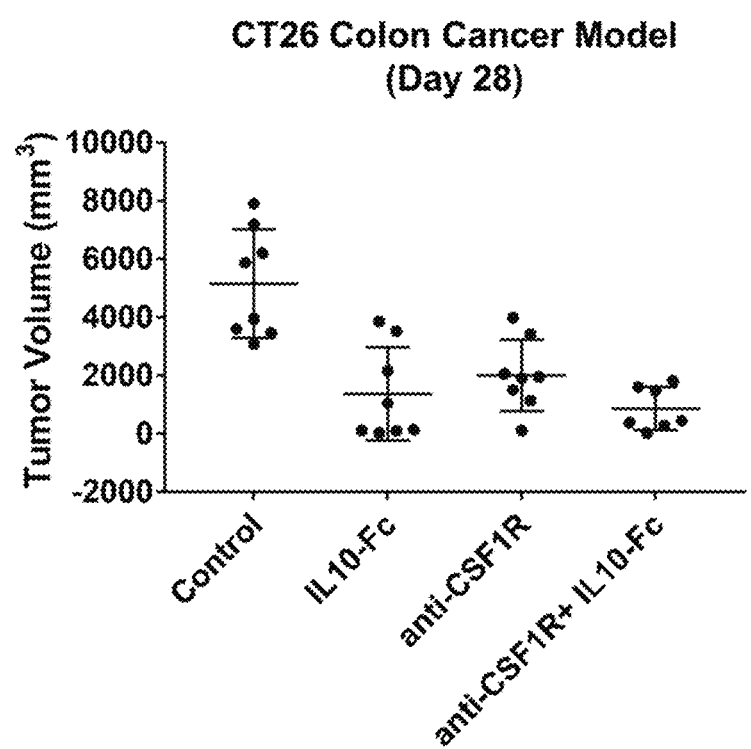
FIG. 7A and FIG. 7B depict plots showing that combination immunotherapy with anti-CSF1R antibody blockade and IL10 agonist acts to control tumor burden. CT26 tumors were randomized once tumors reached 50-100 mm³ 7 days post-implantation and then treated with isotype control (BioXcell, 30 mg/kg), anti-CSF1R (BioXcell, 30 mg/kg), IL10-Fc (20 mg/kg) or combination twice weekly for 3 weeks.
Figure 7B:
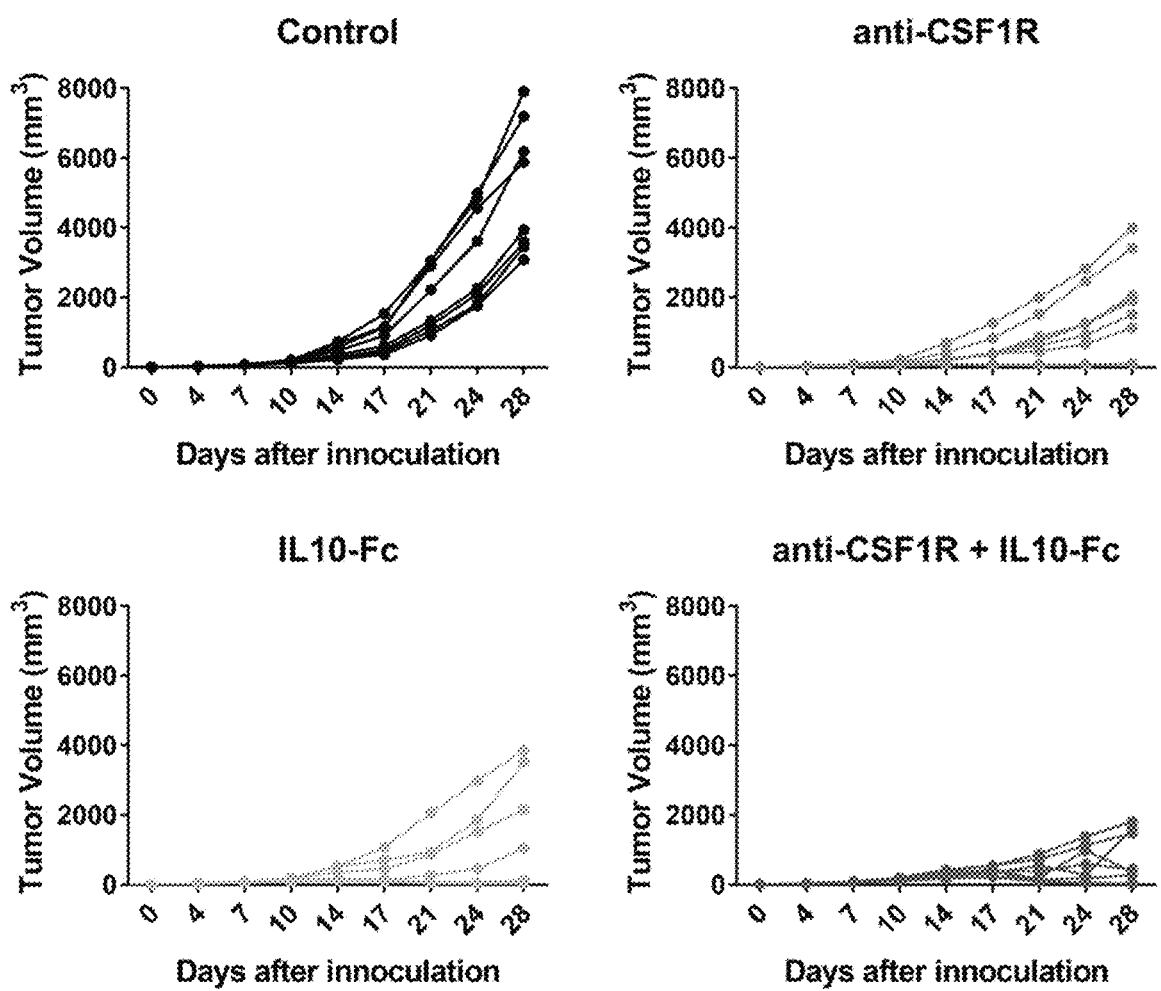
Figure 8A:
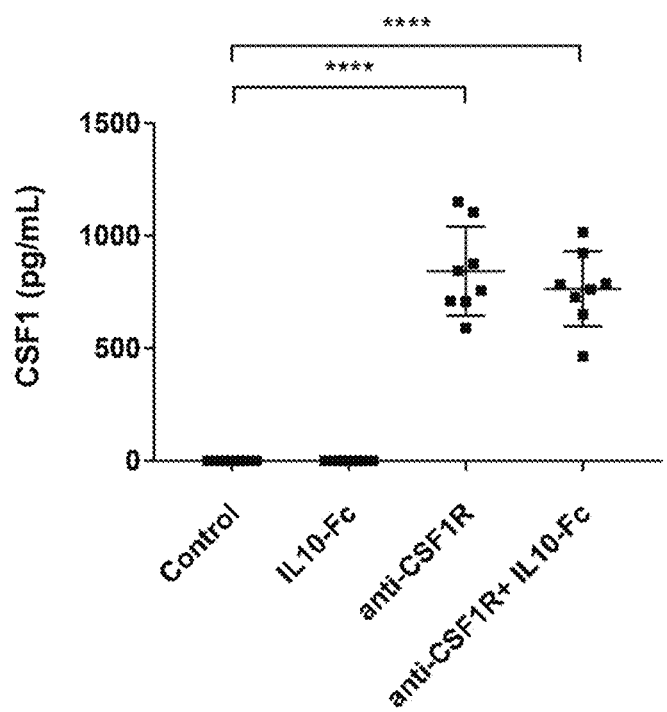
FIG. 8A, FIG. 8B, FIG. 8C and FIG. 8D depict plots showing cytokine levels related to CSF1R inhibition and IL10 function in syngeneic CT26 colon cancer model. Plasma levels of CSF1 (FIG. 8A), IL-34 (FIG. 8B), CXCL9 (FIG. 8C) in mice treated with anti-CSF1R or the IL10-Fc fusion protein for 1 week. Plasma level of IL-18 in mice treated with anti-CSF1R or IL10-Fc for 3 weeks (FIG. 8D).
Figure 8B:
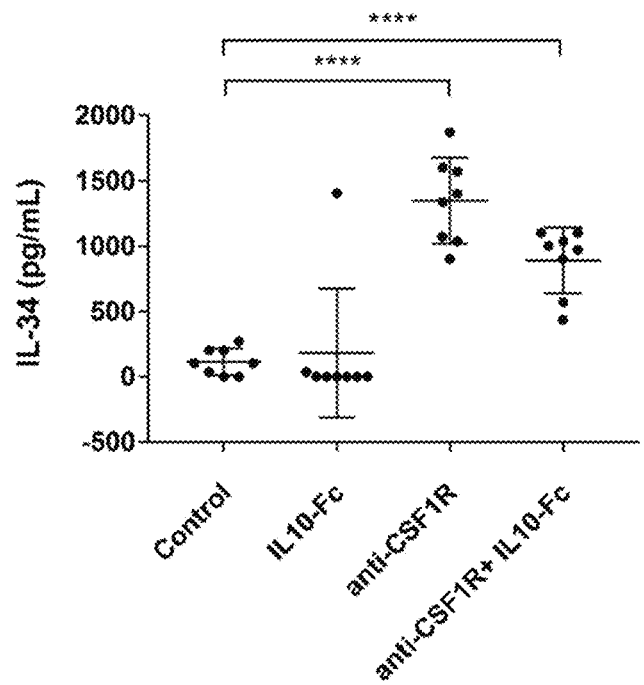
Figure 8C:
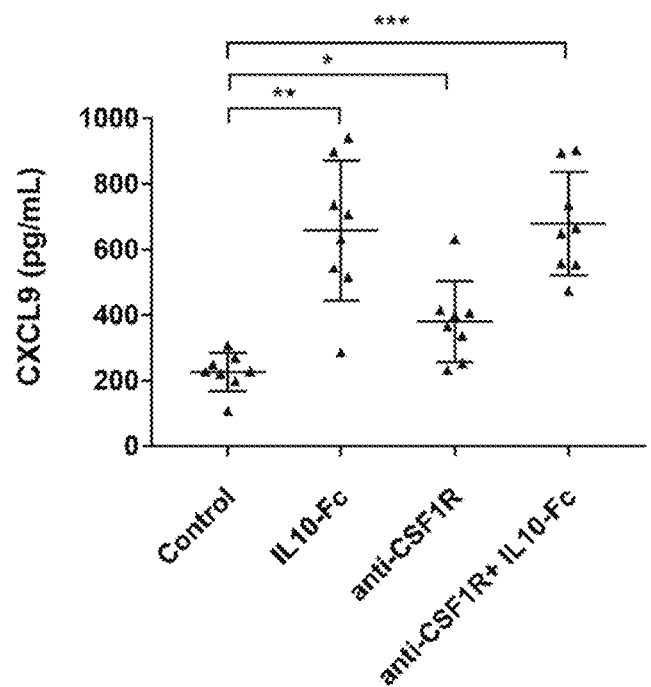
Figure 8D:
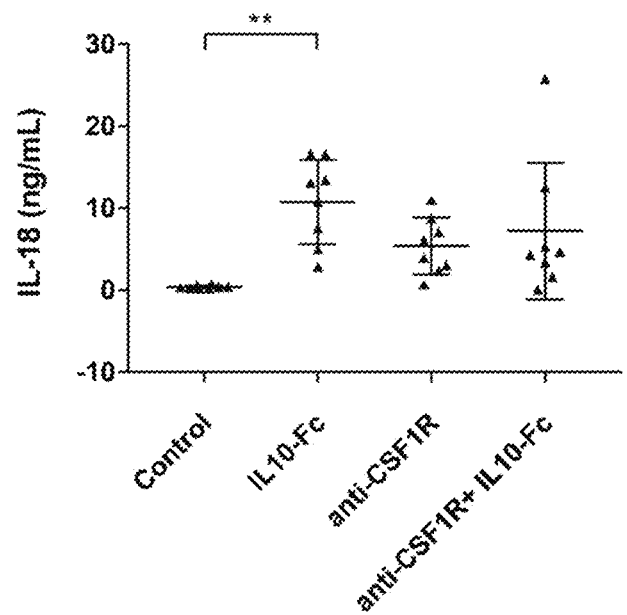

Results: As shown in FIG. 7A and FIG. 7B, the combination of the anti-CSF1R antibody blockade with the IL10 agonist acts to control tumor burden. Additionally, as shown by the plots depicted in FIG. 8A and FIG. 8B, the combination of the anti-CSF1R antibody blockade with the IL10 agonist act to maintain the cytokines levels related to CSF1R inhibition and IL10 agonist function in syngeneic CT26 colon cancer model.

C. Tumor-Infiltrated Immune Cell Analysis

For immunophenotypic analysis, tumors were excised at Day 14 and dissociated into single-cell suspensions. Tumor infiltrated cells were then stained with fluorescent-dye conjugated anti-CD45 (clone 30-F11, BD Biosciences), anti-CD3 (clone 500A2, BD Biosciences), anti-CD4 (clone RM4-5, BD Biosciences), anti-CD8 (clone 53-6.7, BD Biosciences), anti-F4/80 (clone T45-2342, BD Biosciences), anti-CD11b (clone M1/70, BD Biosciences), anti-Ly6C (clone AL-21, BD Biosciences), anti-Ly6G (clone 1A8, BD Biosciences) and PI (Sigma). After staining on ice for 30 min, cells were washed with FACS buffer and fixed by 2% paraformaldehyde. The fixed cells were further processed intracellular staining with fluorescent-dye conjugated anti-IFNγ (clone XMG1.2, BD Biosciences) at RT for 1 hr. After wash, the cells were analyzed on LSRFortessa (BD Biosciences).

Figure 9A:
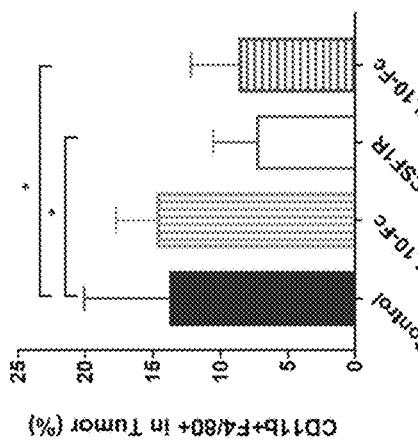
FIG. 9A, FIG. 9B, FIG. 9C, FIG. 9D, and FIG. 9E depict plots showing effect of treatment in a tumor-infiltrated immune cell analysis in a CT26 syngeneic tumor model. Syngeneic CT26 tumors were treated with isotype control, anti-CSF1R or IL10-Fc. After 7-day treatment, tumors were harvested and analyzed by flow cytometry. The percentage of TAMs (CD11b+F4/80+) (FIG. 9A), monocytic MDSCs (CD11b+Ly6C+) (FIG. 9B), granulocytic MDSCs (CD11b+Ly6G+) (FIG. 9C), activated CD4 T cells (CD4+IFNγ+) (FIG. 9D), activated CD8 T cells (CD8+IFNγ+) (FIG. 9E), in the tumor microenvironment were gated on CD45+ leukocytes. n=8 mice per group. Mean±SD is shown. *p<0.05, p<0.01, *p<0.001.
Figure 9C:
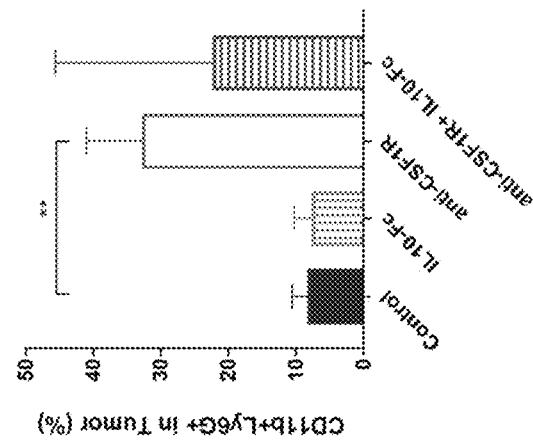
Figure 9B:
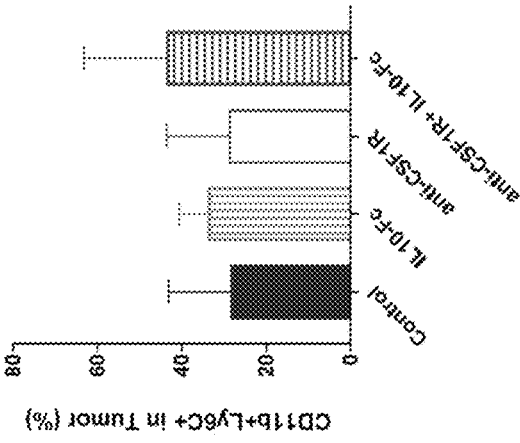
Figure 9D:
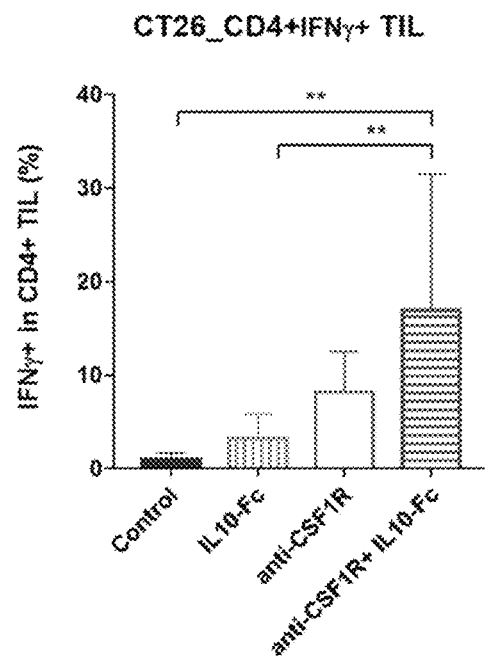
Figure 9E:
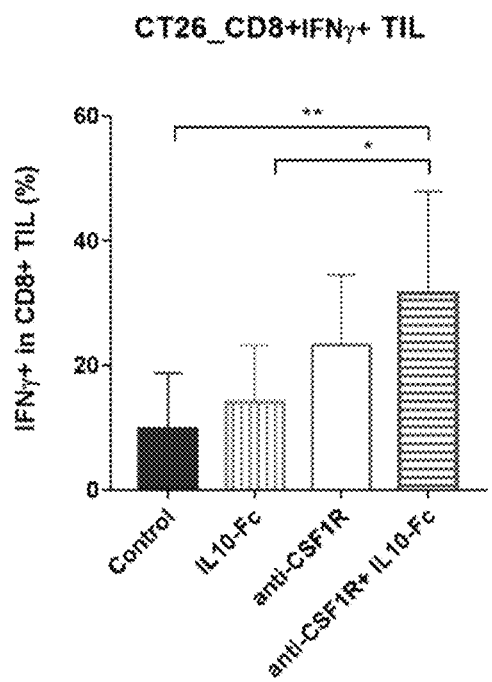

Results: As shown by the plots depicted in FIG. 9A-9C, the combination of the anti-CSF1R antibody and the IL10-Fc fusion agonist reduces the TAM population but not MDSC in the CT26 syngeneic tumor model. As shown by the plots depicted in FIG. 9D-9E, the combination increases activated tumor-infiltrated T cell population.

Example 5

Preparation and Functional Analysis of Anti-CSF1R/IL10 Fusion Proteins

This example illustrates studies in which exemplary anti-CSF1R/IL10 antibody fusions (or "fusion proteins") of the present disclosure are generated and functionally characterized.

A. Generation of Bifunctional Anti-CSF1R/IL10 Fusion Protein

Materials and methods: Recombinant IL10-Fc (SEQ ID NO: 73) and (IL10)$_2$-Fc (SEQ ID NO: 74) fusion proteins were prepared as described in Example 4 by genetically fusing IL10 to the N-terminus of the human IgG1-Fc separated by a 14 amino acid linker GGGGSGGGGSGGGG (SEQ ID NO: 78) and expressing in transfected ExpiCHO cells. Recombinant anti-CSF1R/IL10 fusions (or "fusion proteins") 6D4/IL10, 6M6/IL10, 6D4.hu22/IL10, 6D4.hu41/IL10, 6M6.hu12/IL10, and 6M6.hu41/IL10 were designed and prepared similarly by genetically fusing human IL10 to the C-terminus of the chimeric or humanized anti-CSF1R antibody V$_H$ domain (prepared as described in Examples 2 and 3) separated by the 14 amino acid linker (SEQ ID NO: 78). Additionally, surrogate anti-mouse CSF1R antibody ("AB98") was used to generate a surrogate mouse anti-CSF1R/IL10 fusion protein ("AB98/IL10"). The overall amino acid sequence design of the anti-CSF1R/IL10 fusion proteins are summarized in Table 3. The desired gene segments, preceded by an IL-2 secretion sequence required for secretion of recombinant proteins, were prepared by a commercial gene synthesis service (Thermo Scientific) and cloned into a mammalian expression vector. The anti-CSF1R/IL10 fusion protein constructs were expressed in transfected ExpiCHO cells.

B. Expression and Purification of Anti-CSF1R/IL10 Fusion Proteins

Materials and methods: Anti-CSF1R/IL10 fusion proteins were transiently expressed in ExpiCHO-S cells (Thermo Scientific). During exponential growing phage, 6×10$^6$ ExpiCHO-S cells were transiently transfected with 20 µg of the vectors encoding the Ab/IL10 fusion proteins by ExpiFectamine CHO Transfection Kit (Thermo Scientific). 18-22 hours after transfection, ExpiFectamine CHO Enhancer and ExpiCHO Feed were added to the flask. The cells were cultured for 8 days. The supernatant of each culture was centrifuged and subsequently filtered through a 0.45 µm filter.

The fusion proteins from the transfected cell supernatants were purified using Protein A Sepharose Fast Flow beads (GE Healthcare). Loaded columns were washed with 20 column volumes of PBS, and then eluted with 3 beads volume of 0.1 M Glycine (pH 2.5) directly into 1/10 volume of 1M Tris buffer (pH 9.0). Fusion protein containing fractions were pooled and dialyzed against PBS. The quality of purified anti-CSF1R/IL10 fusion proteins was examined by SDS-PAGE in the presence and absence of a reducing agent and stained with Coomassie blue.

Figures 10A, 10B, 10C:
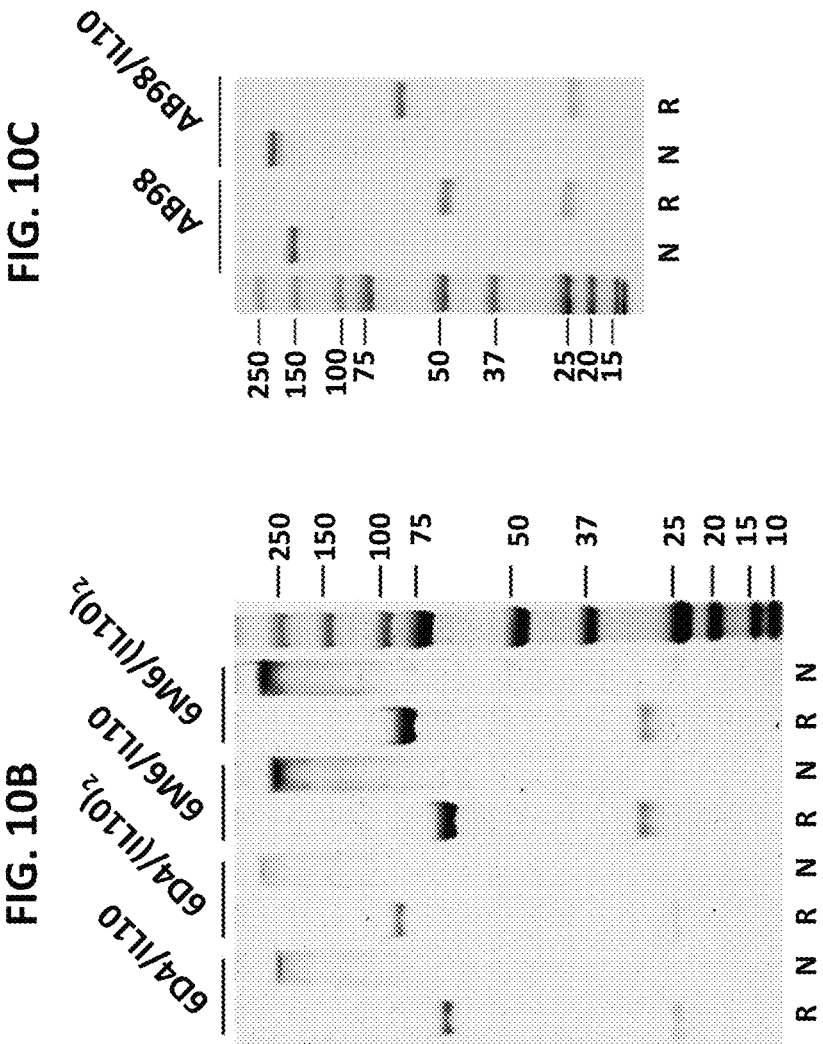
FIG. 10A, FIG. 10B, and FIG. 10C depict gel images illustrating the successful expression and purification of IgG/IL10 fusion proteins prepared as described in Example 5.

Results: Exemplary SDS-PAGE images confirming the purity of the IL10 fusion proteins, IL10-Fc and (IL10)$_2$-Fc and the anti-CSF1R/IL10 fusion proteins 6D4/IL10, 6D4/(IL10)$_2$, 6M6/IL10, and 6M6/(IL10)$_2$ are shown in FIGS. 10A and 10B, respectively. FIG. 10C shows the SDS-PAGE of a surrogate anti-mouse-CSF1R ("AB98") and corresponding "AB98/IL10" fusion protein.

C. CSF1R Specific ELISA

Materials and methods: Recombinant human CSF1R-Fc, or mouse CSF1R-Fc (Sino Biological) were immobilized on 96 well microtiter plate at a concentration of 1 µg/mL in Coating Solution (SeraCare) overnight at 4° C. The wells were washed with wash solution (0.05% Tween20 in imidazole-buffered saline) and blocked with 1% BSA. Serial dilutions of the anti-CSF1R/IL-10 fusion proteins were added to wells. After incubation at 37° C. for 1 h, the wells were washed with wash solution. To detect chimeric Ab/IL10 fusions, peroxidase-conjugated goat anti-human kappa light chain antibody (Bethyl) was applied to each well at 37° C. for 1 h incubation. To detect AB98 or AB98/IL10 fusions, peroxidase-conjugated Goat anti-mouse IgG Fab antibody (Jackson immunoresearch) was applied to each well at 37° C. for 1 h incubation. After washing, the wells were developed with TMB substrate for 5-10 min at RT and then stopped with 1 N HCl. Thereafter absorbance was measured at 450 nm and 650 nm.

Results: $EC_{50}$ values calculated through GraphPad Prism7 are shown in Table 11 (below).

TABLE 11

Binding activity of anti-CSF1R/
IL10 fusion protein to CSFIR

| Fusion protein | $EC_{50}$ (M) |
|---|---|
| hu-CSF1R binding | |
| 6D4/IL10 | $4.786 \times 10^{-10}$ |
| 6D4/(IL10)$_2$ | $3.930 \times 10^{-10}$ |
| 6D4.hu22/IL10 | $2.713 \times 10^{-10}$ |
| 6D4.hu41/IL10 | $2.203 \times 10^{-10}$ |
| 6M6/IL10 | $2.699 \times 10^{-10}$ |
| 6M6/(IL10)$_2$ | $2.321 \times 10^{-10}$ |
| 6M6.hu12/IL10 | $2.515 \times 10^{-10}$ |
| 6M6.hu41/IL10 | $2.049 \times 10^{-10}$ |
| mouse-CSF1R binding | |
| AB98 | $6.411 \times 10^{-10}$ |
| AB98/IL10 | $5.461 \times 10^{-10}$ |

D. Cellular Binding and Species Cross-Reactivity by Flow Cytometry

Materials and methods: The gene segments encoding full-length human CSF1R or cynomolgus CSF1R were obtained using Thermo gene synthesis service and cloned in a mammalian expression vector pCDNA3.4. Freestyle 293-F cells (Thermo Scientific) were transfected with CSF1R expression vector by polyethylenimine (PEI) method and selected with Geneticin (Thermo Scientific) to establish CSF1R stable cell lines. CSF1R-overexpressing 293F cells were incubated with serious dilutions of anti-CSF1R/IL10 fusion protein for 1 hr at 4° C. After washing with FACS buffer (2% FBS in PBS), the cells were stained with anti-human IgG-Alexa Fluor 647 and analyzed by Attune NxT Flow Cytometer (Thermo Scientific).

Figure 11A:
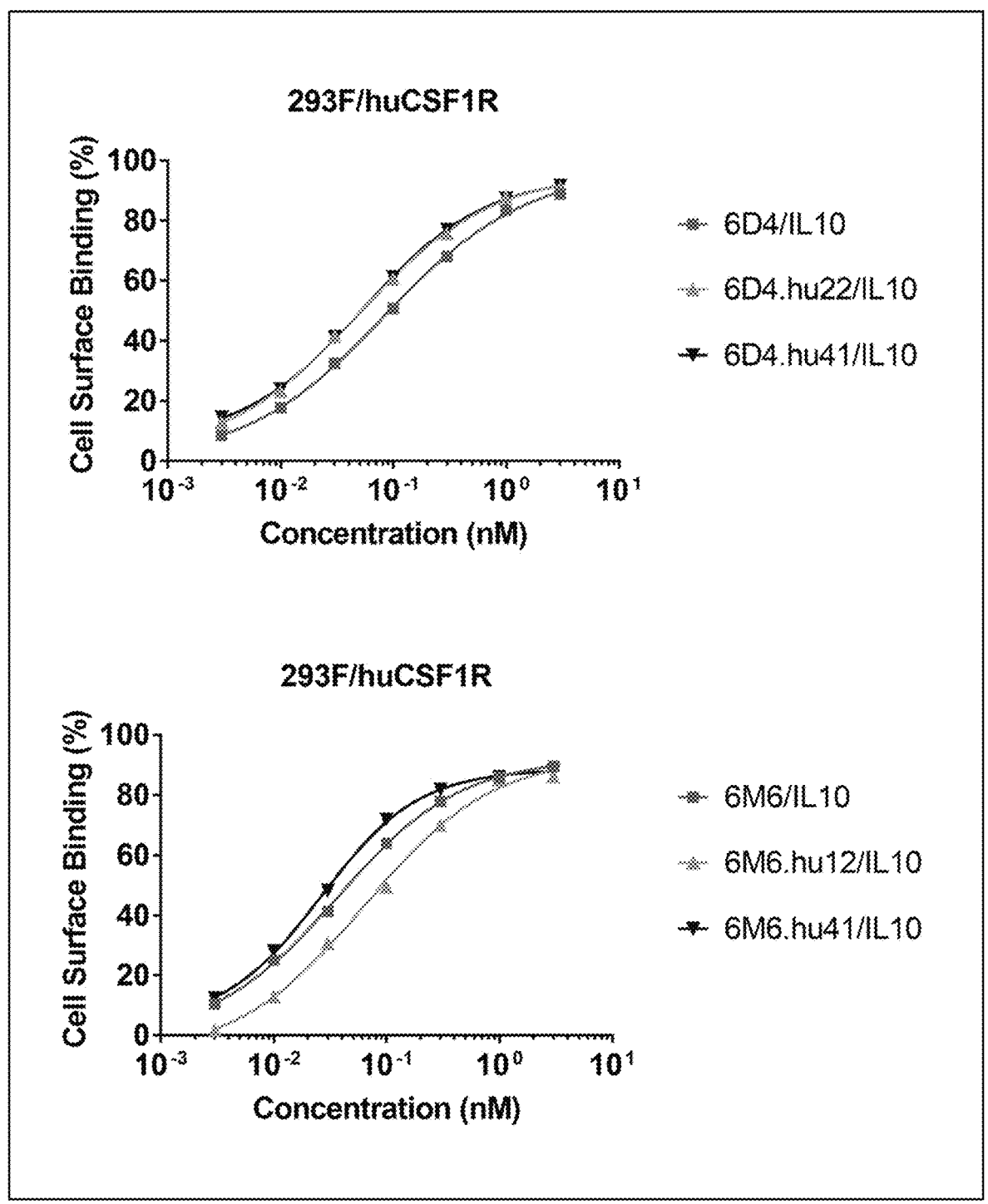
FIG. 11A and FIG. 11B depict plots of data determined as described in Example 5 showing the cross-species binding of the chimeric anti-CSF1R/IL10 fusion proteins ("6D4/IL10" and "6M6/IL10") and humanized anti-CSF1R/IL10 fusion proteins ("6D4.hu22/IL10," "6D4.hu41/IL10," "6M6.hu12/IL10," and "6M6.hu41/IL10") to 293F cells overexpressing human CSF1R ("huCSF1R") (FIG. 11A) or cynomolgus CSF1R ("cynoCSF1R") (FIG. 11B).
Figure 11B:
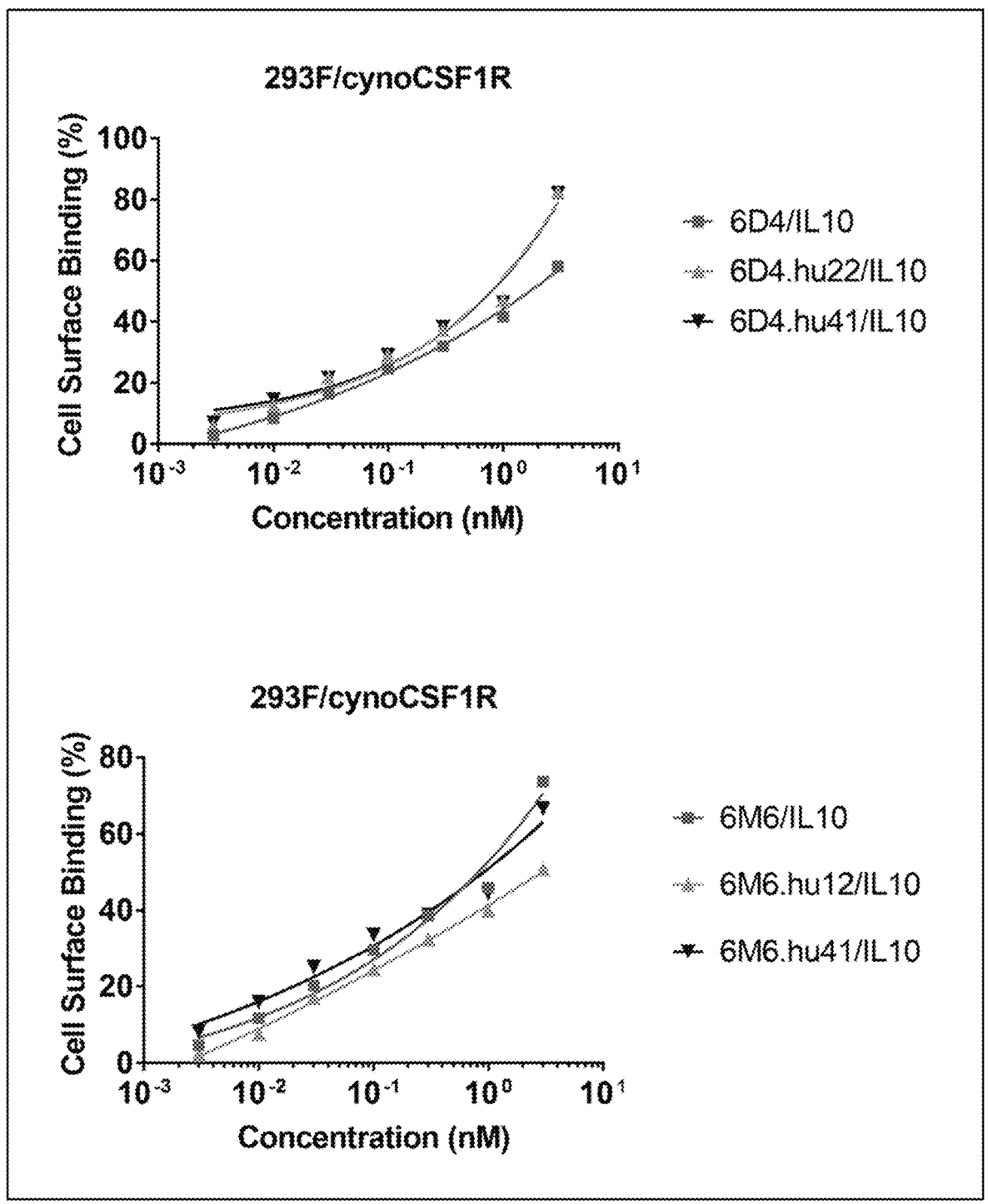

Results: As shown by the plots depicted in FIGS. 11A and 11B, the anti-CSF1R/IL10 fusion proteins were cross-reactive, recognizing both huCSF1R and cynoCSF1R expressed on 293F cells.

E. Inhibition of Ligand-Induced CSF1R Phosphorylation by Anti-CSF1R/IL10 Fusion Proteins Materials and methods: AML5 cells ($2 \times 10^6$) were incubated 5 min at RT with 1 μg/mL of control hIgG1, anti-CSF1R, IL10-Fc, or anti-CSF1R/IL10 fusion proteins. in 1 mL assay medium (MEMα containing Glutamax) for 5-10 min at RT. The cells were then incubated for 5 min at 37° C. with 50 ng/mL human CSF1 (R&D Systems). After the incubation, cells were then lysed, and total proteins were extracted. 50 jag proteins were analyzed by probing Western blots with antibodies against total CSF1R (Cell Signaling), phospho-CSF1R (Tyr723) (Cell Signaling), or β-actin (Cell Signaling).

Figure 12:
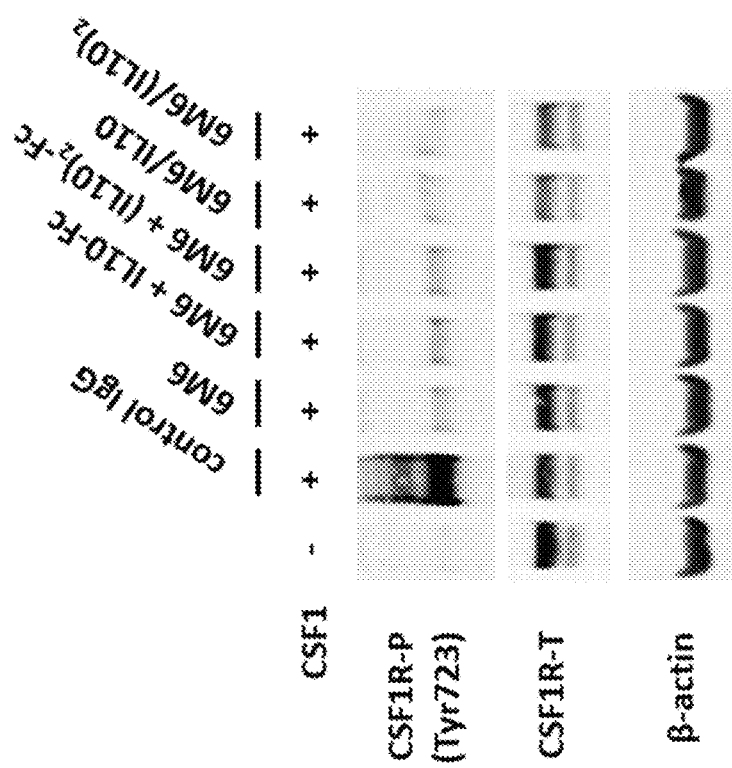
FIG. 12 depicts gel images obtained as described in Example 5 showing the attenuation of CSF1-induced CSF1R phosphorylation in AML5 cells in presence of control hIgG, anti-CSF1R 6M6, anti-CSF1R 6M6 plus IL10-Fc, anti-CSF1R plus $(IL10)_2$-Fc, or the anti-CSF1R/IL10 fusion proteins 6M6/IL10 or 6M6/$(IL10)_2$.

Results: As shown by Western blot images depicted in FIG. 12, the anti-CSF1R/IL10 fusion proteins, 6M6/IL10 and 6M6/(IL10)$_2$ attenuated the CSF1-mediated phosphorylation of CSF1R.

F. Inhibition of Ligand-Binding to CSF1R Using Competition ELISA

Materials and methods: Recombinant human CSF1R-Fc or mouse CSF1R-Fc (Sino Biological) fusion protein was immobilized on 96 well microtiter plate at a concentration of 1 μg/mL in Coating Solution (SeraCare) overnight at 4° C. The wells were washed with wash solution and blocked with 1% BSA at RT. Serial dilutions of Ab/IL-10 fusion proteins were added to wells. Then 2.5 ug/mL biotinylated human CSF1-His (Biolegend) or mouse CSF1-His (Sino Biological) was added and incubated for 1 h at 37° C. After washing, Streptavidin-HRP (Jackson ImmunoResearch) was applied to wells at RT for 1 h incubation. After washing, the wells were developed with TMB substrate for 5-10 min at RT and the stopped with 1 N HCl. Thereafter absorbance was measured at 450 nm and 650 nm. The $IC_{50}$ values were calculated through GraphPad Prism7.

Results: As shown in Table 2, the anti-CSF1R/IL10 fusions exhibited blocking activity against the ligand, CSF1 binding to its cognate receptor, CSF1R.

TABLE 12

Blocking activity of anti-CSF1R/IL10 fusion
protein to interaction of CSF1R and CSF1

| | Fusion Protein | $IC_{50}$ (M) |
|---|---|---|
| Human CSF1 to human CSF1R | 6D4/IL10 | $1.4 \times 10^{-9}$ |
| | 6M6/IL10 | $4.81 \times 10^{-10}$ |
| Mouse CSF1 to mouse CSF1R | AB98 | $8.25 \times 10^{-10}$ |
| | AB98/IL10 | $7.08 \times 10^{-10}$ |

G. IL10RA Specific ELISA

Materials and methods: Recombinant human IL-10Ra fusion protein (R&D Systems) were immobilized on 96 well microtiter plate at a concentration of 1 μg/ml in Coating Solution (SeraCare) overnight at 4° C. The wells were washed with wash solution (0.05% Tween20 in imidazole-buffered saline) and blocked with 1% BSA. Serial dilutions of Ab/IL-10 fusion proteins were added to wells. After incubation at 37° C. for 1 hr, the wells were washed with wash solution. Peroxidase-conjugated goat anti-human kappa light chain antibody (Bethyl) was applied to each well at 37° C. for 1 hr incubation. After washing, the wells were developed with TMB substrate for 5-10 min at RT and then stopped with 1 N HCl. Thereafter absorbance was measured at 450 nm and 650 nm. The EC50 value was calculated through GraphPad Prism7.

Results: $EC_{50}$ values calculated through GraphPad Prism7 are shown in Table 13 (below).

TABLE 13

Binding activity of anti-CSF1R/
IL10 fusion proteins to IL10R

| | $EC_{50}$ (M) |
|---|---|
| IL10-Fc | $3.847 \times 10^{-9}$ |
| (IL10)$_2$-Fc | $7.236 \times 10^{-9}$ |
| 6D4/IL10 | $2.764 \times 10^{-9}$ |
| 6D4/(IL10)$_2$ | $6.076 \times 10^{-9}$ |
| 6M6/IL10 | $2.752 \times 10^{-9}$ |
| 6M6/(IL10)$_2$ | $9.355 \times 10^{-9}$ |
| AB98/IL10 | $2.472 \times 10^{-8}$ |

H. Inhibition of Ligand-Dependent AML5 Cell Proliferation by Anti-CSF1R/IL10 Fusion Proteins Materials and methods: AML-5 cells ($1.5 \times 10^4$ per well) were incubated with serious dilutions of Ab/IL10 fusion protein in assay medium (MEMα containing Glutamax without FBS) in 96-well plate. human CSF-1 (20 ng/mL) was then added to seeded cells for 72 hours stimulation. AML-5 cell proliferation was measured using CellTiter-Glo assay (Promega).

Figure 13A:
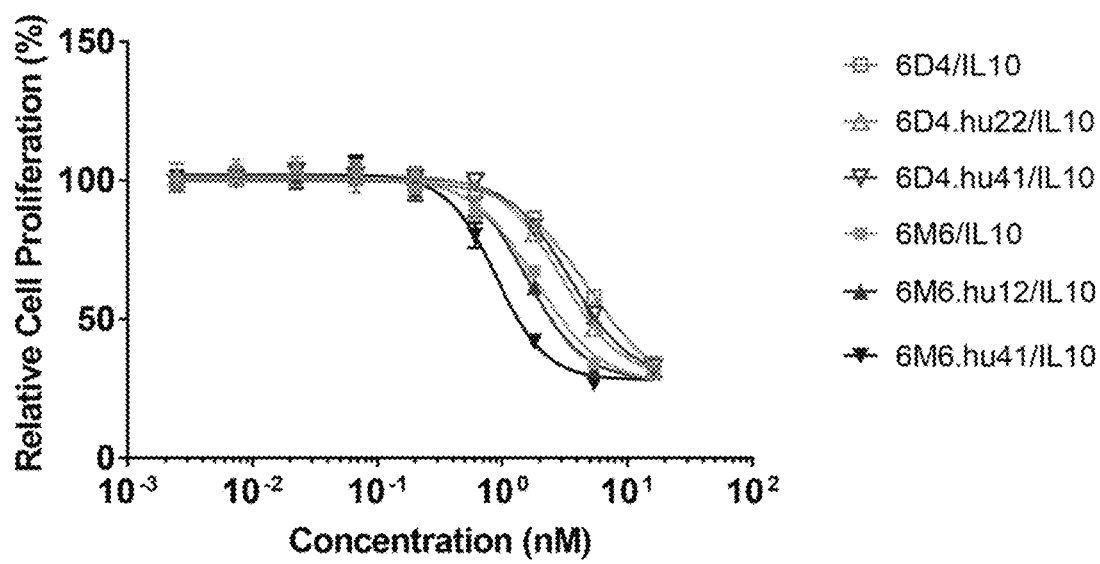
FIG. 13A, FIG. 13B, FIG. 13C, and FIG. 13D depict plots of data obtained as described in Example 5 showing the inhibition of CSF1-dependent cell proliferation in presence of anti-CSF1R/IL10 fusion proteins.

Results: As shown by the plot depicted in FIG. 13A, the anti-CSF1R/IL10 antibody fusions 6D4/IL10, 6D4.hu22/IL10, 6D4.hu41/IL10, 6M6/IL10, 6M6.hu12/IL10, and 6M6.hu41/IL10, were all capable of inhibiting CSF1-dependent cell proliferation. $IC_{50}$ values determined from the plots are shown in Table 14 below.

TABLE 14

Inhibition of AML5 cell proliferation

| Antibody | $IC_{50}$ (M) |
|---|---|
| 6D4/IL10 | $4.92 \times 10^{-9}$ |
| 6D4.hu22/IL10 | $2.98 \times 10^{-9}$ |
| 6D4.hu41/IL10 | $3.46 \times 10^{-9}$ |
| 6M6/IL10 | $1.87 \times 10^{-9}$ |
| 6M6.hu12/IL10 | $1.61 \times 10^{-9}$ |
| 6M6.hu41/IL10 | $8.93 \times 10^{-10}$ |

I. Inhibition of CSF1-Dependent Cell Survival of CD14+ Monocytes and Macrophages by Anti-CSF1/IL10 Fusion Proteins Materials and methods: Human PBMC were immediately isolated by density gradient centrifugation using Ficoll-Paque Plus (GE Healthcare). CD14+ monocytes were isolated by using anti-human CD14 conjugated magnetic beads (Miltenyi Biotec). In the cell survival assay, CD14+ monocytes ($1 \times 10^4$ per well) were incubated with serious dilutions of anti-CSF1R or Ab/IL10 fusion proteins in culture medium (RPMI1640 containing 10% FBS) in 96-well plate. CSF1 (100 ng/mL) was then added to cells. Cell survival was measured 6 days post stimulation using CellTiter-Glo assay.

To generate monocyte derived macrophages, human CD14+ monocytes were cultured at $2 \times 10^6$ cells/mL in RPMI1640 supplemented with 10% FBS and 100 ng/mL CSF1 for 6 days. In the proliferation assay, differentiated macrophages ($2 \times 10^4$ per well) were incubated with serious dilutions of anti-CSF1R or Ab/IL10 fusion proteins in culture medium (RPMI1640 containing 10% FBS) in 96-well plate. CSF1 (10 ng/mL) was then added to cells. Cell survival was measured 72 hours post stimulation using CellTiter-Glo assay.

Figure 13B:
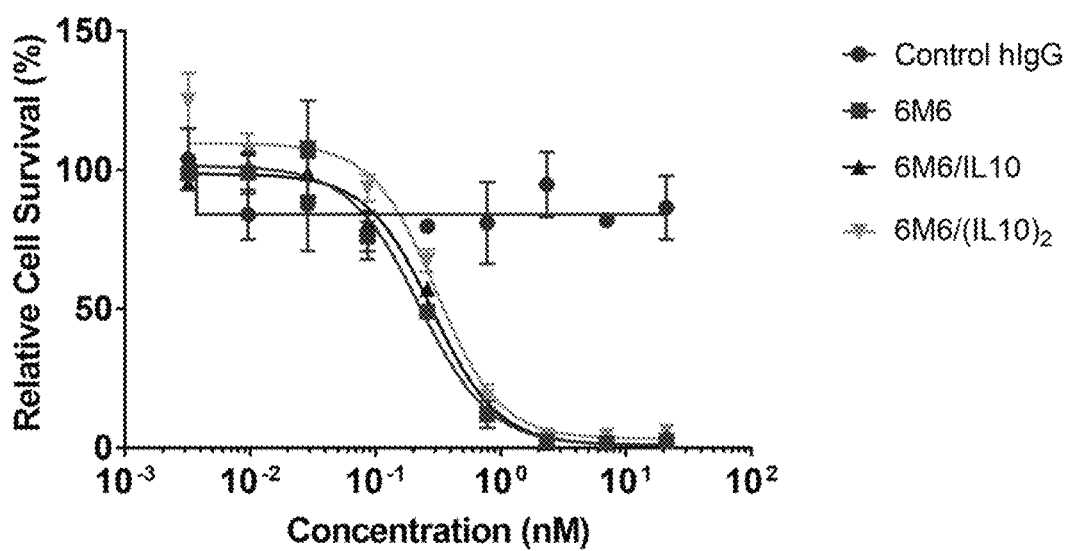
Figure 13C:
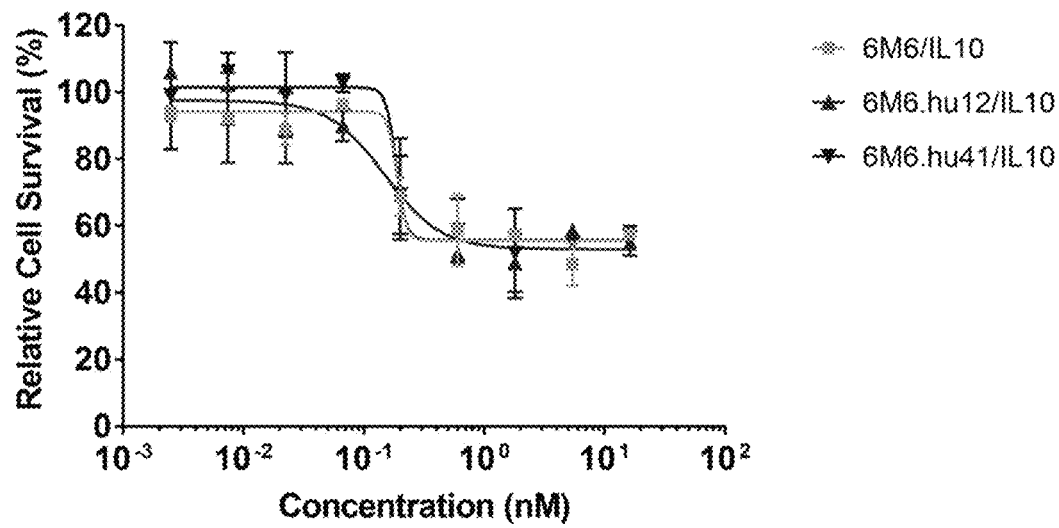

Results: As shown by the plots depicted in FIGS. 13B and 13C the anti-CSF1R/IL10 antibody fusions 6M6/IL10, 6M6/(IL10)$_2$, 6M6.hu12/IL10, and 6M6.hu41/IL10, were all capable of inhibiting CSF1-dependent CD14+ monocyte and macrophage survival. $IC_{50}$ values determined from the plots are shown in Table 15 below.

TABLE 15

| Antibody | $IC_{50}$ (M) |
|---|---|
| Inhibition of CD14 + monocyte survival | |
| 6M6 | $2.24 \times 10^{-10}$ |
| 6M6/IL10 | $2.82 \times 10^{-10}$ |
| 6M6/(IL10)$_2$ | $3005 \times 10^{-10}$ |
| Inhibition of macrophage survival | |
| 6M6/IL10 | $1.89 \times 10^{-10}$ |
| 6M6.hu12/IL10 | $1.49 \times 10^{-10}$ |
| 6M6.hu41/IL10 | $1.84 \times 10^{-10}$ |

J. Inhibition of Ligand-Dependent M-NFS-60 Cell Proliferation by a Surrogate Mouse Anti-CSF1R Antibody, AB98

Materials and methods: M-NFS-60 murine myelogenous leukemia cells (ATCC CRL-1838) ($2 \times 10^3$ per well) were incubated with serious dilutions of anti-mouse CSF1R (AB98) or anti-mouse CSF1R/IL10 fusion protein (AB98/IL10) in assay medium (RPMI1640 containing 10% FBS and 0.05 mM (β-ME) in 96-well plate. human CSF1 (20 ng/mL) was then added to seeded cells for 72 hours stimulation. M-NFS-60 cell proliferation was measured using CellTiter-Glo assay (Promega).

Figure 13D:
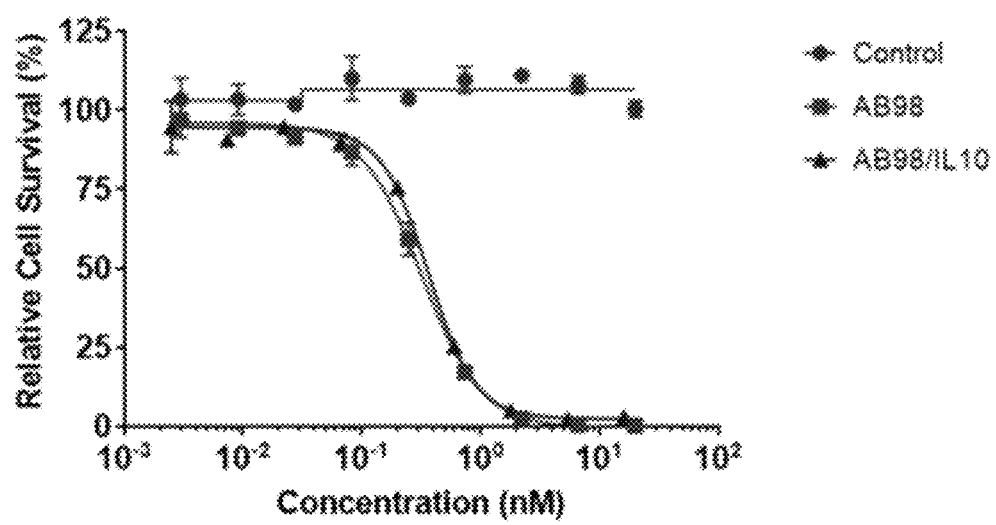

Results: As shown by the plot depicted in FIG. 13D, the surrogate mouse anti-CSF1R, AB98, anti-CSF1R/IL10 fusion protein AB98/IL10 was also capable of inhibiting CSF1-dependent M-NFS-60 cell proliferation. $IC_{50}$ values determined from the plots are shown in Table 16 below.

TABLE 16

Inhibition of M-NFS-60 cell proliferation

| Antibody | $IC_{50}$ (M) |
|---|---|
| AB98 | $0.32 \times 10^{-9}$ |
| AB98/IL10 | $0.36 \times 10^{-9}$ |

K. Stimulation of MC/9 Cell Proliferation by IL10

Materials and methods: The biological activity of IL10 was determined by using a proliferation assay. MC/9 (ATCC, CRL-8306) murine mast cells were cultured in DMEM (GIBCO) supplemented with 2 mM L-glutamine, 0.05 mM 2-mercaptoethanol, 10% Rat T-STIM (Becton Dickenson) and 10% FBS. In the proliferation assay, MC/9 cells were plated in 96-well plate at $1 \times 10^4$ per well in 200 μL, of assay medium (DMEM containing 10% FBS) in the presence of IL10-Fc or Ab/IL10 fusion protein. After 72 hours stimulation. MC/9 cell proliferation was measured using CellTiter-Glo assay.

Figure 14A:
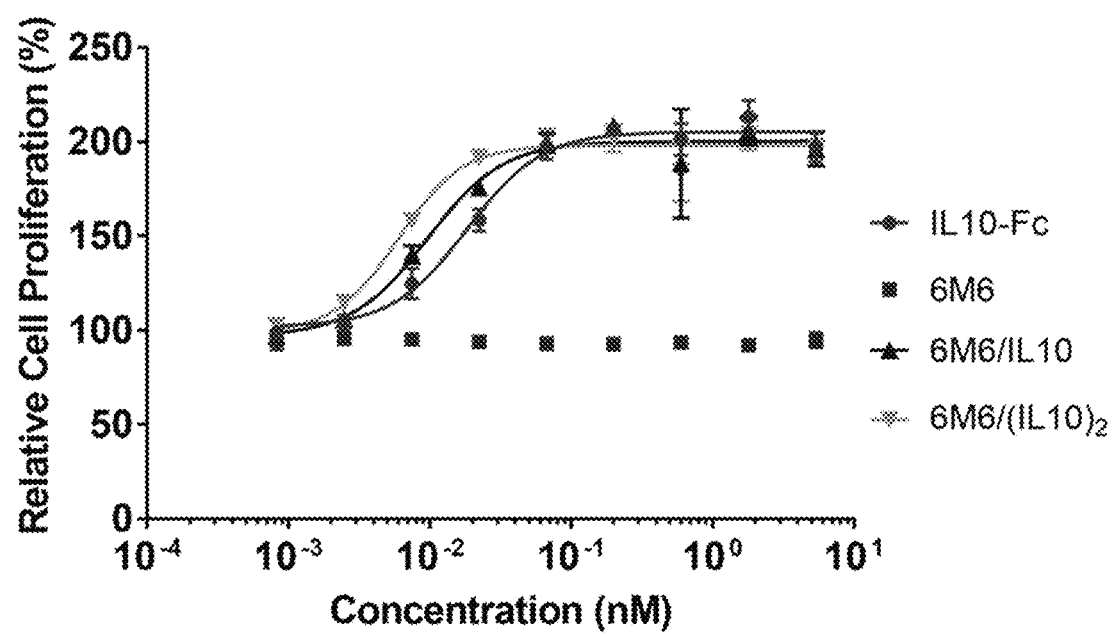
FIG. 14A and FIG. 14B depict plots of data obtained as described in Example 5 showing the induction of MC/9 cell proliferation by anti-CSF1R/IL10 fusion proteins. MC/9 cells were co-cultured for 3 days with IL10-Fc and chimeric anti-CSF1R/IL10 fusion proteins (FIG. 14A), or humanized anti-CSF1R/IL10 fusion proteins (FIG. 14B). Cell proliferation was measured by CellTiter-Glo assay.
Figure 14B:
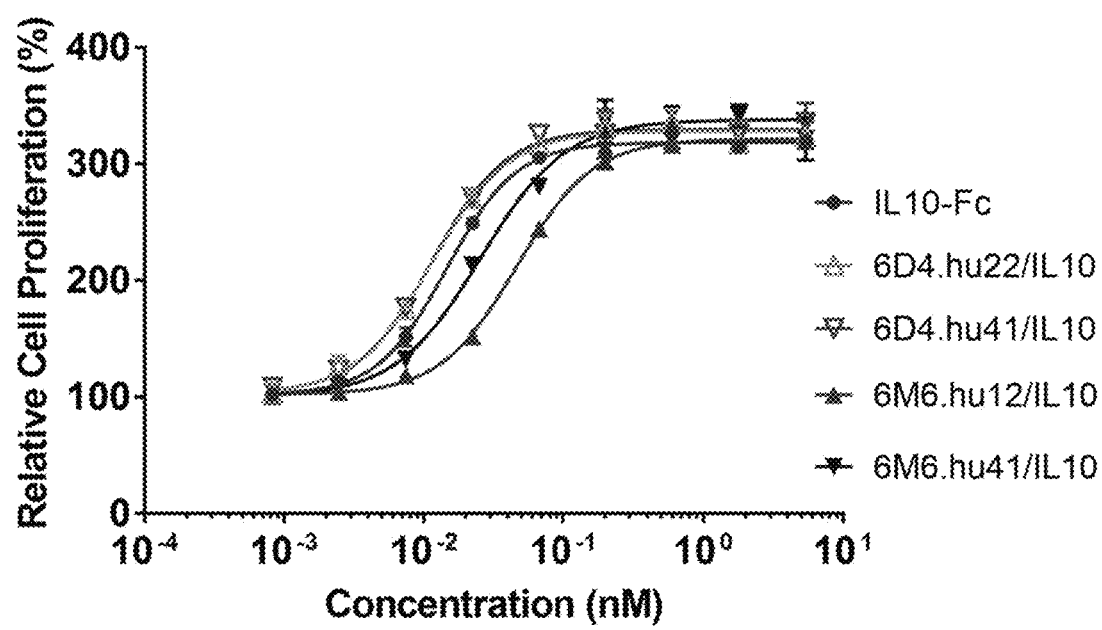

Results: As shown by the plots depicted in FIGS. 14A and 14B the anti-CSF1R antibody fusions 6M6/IL10, 6M6/(IL10)$_2$, 6D4.hu22/IL10, 6D4.hu41/IL10, 6M6.hu12/IL10, and 6M6.hu41/IL10 were capable of inducing MC/9 cell proliferation. $EC_{50}$ values determined from the plots are shown in Table 17 below.

TABLE 17

Induced MC/9 proliferation

| Antibody | $EC_{50}$ (M) |
|---|---|
| IL10-Fc | $1.82 \times 10^{-11}$ |
| 6M6/IL10 | $9.56 \times 10^{-12}$ |
| 6M6/(IL10)$_2$ | $5.96 \times 10^{-12}$ |
| 6D4.hu22/IL10 | $1.14 \times 10^{-11}$ |
| 6D4.hu41/IL10 | $1.14 \times 10^{-11}$ |
| 6M6.hu12/IL10 | $4.60 \times 10^{-11}$ |
| 6M6.hu41/IL10 | $2.54 \times 10^{-11}$ |

L. Activation of CD8 T Cells by IL10

Materials and methods: Human CD8 T cells were isolated from PBMCs by using CD8 magnetic beads (Miltenyi Biotec). Isolated CD8 T cells ($1 \times 10^7$ cells/3 mL/well of a 6-well plate) were culture in AIM-V medium (Thermo Scientific) and activated with T Cell TransAct (Miltenyi Biotec) for 3 days. Following activation, CD8 T cells were then washed and plated ($4 \times 10^5$ cells per well) in a 96-well plate and treated with Ab/IL-10 fusion proteins for 3 days. Following treatment with Ab/IL-10 fusion protein, cells were re-stimulated with 1 μg/mL soluble anti-CD3 (Biolegend) for 4 h. Concentrations of IFN-γ and granzyme B in cell culture media were measured by ELISA (Biolegend) according to the manufacturer's instructions.

Figure 15A:
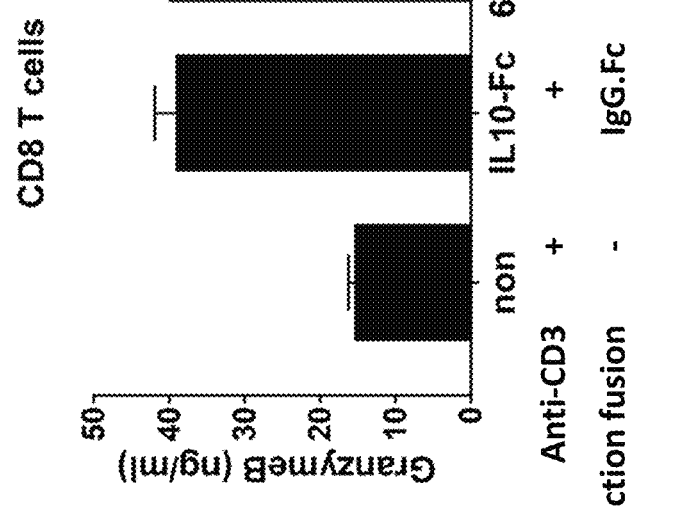
FIG. 15A, FIG. 15B, FIG. 15C, and FIG. 15D depict plots of data obtained as described in Example 5 showing the potentiation of IFNγ and granzyme B production from CD8 T cells activated with anti-CD3 and anti-CD28 for 3 days by anti-CSF1R/IL10 fusion proteins. Activated CD8 T cells were treated for 3 days with IL10-Fc (FIG. 15A, FIG. 15B) or anti-CSF1R/IL10 fusion proteins (FIG. 15C, FIG. 15D) and triggered with anti-CD3 for 4 hours. Level of IFNγ(FIG. 15A, FIG. 15C) and cytotoxic protein granzyme B (FIG. 15B, FIG. 15D) were measured by ELISA.
Figure 15B:
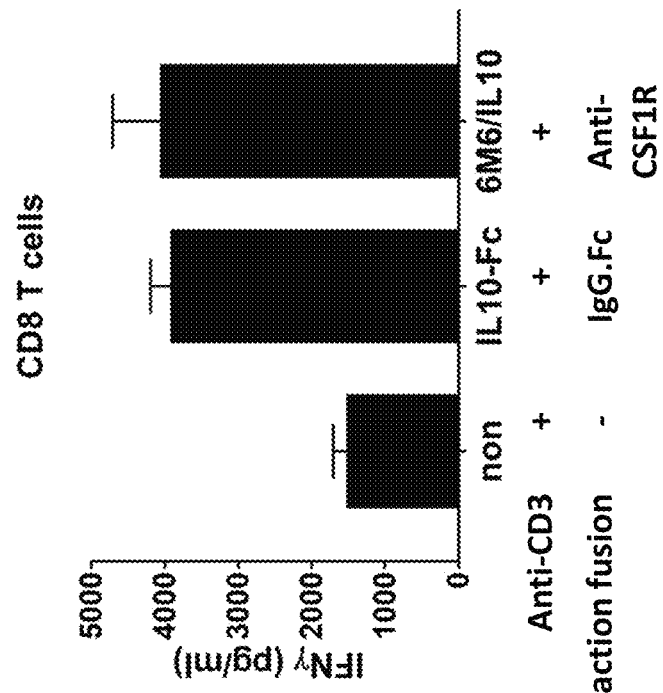
Figure 15C:
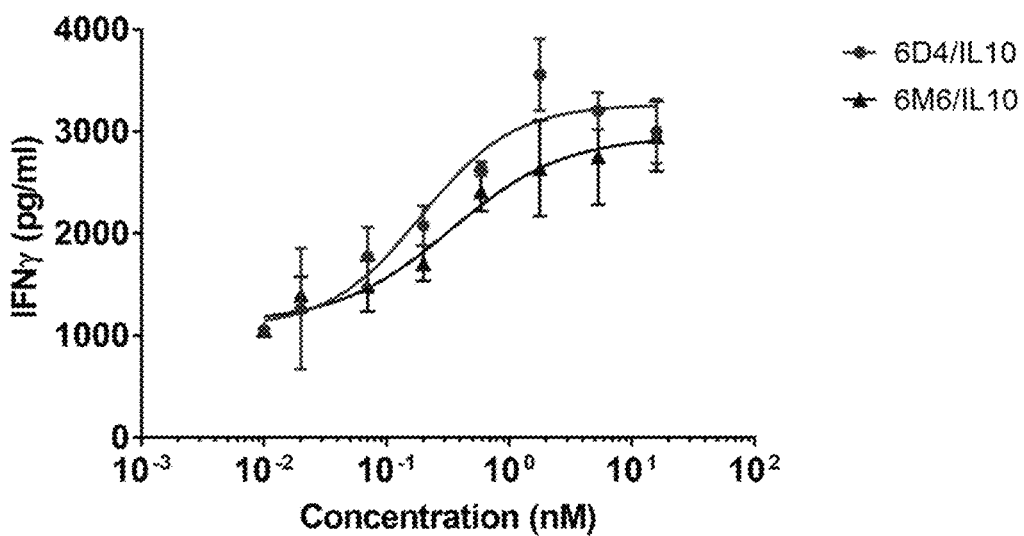
Figure 15D:
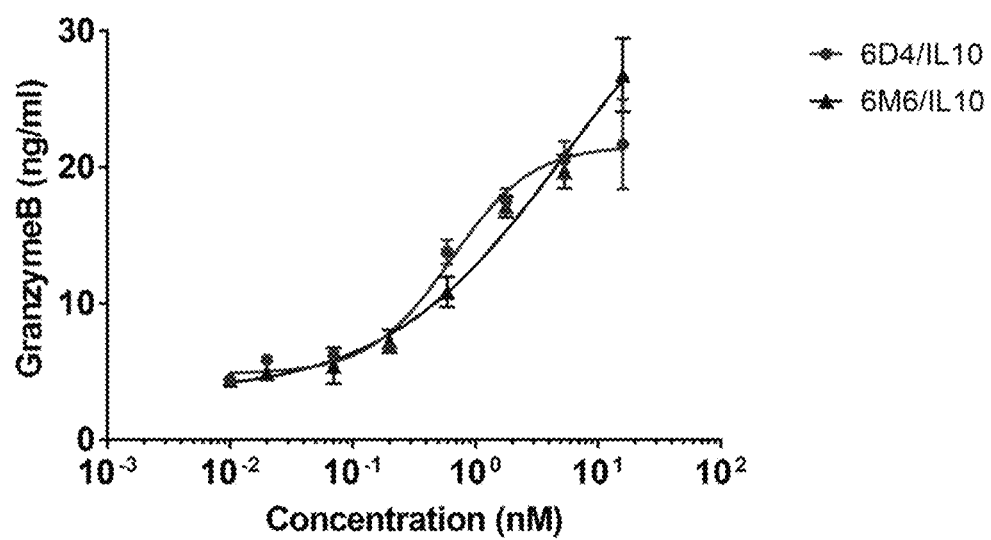
Figure 16:
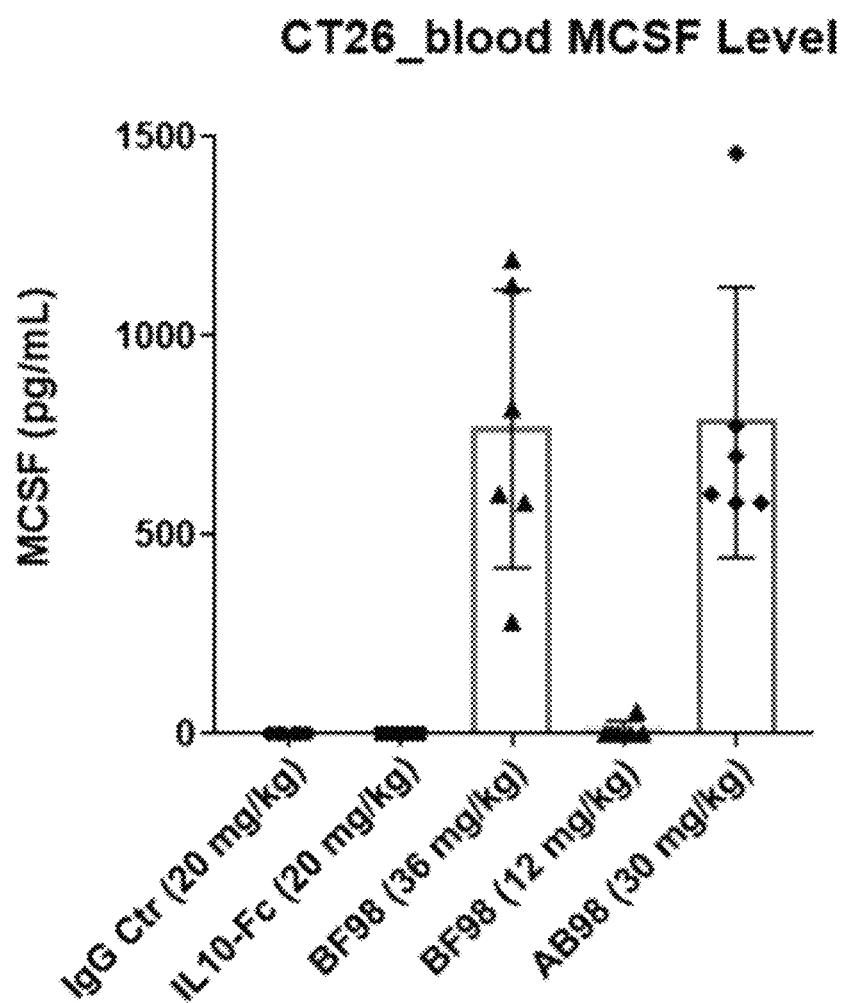
FIG. 16 depicts a plot showing cytokine levels related to CSF1R inhibition and IL-10 function in syngeneic CT26 colon cancer model. Plasma level of CSF1 in mice treated with anti-CSF1R IL10-Fc, or anti-CSF1R/IL10 for 1 weeks. n=6 mice per group. Mean±SD is shown. *$p<0.05$.

Results: As shown by the plots depicted in FIGS. 15A, 15B, 15C, and 15D anti-CSF1R antibody fusions with IL10 are capable of potentiating the production of IFNγ and granzyme B from activated CD8 T-cells. $EC_{50}$ values determined from the plots of FIGS. 15C and 15D are shown in Table 18 below.

TABLE 18

| Antibody Fusion | $EC_{50}$ (M) |
|---|---|
| Induced IFNγ production | |
| 6D4/IL10 | $1.91 \times 10^{-10}$ |
| 6M6/IL10 | $3.36 \times 10^{-10}$ |
| Induced granzyme B production | |
| 6D4/IL10 | $6.35 \times 10^{-10}$ |
| 6D4/IL10 | $5.61 \times 10^{-9}$ |

M. Tumor-Infiltrated Immune Cell Analysis in CT26 Tumor Model

Materials and methods: BALB/c mice (6-8 weeks old, female) were implanted subcutaneously with $5 \times 10^5$ CT26.WT cells (ATCC CRL-2638). Mice were randomized at Day7 into treatment groups when tumor volume reached 50-100 mm³. Mice were then injected intraperitoneally twice weekly with 20 mg/kg human IgG1 Fc control (BioXcell), 20 mg/kg IL10-Fc, 30 mg/kg anti-CSF1R AB98, 12 or 36 mg/kg anti-CSF1R/IL10 fusion protein (AB98/IL10). After two times of treatment, whole blood and tumor were harvested for immunophenotypic analysis at Day14. Tumors were dissociated into single-cell suspensions. Blood cells and tumor infiltrated cells were then stained on ice for 30 min with fluorescent-dye conjugated anti-CD45 (clone 30-F11, BD Biosciences), anti-CD3 (clone 500A2, BD Biosciences), anti-CD4 (clone RM4-5, BD Biosciences), anti-CD8 (clone 53-6.7, BD Biosciences), anti-F4/80 (clone T45-2342, BD Biosciences), anti-CD11b (clone M1/70, BD Biosciences), anti-Ly6C (clone AL-21, BD Biosciences), anti-Ly6G (clone 1A8, BD Biosciences), anti-LAG3 (clone C9B7W, BD Biosciences), anti-PD1 (clone RMP1-30, BD Biosciences) and PI (Sigma). After wash, the cells were analyzed on LSRFortessa (BD Biosciences).

The blood samples were collected weekly. Concentration of mouse CSF1 was measured by ELISA kits (Biolegend).

Figure 17B:
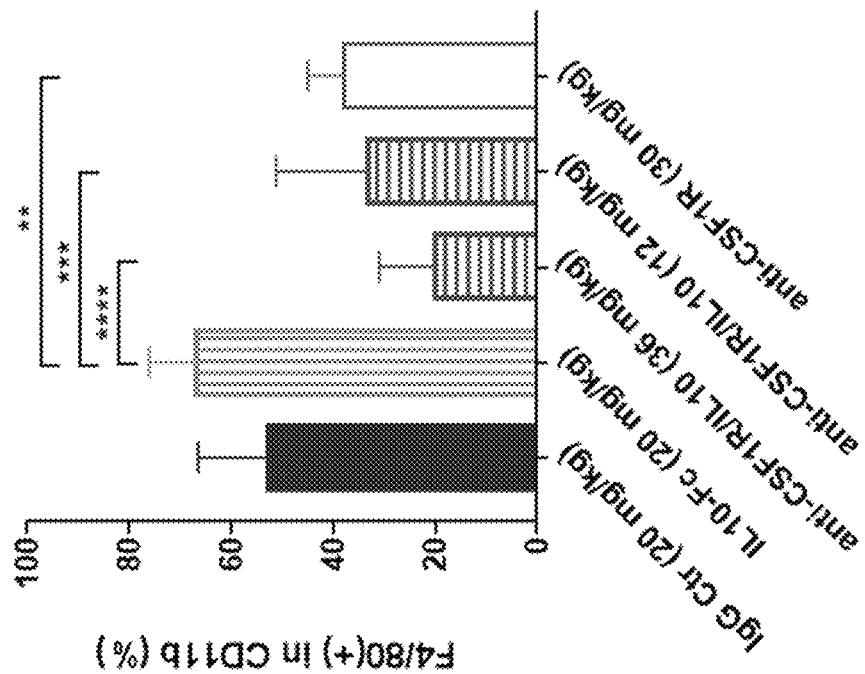
Figure 17A:
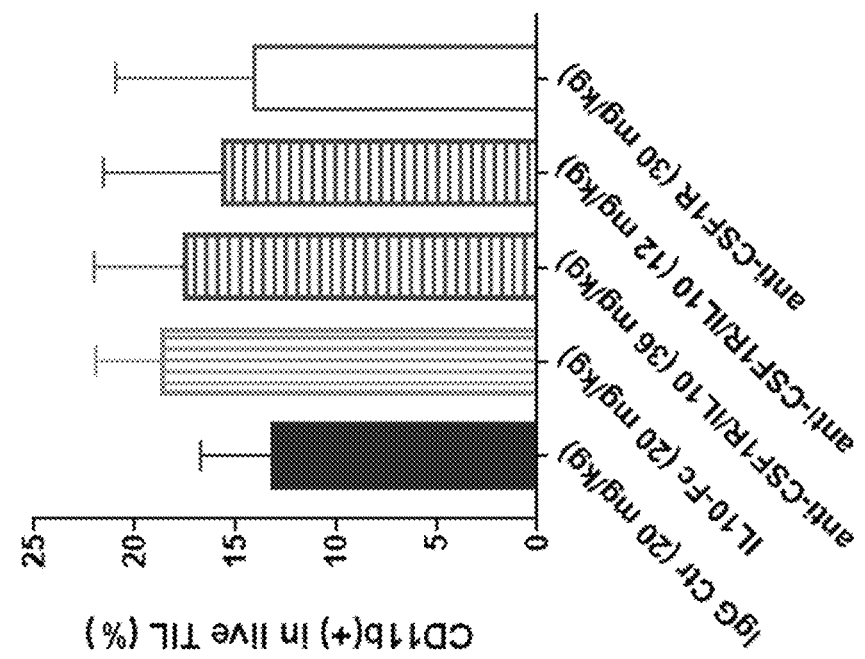
Figure 18A:
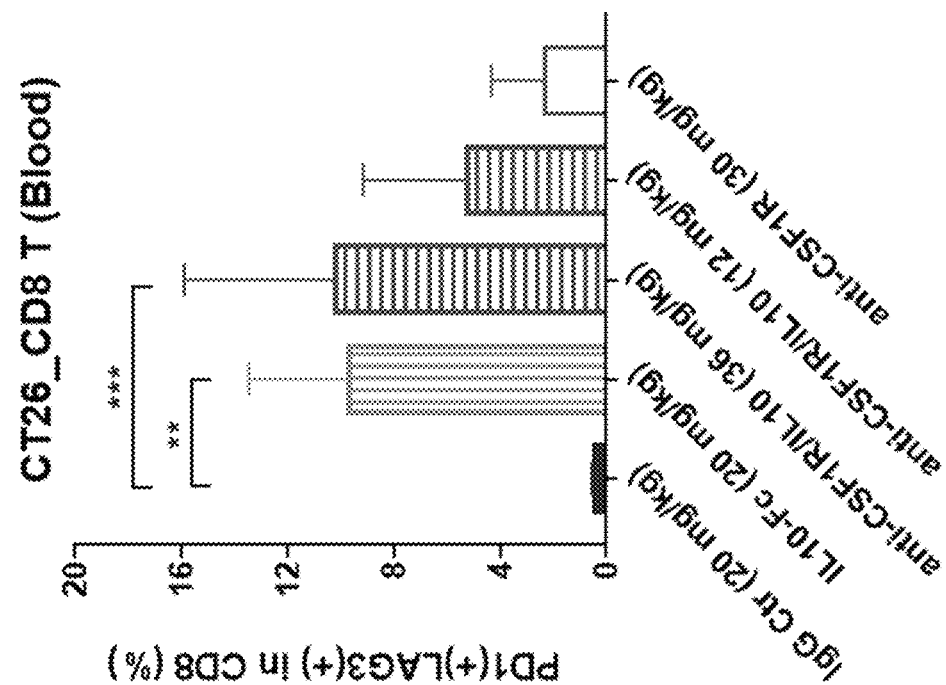
FIG. 18A and FIG. 18B depict plots showing results of blood T cell analysis in CT26 syngeneic tumor model. Syngeneic CT26 tumors were treated with isotype control, IL10-Fc, surrogate anti-CSF1R or anti-CSF1R/IL10. After 7-days treatment, blood was harvested and analyzed by flow cytometry. The percentage of total CD8+ T cells (FIG. 18A), or CD8+LAG3+PD1+(FIG. 18B), were gated on CD3+ leukocytes. n=6 mice per group. Mean±SD is shown. *$p<0.05$, $p<0.01$, *$p<0.001$.
Figure 18B:
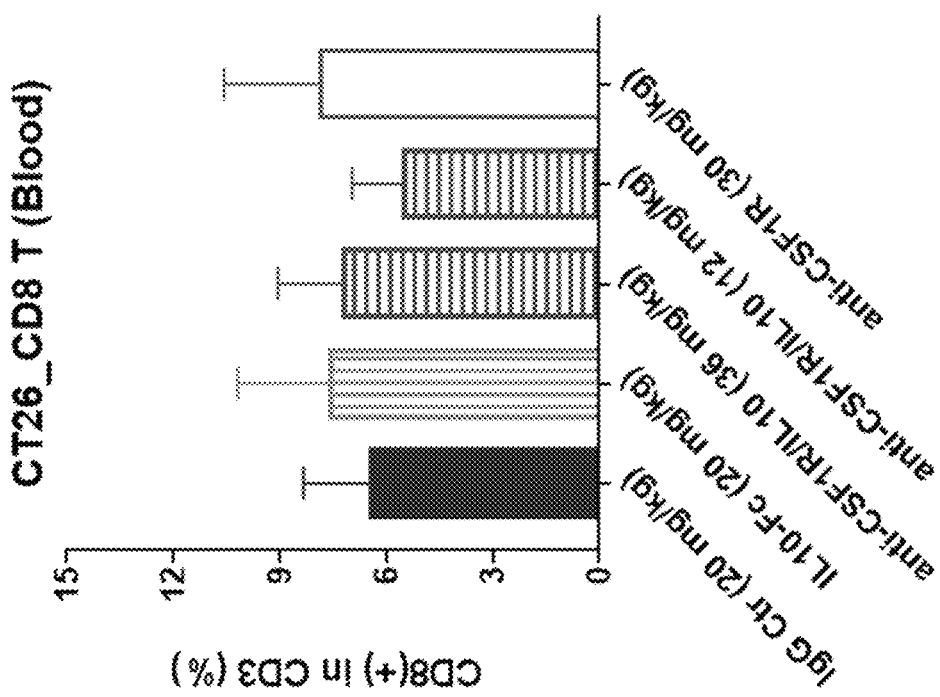
Figure 19A:
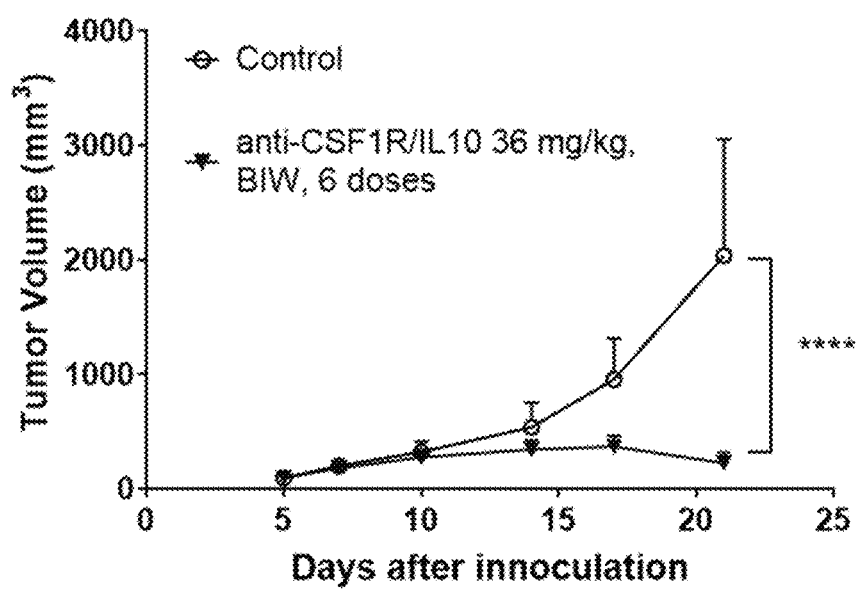
FIG. 19A, FIG. 19B, FIG. 19C, FIG. 19D, FIG. 19E, FIG. 19F, FIG. 19G, and FIG. 19H depict plots showing that anti-CSF1R/IL10 fusion proteins can control tumor growth. EMT6 tumors (FIG. 19A), CT26 tumors (FIG. 19B), MC38 tumors (FIG. 19C), Renca tumors (FIG. 19D), LL2 tumors (FIG. 19E), Pan02 tumors (FIG. 19F), H22 tumors (FIG. 19G), and Q1 tumor (FIG. 19H) were randomized once tumors reached 50-100 mm$^3$ and then treated with PBS control or surrogate anti-CSF1R/IL10 (36 mg/kg) twice weekly for 3 weeks. Tumor volumes over time of mice implanted with tumor cells at day 0. n=10 mice per group. Mean±SD is shown. *$p<0.05$, $p<0.01$, *$p<0.001$
Figure 19B:
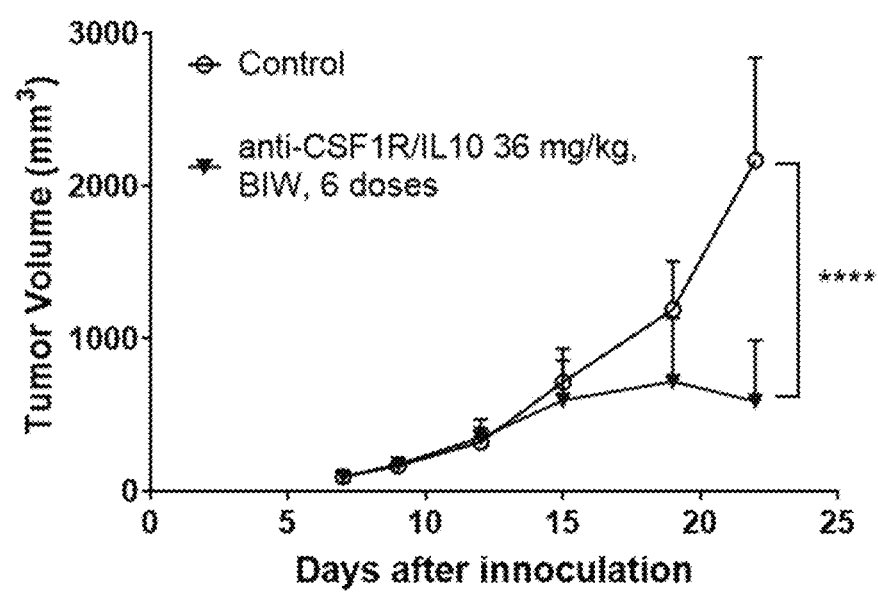
Figure 19C:
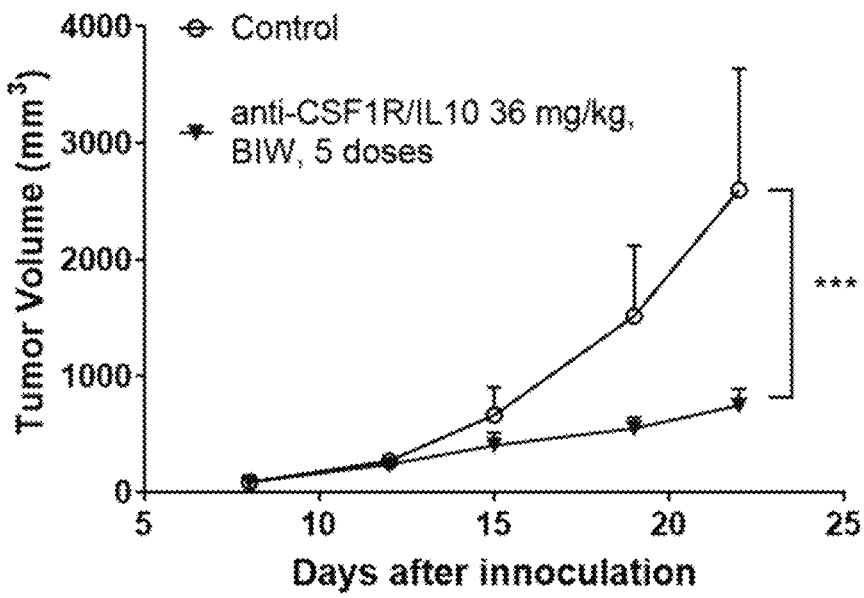
Figure 19D:
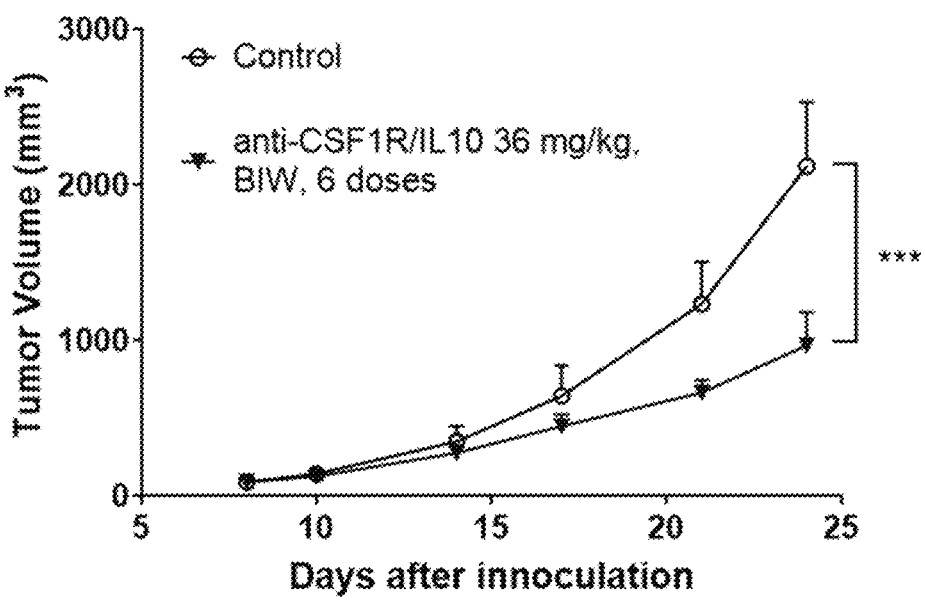
Figure 19E:
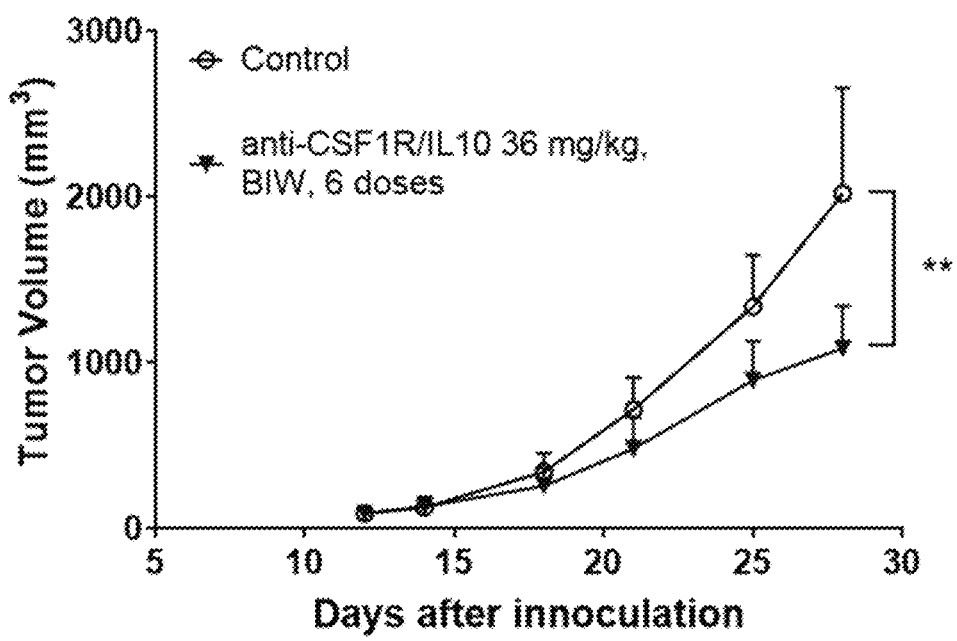
Figure 19F:
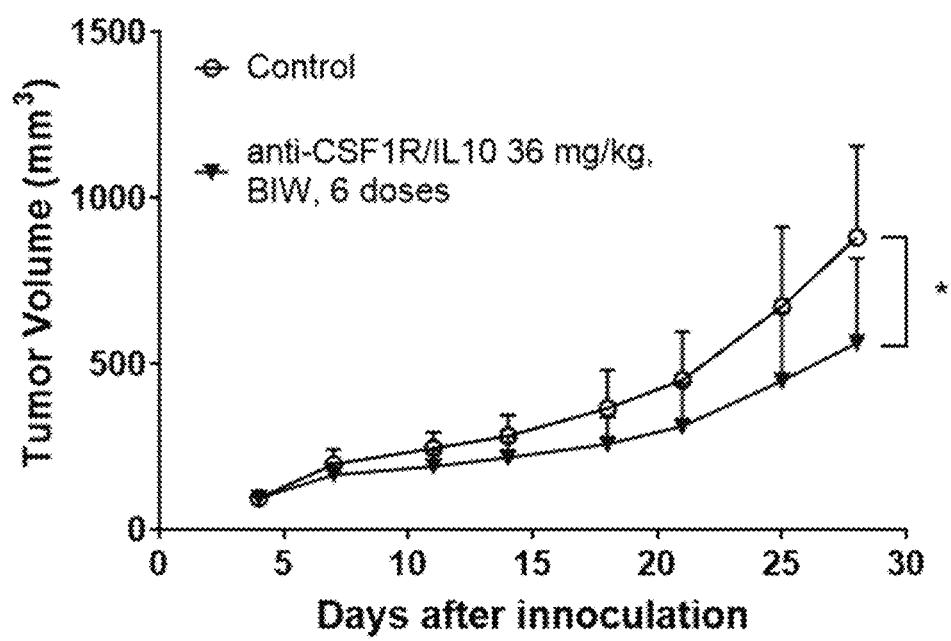
Figure 19G:
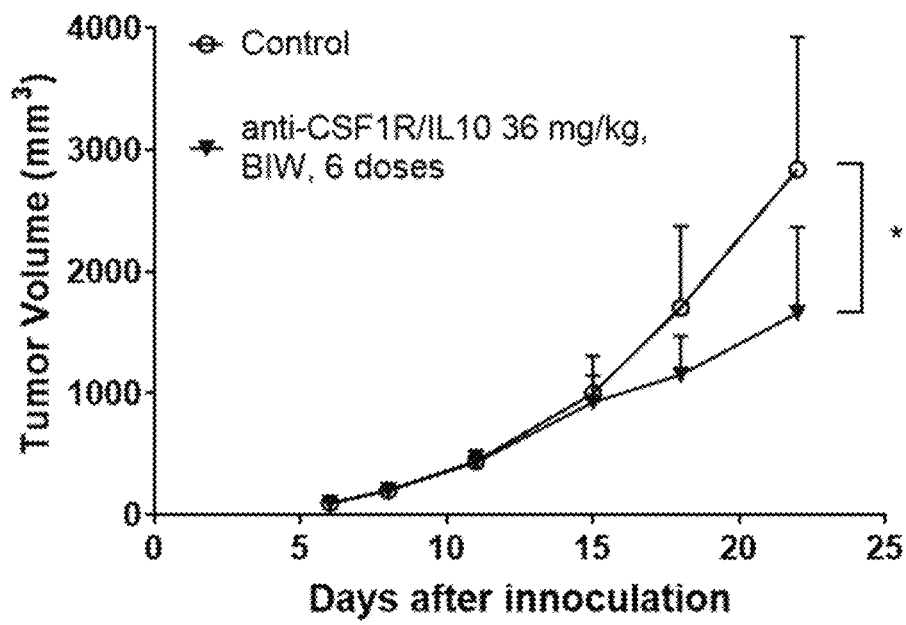
Figure 19H:
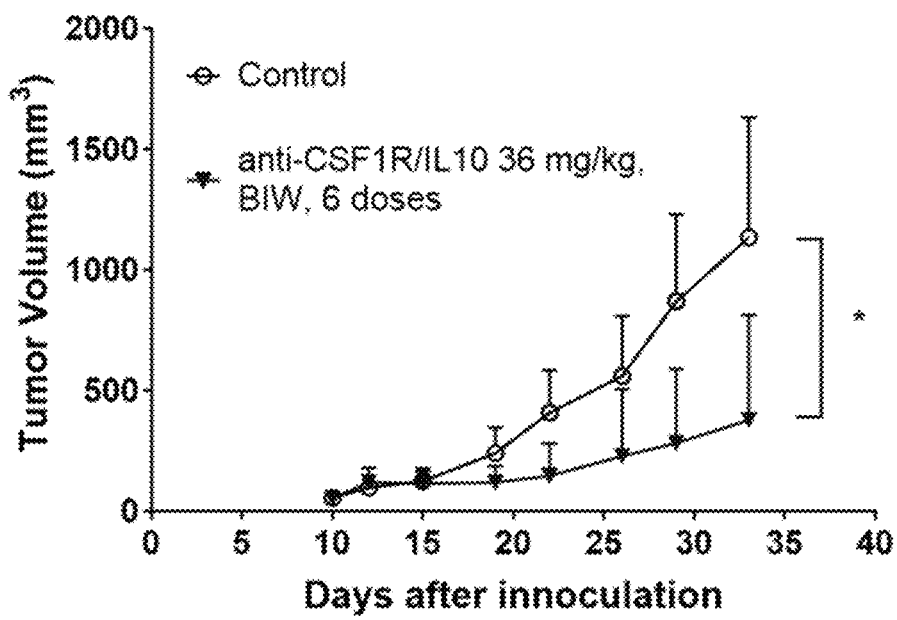

Results: As shown by the plots depicted in FIG. 17A-17C blockade of CSF1R by the anti-CSF1R antibodies reduces TAMs (CD11b+F4/80+) population in the tumor model. As shown by the plots depicted in FIG. 17D-17E the presence of IL-10 in the anti-CSF1R/IL10 fusion increases the CD8+LAG3+PD1+ T-cell population in the tumor model.

N. Anti-Tumor Activity of Anti-CSF1R/IL10 fusion in syngeneic tumor models

Materials and methods: BALB/c mice (6-8 weeks old, female) were implanted subcutaneously with $5 \times 10^5$ CT26.WT cells (ATCC CRL-2638), $5 \times 10^5$ EMT6 cells (ATCC CRL-2755), $1 \times 10^6$ H22 cells (RRID:CVCL_H613), or $1 \times 10^6$ Renca cells (ATCC CRL-2947). C57BL/6 mice (6-8 weeks old, female) were implanted subcutaneously with $3 \times 10^5$ LL2 cells (ATCC CRL-1642), $1 \times 10^6$ MC38 cells (RRID:CVCL_B288), $3 \times 10^6$ Pan02 cells (RRID: CVCL_D627), or $5 \times 10^5$ Q1-2 cells. Mice were randomized into treatment groups when tumor volume reached 50-100 mm³. Mice were then injected intraperitoneally twice weekly with vehicle control, or 36 mg/kg anti-CSF1R/IL10 fusion protein (AB98/IL10). Tumor volume was measured twice per week by caliper measurements until end of the study.

Results: As shown by the plots depicted in FIG. 19A-19G treatment with the surrogate mouse anti-CSF1R/IL10 antibody fusion, AB98/IL10, resulted in significant reduction (~30-70%) of tumor volume at 3 weeks across all of the tumor models.

Notwithstanding the appended claims, the disclosure set forth herein is also defined by the following numbered clauses, which may be beneficial alone or in combination, with one or more other clauses or embodiments. Without limiting the foregoing description, certain non-limiting clauses of the disclosure numbered as below are provided, wherein each of the individually numbered clauses may be used or combined with any of the preceding or following numbered clauses. Thus, this is intended to provide support for all such combinations and is not necessarily limited to the specific combinations explicitly provided below:

1. An isolated antibody or an antigen-binding portion thereof, comprising: a CDR-H1 comprising an amino acid sequence selected from SEQ ID NO: 3 or SEQ ID NO: 28; a CDR-H2 comprising an amino acid sequence selected from SEQ ID NO: 6 or SEQ ID NO: 31; a CDR-H3 comprising an amino acid sequence selected from SEQ ID NO: 8 or SEQ ID NO: 33; a CDR-L1 comprising an amino acid sequence selected from SEQ ID NO: 13 or SEQ ID NO: 37; a CDR-L2 comprising an amino acid sequence selected from KAS or VAS; and a CDR-L3 comprising an amino acid sequence selected from SEQ ID NO: 16 or SEQ ID NO: 40.

2. The isolated antibody or antigen-binding portion thereof of clause 1, wherein: said CDR-H1, CDR-H2, and CDR-H3 are SEQ ID NO: 3, SEQ ID NO: 6, and SEQ ID NO: 8, respectively; and/or said CDR-L1, CDR-L2, and CDR-L3 are SEQ ID NO: 13, KAS, and SEQ ID NO: 16, respectively.

3. The isolated antibody or antigen-binding portion thereof of clause 1, wherein said CDR-H1, CDR-H2, and CDR-H3 are SEQ ID NO: 28, SEQ ID NO: 31, and SEQ ID NO: 33, respectively; and/or said CDR-L1, CDR-L2, and CDR-L3 are SEQ ID NO: 37, VAS, and SEQ ID NO: 40, respectively.

4. The isolated antibody or antigen-binding portion thereof of any one of clauses 1-3, wherein:
   (a) $V_H$ comprises a sequence having at least 90% identity to SEQ ID NO: 2; and $V_L$ comprises a sequence having at least 90% identity to SEQ ID NO: 12;
   (b) $V_H$ comprises a sequence having at least 90% identity to SEQ ID NO: 19; and $V_L$ comprises a sequence having at least 90% identity to SEQ ID NO: 21;
   (c) $V_H$ comprises a sequence having at least 90% identity to SEQ ID NO: 23; and $V_L$ comprises a sequence having at least 90% identity to SEQ ID NO: 25;
   (d) $V_H$ comprises a sequence having at least 90% identity to SEQ ID NO: 27; and $V_L$ comprises a sequence having at least 90% identity to SEQ ID NO: 36;
   (e) $V_H$ comprises a sequence having at least 90% identity to SEQ ID NO: 43; and $V_L$ comprises a sequence having at least 90% identity to SEQ ID NO: 45; or
   (f) wherein $V_H$ comprises a sequence having at least 90% identity to SEQ ID NO: 47; and $V_L$ comprises a sequence having at least 90% identity to SEQ ID NO: 49.

5. A recombinant protein, comprising an isolated antibody or antigen-binding portion thereof of any one of clauses 1-4 fused to an IL-10 polypeptide.

6. The recombinant protein of clause 5, wherein the IL-10 polypeptide comprises the amino acid sequence of SEQ ID NO: 75.

7. The recombinant protein of any one of clauses 5-6, wherein the isolated antibody or antigen-binding portion thereof is fused to the IL-10 polypeptide via a linker; optionally, wherein the linker comprises the amino acid sequence of SEQ ID NO: 78.

8. The recombinant protein of any one of clauses 5-7, comprising one, two, or four IL-10 polypeptide.

9. The recombinant protein of any one of clauses 5-8, comprising a sequence having at least 90% identity to SEQ ID NO: 50, 51, 52, 53, 54, 55, 56, or 57.

10. A pharmaceutical composition comprising an isolated antibody or antigen-binding portion thereof of any one of clauses 1-4 and a pharmaceutically acceptable carrier.

11. The pharmaceutical composition of clause 10, further comprising IL-10.

12. The pharmaceutical composition of clause 11, wherein the isolated antibody or an antigen-binding portion thereof is fused to the IL-10, thereby forming a recombinant protein.

13. The pharmaceutical composition of clause 12, wherein the recombinant protein is a recombinant protein of any one of clauses 5-9.

14. A method for treating cancer, comprising administering to a subject in need thereof an effective amount of an isolated antibody or an antigen-binding portion thereof of any one of clauses 1-4 or a recombinant protein of any one of clauses 5-9.

15. The method of clause 14, wherein the cancer is colon cancer, pancreatic cancer, ovarian cancer, HCC, renal cancer, breast cancer, lung cancer, gastric cancer, head and neck cancer, or oral cancer.

16. A kit for treating cancer, comprising: a CSF1R antagonist and an IL10 agonist.

17. The kit of clause 16, wherein the CSF1R antagonist is an antibody or an antigen-binding fragment thereof, a shRNA, a siRNA, a miRNA, a small molecule inhibitor of CSF1R, or a combination thereof.

18. The kit of any one of clauses 16-17, wherein the CSF1R antagonist is the isolated antibody or antigen-binding portion thereof of any one of clauses 1-4.

19. The kit of any one of clauses 16-18, wherein the IL10 agonist is IL10, an IL10 receptor binding protein, an IL10 receptor agonist, or a combination thereof.

20. A method for treating cancer, comprising administering a subject in need a CSF1R antagonist and an IL-10 agonist.

21. The method of clause 20, wherein the CSF1R antagonist is an antibody or an antigen-binding fragment thereof, a shRNA, a siRNA, a miRNA, a small molecule inhibitor of CSF1R, or a combination thereof.

22. The method of any one of clauses 20-21, wherein the CSF1R antagonist is the isolated antibody or antigen-binding portion thereof of any one of clauses 1-4.

23. The method of any one of clauses 20-22, wherein the IL10 agonist is IL10, an IL10 receptor binding protein, or a combination thereof.

24. The method of any one of clauses 20-23, further comprising administering to the subject a T cell therapy.

25. A method for T cell activation comprising contacting a T cell population with a CSF1R antagonist and an IL10 agonist.

26. The method of clause 25, wherein the CSF1R antagonist is an antibody or an antigen-binding fragment thereof, a shRNA, a siRNA, a miRNA, a small molecule inhibitor of CSF1R, or a combination thereof.

27. The method of any one of clauses 25-26, wherein the CSF1R antagonist is the isolated antibody or antigen-binding portion thereof of any one of clauses 1-4.

28. The method of any one of clauses 25-27, wherein the IL10 agonist is IL10, an IL10 receptor binding protein, or a combination thereof.

29. The method of clause 23, wherein the IL-10 agonist is IL-10.

30. The method of any one of clause 27-29, wherein the isolated antibody or antigen-binding portion thereof is fused to the IL10, thereby forming a recombinant protein.

31. The method of clause 30, wherein the recombinant protein is a recombinant protein of any one of clauses 5-9.

32. The method of clause 31, wherein the T cell is a CD8$^+$ T cell, CD4$^+$ T cell, or a combination thereof.

33. An anti-CSF1R antibody comprising (i) a first light chain complementary determining region (CDR-L1), a second light chain complementary determining region (CDR-L2), and a third light chain complementary determining region (CDR-L3), and/or (ii) a first heavy chain complementary determining region (CDR-H1), a second heavy chain complementary determining region (CDR-H2), and a third heavy chain complementary determining region (CDR-H3), wherein:
  (a) CDR-H1 comprises an amino acid sequence selected from SEQ ID NO: 3, 4, 28, or 29;
  (b) CDR-H2 comprises an amino acid sequence selected from SEQ ID NO: 6, 7, 31, or 32;
  (c) CDR-H3 comprises an amino acid sequence selected from SEQ ID NO: 8, 9, 33, or 34;
  (d) CDR-L1 comprises an amino acid sequence selected from SEQ ID NO: 13, 14, 37, or 38;
  (e) CDR-L2 comprises an amino acid sequence selected from KAS, VAS, or SEQ ID NO: 15, or 39;
  (f) CDR-L3 comprises an amino acid sequence selected from SEQ ID NO: 16, 17, 40, or 41.

34. The antibody of clause 33, wherein:
  (a) CDR-H1 comprises the amino acid sequence of SEQ ID NO: 3 or 4, CDR-H2 comprises the amino acid sequence of SEQ ID NO: 6 or 7, and CDR-H3 comprises the amino acid sequence of SEQ ID NO: 8 or 9; or
  (b) CDR-H1 comprises the amino acid sequence of SEQ ID NO: 28 or 29, CDR-H2 comprises the amino acid sequence of SEQ ID NO: 31 or 32, and CDR-H3 comprises the amino acid sequence of SEQ ID NO: 33 or 34.

35. The antibody of any one of clauses 33-34, wherein:
  (a) CDR-L1 comprises the amino acid sequence of SEQ ID NO: 13 or 14, CDR-L2 comprises the amino acid sequence of KAS, or SEQ ID NO: 15, and CDR-L3 comprises the amino acid sequence of SEQ ID NO: 16 or 17; or
  (b) CDR-L1 comprises the amino acid sequence of SEQ ID NO: 37 or 38, CDR-L2 comprises the amino acid sequence of VAS or SEQ ID NO: 39, and CDR-L3 comprises the amino acid sequence of SEQ ID NO: 40 or 41.

36. The antibody of any one of clauses 33-35, wherein:
  (a) CDR-H1 comprises the amino acid sequence of SEQ ID NO: 3, CDR-H2 comprises the amino acid sequence of SEQ ID NO: 6, CDR-H3 comprises the amino acid sequence of SEQ ID NO: 8, CDR-L1 comprises the amino acid sequence of SEQ ID NO: 13, CDR-L2 comprises the amino acid sequence of KAS, and CDR-L3 comprises the amino acid sequence of SEQ ID NO: 16;

(b) CDR-H1 comprises the amino acid sequence of SEQ ID NO: 28, CDR-H2 comprises the amino acid sequence of SEQ ID NO: 31, CDR-H3 comprises the amino acid sequence of SEQ ID NO: 33, CDR-L1 comprises the amino acid sequence of SEQ ID NO: 37, CDR-L2 comprises the amino acid sequence of VAS, and CDR-L3 comprises the amino acid sequence of SEQ ID NO: 40;

(c) CDR-H1 comprises the amino acid sequence of SEQ ID NO: 4, CDR-H2 comprises the amino acid sequence of SEQ ID NO: 7, CDR-H3 comprises the amino acid sequence of SEQ ID NO: 9, CDR-L1 comprises the amino acid sequence of SEQ ID NO: 14, CDR-L2 comprises the amino acid sequence of SEQ ID NO: 15, and CDR-L3 comprises the amino acid sequence of SEQ ID NO: 17;

(d) CDR-H1 comprises the amino acid sequence of SEQ ID NO: 29, CDR-H2 comprises the amino acid sequence of SEQ ID NO: 32, CDR-H3 comprises the amino acid sequence of SEQ ID NO: 34, CDR-L1 comprises the amino acid sequence of SEQ ID NO: 38, CDR-L2 comprises the amino acid sequence of VAS or SEQ ID NO: 39, and CDR-L3 comprises the amino acid sequence of SEQ ID NO: 41.

37. The antibody of any one of claims 33-36, wherein the antibody comprises (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:
(a) HVR-H1 comprises an amino acid sequence selected from SEQ ID NO: 5 or 30;
(b) HVR-H2 comprises an amino acid sequence selected from SEQ ID NO: 7 or 32;
(c) HVR-H3 comprises an amino acid sequence selected from SEQ ID NO: 10 or 33;
(d) HVR-L1 comprises an amino acid sequence selected from SEQ ID NO: 14 or 38;
(e) HVR-L2 comprises an amino acid sequence selected from SEQ ID NO: 15 or 39;
(f) HVR-L3 comprises an amino acid sequence selected from SEQ ID NO: 17 or 41.

38. The antibody of clause 37, wherein:
(a) HVR-H1 comprises the amino acid sequence of SEQ ID NO: 5; HVR-H2 comprises the amino acid sequence of SEQ ID NO: 7; HVR-H3 comprises the amino acid sequence of SEQ ID NO: 10; HVR-L1 comprises the amino acid sequence of SEQ ID NO: 14; HVR-L2 comprises the amino acid sequence of SEQ ID NO: 15; and HVR-L3 comprises an amino acid sequence of SEQ ID NO: 41; or
(b) HVR-H1 comprises an amino acid sequence of SEQ ID NO: 30; HVR-H2 comprises an amino acid sequence of SEQ ID NO: 32; HVR-H3 comprises an amino acid sequence of SEQ ID NO: 33; HVR-L1 comprises an amino acid sequence of SEQ ID NO: 38; HVR-L2 comprises an amino acid sequence of SEQ ID NO: 39; and HVR-L3 comprises an amino acid sequence of SEQ ID NO: 41.

39. The antibody of any one of clauses 33-38, wherein the antibody comprises a heavy chain variable domain ($V_H$) amino acid sequence having at least 90% identity to a sequence selected from SEQ ID NO: 2, 19, 23, 27, 43, or 47; and/or a light chain variable domain ($V_L$) amino acid sequence having at least 90% identity to a sequence selected from SEQ ID NO: 12, 21, 25, 36, 45, or 49; optionally, wherein:
(a) the antibody comprises a $V_H$ amino acid sequence having at least 90% identity to SEQ ID NO: 2; and/or a light chain variable domain ($V_L$) amino acid sequence having at least 90% identity to SEQ ID NO: 12;
(b) the antibody comprises a $V_H$ amino acid sequence having at least 90% identity to SEQ ID NO: 19; and/or a $V_L$ amino acid sequence having at least 90% identity to SEQ ID NO: 21;
(c) the antibody comprises a $V_H$ amino acid sequence having at least 90% identity to SEQ ID NO: 23; and/or a $V_L$ amino acid sequence having at least 90% identity to SEQ ID NO: 25;
(d) the antibody comprises a $V_H$ amino acid sequence having at least 90% identity to SEQ ID NO: 27; and/or a $V_L$ amino acid sequence having at least 90% identity to SEQ ID NO: 36;
(e) the antibody comprises a $V_H$ amino acid sequence having at least 90% identity to SEQ ID NO: 43; and/or a $V_L$ amino acid sequence having at least 90% identity to SEQ ID NO: 45; or
(f) the antibody comprises a $V_H$ amino acid sequence having at least 90% identity to SEQ ID NO: 47; and/or a $V_L$ amino acid sequence having at least 90% identity to SEQ ID NO: 49.

40. The antibody of any one of clauses 33-39, wherein the antibody comprises a heavy chain (HC) amino acid sequence having at least 90% identity to a sequence selected from SEQ ID NO: 58, 60, 62, 64, 66, or 68, and/or a light chain (LC) amino acid sequence having at least 90% identity to a sequence selected from SEQ ID NO: 59, 61, 63, 65, 67, or 69; optionally, wherein the antibody comprises:
(a) the HC amino acid sequence of SEQ ID NO: 58, and the LC amino acid sequence of SEQ ID NO: 59;
(b) the HC amino acid sequence of SEQ ID NO: 60, and LC amino acid sequence of SEQ ID NO: 61;
(c) the HC amino acid sequence of SEQ ID NO: 62, and the LC amino acid sequence of SEQ ID NO: 63;
(d) the HC amino acid sequence of SEQ ID NO: 64, and the LC amino acid sequence of SEQ ID NO: 65;
(e) the HC amino acid sequence of SEQ ID NO: 66, and the LC amino acid sequence of SEQ ID NO: 67; or
(f) the HC amino acid sequence of SEQ ID NO: 68, and the LC amino acid sequence of SEQ ID NO: 69

41. The antibody of any one of clauses 33-40, wherein the antibody comprises a HC fused via a linker to an IL10 polypeptide; optionally, wherein:
(a) the linker comprises an amino acid sequence of SEQ ID NO: 78;
(b) the IL10 polypeptide comprises one, two, or four IL10 polypeptides; and/or
(c) the IL10 polypeptide comprises an amino acid sequence of SEQ ID NO: 75;
(d) the HC comprises an amino acid sequence having at least 90% identity to a sequence selected from SEQ ID NO: 50, 51, 52, 53, 54, 55, 56, or 57.

42. The antibody of clause 41, wherein the antibody comprises a comprises a heavy chain (HC) amino acid sequence having at least 90% identity to a sequence selected from SEQ ID NO: 50, 51, 52, 53, 54, 55, 56, or 57, and a light chain (LC) amino acid sequence having at least 90% identity to a sequence selected from SEQ ID NO: 59, 61, 63, 65, 67, or 69; optionally, wherein the antibody comprises:
(a) the HC amino acid sequence of SEQ ID NO: 50, and the LC amino acid sequence of SEQ ID NO: 59;

(b) the HC amino acid sequence of SEQ ID NO: 51, and the LC amino acid sequence of SEQ ID NO: 59;
(c) the HC amino acid sequence of SEQ ID NO: 52, and LC amino acid sequence of SEQ ID NO: 61;
(d) the HC amino acid sequence of SEQ ID NO: 53, and the LC amino acid sequence of SEQ ID NO: 63;
(e) the HC amino acid sequence of SEQ ID NO: 54, and the LC amino acid sequence of SEQ ID NO: 65;
(f) the HC amino acid sequence of SEQ ID NO: 55, and the LC amino acid sequence of SEQ ID NO: 65;
(g) the HC amino acid sequence of SEQ ID NO: 56, and the LC amino acid sequence of SEQ ID NO: 67; or
(h) the HC amino acid sequence of SEQ ID NO: 57, and the LC amino acid sequence of SEQ ID NO: 69.

43. The antibody of any one of clauses 33-42, wherein:
(a) the antibody binds to human CSF1R with a binding affinity of $1 \times 10^{-8}$ M or less, $1 \times 10^{-9}$ M or less, $1 \times 10^{-10}$ M or less; optionally, wherein the binding affinity is measured by equilibrium dissociation constant ($K_D$) to a huCSF1R polypeptide of SEQ ID NO: 70;
(b) the antibody binds to cynomolgus CSF1R with a binding affinity of $1 \times 10^{-8}$ M or less, $1 \times 10^{-9}$ M or less, $1 \times 10^{-10}$ M or less; optionally, wherein the binding affinity is measured by equilibrium dissociation constant ($K_D$) to a cynoCSF1R polypeptide of SEQ ID NO: 71;
(c) the antibody decreases CSF1-induced and IL34-induced phosphorylation of huCSF1R or AKT;
(d) the antibody inhibits CSF1-dependent and IL34-induced cell proliferation by at least 65%, at least 75%, at least 85%, at least 95%, or at least 100%; optionally, wherein at a CSF1 concentration of 20 ng/mL or a IL34 concentration of 33 ng/mL the antibody has an $IC_{50}$ of 5 nM or less, 1 nM or less, 0.5 nM or less, or 0.1 nM or less;
(e) the antibody inhibits CSF1-dependent dependent survival of human CD14+ monocytes or monocyte-derived macrophages by at least 65%, at least 75%, at least 85%, at least 95%, or at least 100%; optionally, wherein at a CSF1 concentration of 100 ng/mL the antibody has an $IC_{50}$ of 5 nM or less, 1 nM or less, 0.5 nM or less, or 0.1 nM or less;
(f) the antibody increases NK-cell mediated ADCC against CSF1R expressing 293F cells by at least 10%; at least 20%, or at least 25%;
(g) the antibody decreases tumor volume in a syngeneic mouse tumor model measured at 21 days by at least 25%, at least 50%, at least 75%, or more, wherein the mouse tumor model is selected from: CT26 CRC, EMT6 TNBC, MC38 CRC, Renca RCC, LL/2 lung, Pan02 PDAC, H22 HCC, Q1 HNSCC;
(h) the antibody increases blood levels of CSF1 and IL34 in a CT26 colon tumor syngeneic mouse model by at least 50-fold, at least 100-fold, at 200-fold, or at least 500-fold;
(i) the antibody decreases TAM population in in a CT26 colon tumor syngeneic mouse model by at least 20%, at least 30%, at least 40%, at least 50%, at least 60%, or more; optionally, wherein the MDSC population is reduced less than 10%, less than 5%, or less;
(j) the antibody increases MC/9 cell proliferation by at least 25%, at least 50%, at least 100%, at least 150%, at least 200% or more;
(k) the antibody increases IFNγ and granzyme B production from activated CD8 T cells by at least 25%, at least 50%, at least 100%, or more; and/or
(l) the antibody increases CD8+LAG3+PD1+ T cell blood levels in a CT26 colon tumor syngeneic mouse model by at least 2-fold, at least 4-fold, at least 6-fold, at least 8-fold, at least 10-fold, or more.

44. An isolated polynucleotide or vector encoding the antibody of any one of clauses 33-43; or an isolated host cell comprising the oligonucleotide or vector; optionally, wherein the host cell is selected from a Chinese hamster ovary (CHO) cell, a myeloma cell (e.g. Y0, NS0, Sp2/0), a monkey kidney cell (COS-7), a human embryonic kidney line (293), a baby hamster kidney cell (BHK), a mouse Sertoli cell (e.g., TM4), an African green monkey kidney cell (VERO-76), a human cervical carcinoma cell (HELA), a canine kidney cell, a human lung cell (W138), a human liver cell (Hep G2), a mouse mammary tumor cell, a TR1 cell, a Medical Research Council 5 (MRC 5) cell, and a FS4 cell.

45. A method of producing an antibody comprising culturing the host cell of clause 44 so that an antibody is produced.

46. A pharmaceutical composition comprising an antibody of any one of clauses 33-43 and a pharmaceutically acceptable carrier; optionally, wherein the composition further comprises IL10, a chemotherapeutic agent, and/or an antibody comprising a specificity for an immune checkpoint molecule 47. A method of treating a CSF1R-mediated disease in a subject, the method comprising administering to the subject a therapeutically effective amount of an antibody of any one of clauses 33-43, or administering to the subject a therapeutically effective amount of a pharmaceutical composition of claim 46; optionally, wherein the disease is cancer; optionally, wherein the cancer is colon cancer, pancreatic cancer, ovarian cancer, HCC, renal cancer, breast cancer, lung cancer, gastric cancer, head and neck cancer, or oral cancer.

48. A method for treating cancer in a subject, comprising administering to the subject a CSF1R antagonist and an IL10 agonist; optionally, wherein the CSF1R antagonist comprises an anti-CSF1R antibody, a shRNA, a siRNA, a miRNA, a small molecule inhibitor of CSF1R, or a combination thereof; optionally, wherein the IL10 agonist is IL10, an IL10 receptor binding protein, or a combination thereof; optionally, wherein the CSF1R antagonist is an anti-CSF1R antibody of any one of clauses 33-43; optionally, wherein the CSF1R antagonist and the IL10 agonist comprise an anti-CSF1R antibody having a HC fused via a linker to an IL10 polypeptide.

49. The method of clause 48, wherein the cancer is colon cancer, pancreatic cancer, ovarian cancer, HCC, renal cancer, breast cancer, lung cancer, gastric cancer, head and neck cancer, or oral cancer 50. The method of any one of clauses 48-49, wherein the method further comprises administering to the subject a T cell therapy.

51. Use of a composition or formulation comprising anti-CSF1R antibody of any one of clauses 33-43 in a therapy or in a medicament for use in a therapy; optionally, wherein the therapy is for a CSF1R-mediated disease; optionally wherein the CSF1R-mediated disease is a cancer.

52. Use of a composition or a formulation comprising an anti-CSF1R antibody of any one of clauses 33-43 in the manufacture or preparation of a medicament; optionally, wherein the medicament is for treating a CSF1R-mediated disease; optionally wherein the CSF1R-mediated disease is a cancer.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

What is claimed is:

1. An anti-CSF1R antibody comprising (i) a first light chain complementary determining region (CDR-L1), a second light chain complementary determining region (CDR-L2), and a third light chain complementary determining region (CDR-L3), and (ii) a first heavy chain complementary determining region (CDR-H1), a second heavy chain complementary determining region (CDR-H2), and a third heavy chain complementary determining region (CDR-H3), wherein:
 (a) CDR-H1 comprises an amino acid sequence selected from SEQ ID NO: 3, 4, 28, or 29;
 (b) CDR-H2 comprises an amino acid sequence selected from SEQ ID NO: 6, 7, 31, or 32;
 (c) CDR-H3 comprises an amino acid sequence selected from SEQ ID NO: 8, 9, 33, or 34;
 (d) CDR-L1 comprises an amino acid sequence selected from SEQ ID NO: 13, 14, 37, or 38;
 (e) CDR-L2 comprises an amino acid sequence selected from KAS, VAS, or SEQ ID NO: 15, or 39;
 (f) CDR-L3 comprises an amino acid sequence selected from SEQ ID NO: 16, 17, 40, or 41.

2. The antibody of claim 1, wherein:
 (a) CDR-H1 comprises the amino acid sequence of SEQ ID NO: 3 or 4, CDR-H2 comprises the amino acid sequence of SEQ ID NO: 6 or 7, and CDR-H3 comprises the amino acid sequence of SEQ ID NO: 8 or 9; or
 (b) CDR-H1 comprises the amino acid sequence of SEQ ID NO: 28 or 29, CDR-H2 comprises the amino acid sequence of SEQ ID NO: 31 or 32, and CDR-H3 comprises the amino acid sequence of SEQ ID NO: 33 or 34.

3. The antibody of claim 1, wherein:
 (a) CDR-L1 comprises the amino acid sequence of SEQ ID NO: 13 or 14, CDR-L2 comprises the amino acid sequence of KAS, or SEQ ID NO: 15, and CDR-L3 comprises the amino acid sequence of SEQ ID NO: 16 or 17; or
 (b) CDR-L1 comprises the amino acid sequence of SEQ ID NO: 37 or 38, CDR-L2 comprises the amino acid sequence of VAS or SEQ ID NO: 39, and CDR-L3 comprises the amino acid sequence of SEQ ID NO: 40 or 41.

4. The antibody of claim 1, wherein:
 (a) CDR-H1 comprises the amino acid sequence of SEQ ID NO: 3, CDR-H2 comprises the amino acid sequence of SEQ ID NO: 6, CDR-H3 comprises the amino acid sequence of SEQ ID NO: 8, CDR-L1 comprises the amino acid sequence of SEQ ID NO: 13, CDR-L2 comprises the amino acid sequence of KAS, and CDR-L3 comprises the amino acid sequence of SEQ ID NO: 16;
 (b) CDR-H1 comprises the amino acid sequence of SEQ ID NO: 28, CDR-H2 comprises the amino acid sequence of SEQ ID NO: 31, CDR-H3 comprises the amino acid sequence of SEQ ID NO: 33, CDR-L1 comprises the amino acid sequence of SEQ ID NO: 37, CDR-L2 comprises the amino acid sequence of VAS, and CDR-L3 comprises the amino acid sequence of SEQ ID NO: 40;
 (c) CDR-H1 comprises the amino acid sequence of SEQ ID NO: 4, CDR-H2 comprises the amino acid sequence of SEQ ID NO: 7, CDR-H3 comprises the amino acid sequence of SEQ ID NO: 9, CDR-L1 comprises the amino acid sequence of SEQ ID NO: 14, CDR-L2 comprises the amino acid sequence of SEQ ID NO: 15, and CDR-L3 comprises the amino acid sequence of SEQ ID NO: 17; or
 (d) CDR-H1 comprises the amino acid sequence of SEQ ID NO: 29, CDR-H2 comprises the amino acid sequence of SEQ ID NO: 32, CDR-H3 comprises the amino acid sequence of SEQ ID NO: 34, CDR-L1 comprises the amino acid sequence of SEQ ID NO: 38, CDR-L2 comprises the amino acid sequence of VAS or SEQ ID NO: 39, and CDR-L3 comprises the amino acid sequence of SEQ ID NO: 41.

5. The antibody of claim 1, wherein the antibody comprises (i) a first light chain hypervariable region (HVR-L1), a second light chain hypervariable region (HVR-L2), and a third light chain hypervariable region (HVR-L3), and (ii) a first heavy chain hypervariable region (HVR-H1), a second heavy chain hypervariable region (HVR-H2), and a third heavy chain hypervariable region (HVR-H3), wherein:
 (a) HVR-H1 comprises an amino acid sequence selected from SEQ ID NO: 5 or 30;
 (b) HVR-H2 comprises an amino acid sequence selected from SEQ ID NO: 7 or 32;
 (c) HVR-H3 comprises an amino acid sequence selected from SEQ ID NO: 10 or 33;
 (d) HVR-L1 comprises an amino acid sequence selected from SEQ ID NO: 14 or 38;
 (e) HVR-L2 comprises an amino acid sequence selected from SEQ ID NO: 15 or 39;
 (f) HVR-L3 comprises an amino acid sequence selected from SEQ ID NO: 17 or 41.

6. The antibody of claim 1, wherein the antibody comprises a heavy chain variable domain ($V_H$) amino acid sequence having at least 90% identity to a sequence selected from SEQ ID NO: 2, 19, 23, 27, 43, or 47; and a light chain variable domain ($V_L$) amino acid sequence having at least 90% identity to a sequence selected from SEQ ID NO: 12, 21, 25, 36, 45, or 49.

7. The antibody of claim 6, wherein:
 (a) the antibody comprises a $V_H$ amino acid sequence having at least 90% identity to SEQ ID NO: 2; and/or a light chain variable domain ($V_L$) amino acid sequence having at least 90% identity to SEQ ID NO: 12;
 (b) the antibody comprises a $V_H$ amino acid sequence having at least 90% identity to SEQ ID NO: 19; and/or a $V_L$ amino acid sequence having at least 90% identity to SEQ ID NO: 21;
 (c) the antibody comprises a $V_H$ amino acid sequence having at least 90% identity to SEQ ID NO: 23; and/or a $V_L$ amino acid sequence having at least 90% identity to SEQ ID NO: 25;

(d) the antibody comprises a $V_H$ amino acid sequence having at least 90% identity to SEQ ID NO: 27; and/or a $V_L$ amino acid sequence having at least 90% identity to SEQ ID NO: 36;

(e) the antibody comprises a $V_H$ amino acid sequence having at least 90% identity to SEQ ID NO: 43; and/or a $V_L$ amino acid sequence having at least 90% identity to SEQ ID NO: 45; or (f) the antibody comprises a $V_H$ amino acid sequence having at least 90% identity to SEQ ID NO: 47; and/or a $V_L$ amino acid sequence having at least 90% identity to SEQ ID NO: 49.

8. The antibody of claim 1, wherein the antibody comprises a heavy chain (HC) amino acid sequence having at least 90% identity to a sequence selected from SEQ ID NO: 58, 60, 62, 64, 66, or 68, and/or a light chain (LC) amino acid sequence having at least 90% identity to a sequence selected from SEQ ID NO: 59, 61, 63, 65, 67, or 69.

9. The antibody of claim 8, wherein the antibody comprises:
(a) the HC amino acid sequence of SEQ ID NO: 58, and the LC amino acid sequence of SEQ ID NO: 59;
(b) the HC amino acid sequence of SEQ ID NO: 60, and LC amino acid sequence of SEQ ID NO: 61;
(c) the HC amino acid sequence of SEQ ID NO: 62, and the LC amino acid sequence of SEQ ID NO: 63;
(d) the HC amino acid sequence of SEQ ID NO: 64, and the LC amino acid sequence of SEQ ID NO: 65;
(e) the HC amino acid sequence of SEQ ID NO: 66, and the LC amino acid sequence of SEQ ID NO: 67; or
(f) the HC amino acid sequence of SEQ ID NO: 68, and the LC amino acid sequence of SEQ ID NO: 69.

10. The antibody of claim 1, wherein the antibody comprises a heavy chain (HC) fused via a linker to an IL10 polypeptide.

11. The antibody of claim 10, wherein:
(a) the linker comprises an amino acid sequence of SEQ ID NO: 78;
(b) the IL10 polypeptide comprises one, two, or four IL10 polypeptides;
(c) the IL10 polypeptide comprises an amino acid sequence of SEQ ID NO: 75; and/or
(d) the HC comprises an amino acid sequence having at least 90% identity to a sequence selected from SEQ ID NO: 50, 51, 52, 53, 54, 55, 56, or 57.

12. The antibody of claim 9, wherein the antibody comprises a comprises a heavy chain (HC) amino acid sequence having at least 90% identity to a sequence selected from SEQ ID NO: 50, 51, 52, 53, 54, 55, 56, or 57, and a light chain (LC) amino acid sequence having at least 90% identity to a sequence selected from SEQ ID NO: 59, 61, 63, 65, 67, or 69.

13. The antibody of claim 12, wherein the antibody comprises:
(a) the HC amino acid sequence of SEQ ID NO: 50, and the LC amino acid sequence of SEQ ID NO: 59;
(b) the HC amino acid sequence of SEQ ID NO: 51, and the LC amino acid sequence of SEQ ID NO: 59;
(c) the HC amino acid sequence of SEQ ID NO: 52, and LC amino acid sequence of SEQ ID NO: 61;
(d) the HC amino acid sequence of SEQ ID NO: 53, and the LC amino acid sequence of SEQ ID NO: 63;
(e) the HC amino acid sequence of SEQ ID NO: 54, and the LC amino acid sequence of SEQ ID NO: 65;
(f) the HC amino acid sequence of SEQ ID NO: 55, and the LC amino acid sequence of SEQ ID NO: 65;
(g) the HC amino acid sequence of SEQ ID NO: 56, and the LC amino acid sequence of SEQ ID NO: 67; or
(h) the HC amino acid sequence of SEQ ID NO: 57, and the LC amino acid sequence of SEQ ID NO: 69.

14. A pharmaceutical composition comprising an antibody of claim 1 and a pharmaceutically acceptable carrier.

15. A method of treating cancer in a subject, the method comprising administering to the subject a therapeutically effective amount of an antibody of claim 1, or a therapeutically effective amount of a pharmaceutical composition of claim 14.

16. The method of claim 15, wherein the disease is colon cancer, pancreatic cancer, ovarian cancer, HCC, renal cancer, breast cancer, lung cancer, gastric cancer, head and neck cancer, or oral cancer.

17. The method of claim 15, wherein the method further comprises administering to the subject a therapeutically effective amount of an IL-10 agonist.

18. The method of claim 15, wherein the antibody has a heavy chain (HC) fused via a linker to an IL10 polypeptide.

19. The method of claim 15, wherein the method further comprises administering to the subject a T cell therapy.

* * * * *

SEQUENCE LISTING

<160> NUMBER OF SEQ ID NOS: 78

<210> SEQ ID NO 1
<211> LENGTH: 369
<212> TYPE: DNA
<213> ORGANISM: Artificial
<220> FEATURE:
<223> OTHER INFORMATION: Synthetic polynucleotide

<400> SEQUENCE: 1

```
gagatccagc tgcagcagtc tggagctgag ctggtgaagc ctagggcttc agtgaagata      60
tcctgcgagg cttctggtta ctcattcact ggctacaaca tgaactgggt gaagcagagc     120
cctggaaaga gccttgagtg gattggagat attaatcctt actatggtgc tactacctac     180
aatcagaagt tcaagggcaa ggccacattg actgtagaca atcttccag cacagcctac      240 atgcagctca cagcctgac atctgaggac tctgcagtct attactgtgc aagaagaggg     300
gactatggtg actacgaggg ctggtacttc gatgtctggg gcgcagggac cacggtcacc     360
gtctcctca                                                             369
```

<210> SEQ ID NO 2
<211> LENGTH: 123
<212> TYPE: PRT
<213> ORGANISM: Artificial
<220> FEATURE:
<223> OTHER INFORMATION: Synthetic polypeptide

<400> SEQUENCE: 2

```
Glu Ile Gln Leu Gln Gln Ser Gly Ala Glu Leu Val Lys Pro Arg Ala
1               5                   10                  15

Ser Val Lys Ile Ser Cys Glu Ala Ser Gly Tyr Ser Phe Thr Gly Tyr
            20                  25                  30

Asn Met Asn Trp Val Lys Gln Ser Pro Gly Lys Ser Leu Glu Trp Ile
        35                  40                  45

Gly Asp Ile Asn Pro Tyr Tyr Gly Ala Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Ala Gly Thr Thr Val Thr Val Ser Ser
        115                 120
```

<210> SEQ ID NO 3
<211> LENGTH: 8

<212> TYPE: PRT
<213> ORGANISM: Artificial
<220> FEATURE:
<223> OTHER INFORMATION: Synthetic polypeptide

<400> SEQUENCE: 3

Gly Tyr Ser Phe Thr Gly Tyr Asn
1               5

<210> SEQ ID NO 4
<211> LENGTH: 5
<212> TYPE: PRT
<213> ORGANISM: Artificial
<220> FEATURE:
<223> OTHER INFORMATION: Synthetic polypeptide

<400> SEQUENCE: 4

Gly Tyr Asn Met Asn
1               5

<210> SEQ ID NO 5
<211> LENGTH: 8
<212> TYPE: PRT
<213> ORGANISM: Artificial
<220> FEATURE:
<223> OTHER INFORMATION: Synthetic polypeptide

<400> SEQUENCE: 5

Gly Tyr Ser Phe Thr Gly Tyr Asn
1               5

<210> SEQ ID NO 6
<211> LENGTH: 8
<212> TYPE: PRT
<213> ORGANISM: Artificial
<220> FEATURE:
<223> OTHER INFORMATION: Synthetic polypeptide

<400> SEQUENCE: 6

Ile Asn Pro Tyr Tyr Gly Ala Thr
1               5

<210> SEQ ID NO 7
<211> LENGTH: 17
<212> TYPE: PRT
<213> ORGANISM: artificial
<220> FEATURE:
<223> OTHER INFORMATION: Synthetic polypeptide

<400> SEQUENCE: 7

Asp Ile Asn Pro Tyr Tyr Gly Ala Thr Thr Tyr Asn Gln Lys Phe Lys
1               5                   10                  15

Gly

<210> SEQ ID NO 8
<211> LENGTH: 16
<212> TYPE: PRT
<213> ORGANISM: Artificial
<220> FEATURE:
<223> OTHER INFORMATION: Synthetic polypeptide

<400> SEQUENCE: 8

Ala Arg Arg Gly Asp Tyr Gly Asp Tyr Glu Gly Trp Tyr Phe Asp Val
1               5                   10                  15

<210> SEQ ID NO 9

```
<211> LENGTH: 14
<212> TYPE: PRT
<213> ORGANISM: Artificial
<220> FEATURE:
<223> OTHER INFORMATION: Synthetic polypeptide

<400> SEQUENCE: 9

Arg Gly Asp Tyr Gly Asp Tyr Glu Gly Trp Tyr Phe Asp Val
1               5                   10

<210> SEQ ID NO 10
<211> LENGTH: 16
<212> TYPE: PRT
<213> ORGANISM: Artificial
<220> FEATURE:
<223> OTHER INFORMATION: Synthetic polypeptide

<400> SEQUENCE: 10

Ala Arg Arg Gly Asp Tyr Gly Asp Tyr Glu Gly Trp Tyr Phe Asp Val
1               5                   10                  15

<210> SEQ ID NO 11
<211> LENGTH: 321
<212> TYPE: DNA
<213> ORGANISM: Artificial
<220> FEATURE:
<223> OTHER INFORMATION: Synthetic polynucleotide

<400> SEQUENCE: 11
gacatccaga tgaaccagtc tccatccagt ctgtctgcat cccttggaga cacaattacc      60
atcacttgcc atgccagtca gaacattaat gtttggttaa gctggtacca gcagaaacca     120
ggaaatattc ctaaactatt gatctataag gcttccaact tgcacacagg cgtcccatca     180
aggtttagtg gcagtggatc tggaacaggt ttcacattaa ccatcagcag cctgcagcct     240
gaagacattg ccacttacta ctgtcaacag ggtcaaagtt atccgtacac gttcggaggg     300
gggaccaagc tggaaataaa a                                               321

<210> SEQ ID NO 12
<211> LENGTH: 107
<212> TYPE: PRT
<213> ORGANISM: Artificial
<220> FEATURE:
<223> OTHER INFORMATION: Synthetic polypeptide

<400> SEQUENCE: 12

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 13
```

```
<211> LENGTH: 6
<212> TYPE: PRT
<213> ORGANISM: Artificial
<220> FEATURE:
<223> OTHER INFORMATION: Synthetic polypeptide

<400> SEQUENCE: 13

Gln Asn Ile Asn Val Trp
1               5

<210> SEQ ID NO 14
<211> LENGTH: 11
<212> TYPE: PRT
<213> ORGANISM: Artificial
<220> FEATURE:
<223> OTHER INFORMATION: Synthetic polypeptide

<400> SEQUENCE: 14

His Ala Ser Gln Asn Ile Asn Val Trp Leu Ser
1               5                   10

<210> SEQ ID NO 15
<211> LENGTH: 7
<212> TYPE: PRT
<213> ORGANISM: artificial
<220> FEATURE:
<223> OTHER INFORMATION: Synthetic polypeptide

<400> SEQUENCE: 15

Lys Ala Ser Asn Leu His Thr
1               5

<210> SEQ ID NO 16
<211> LENGTH: 9
<212> TYPE: PRT
<213> ORGANISM: artificial
<220> FEATURE:
<223> OTHER INFORMATION: Synthetic polypeptide

<400> SEQUENCE: 16

Gln Gln Gly Gln Ser Tyr Pro Tyr Thr
1               5

<210> SEQ ID NO 17
<211> LENGTH: 9
<212> TYPE: PRT
<213> ORGANISM: Artificial
<220> FEATURE:
<223> OTHER INFORMATION: Synthetic polypeptide

<400> SEQUENCE: 17

Gln Gln Gly Gln Ser Tyr Pro Tyr Thr
1               5

<210> SEQ ID NO 18
<211> LENGTH: 369
<212> TYPE: DNA
<213> ORGANISM: Artificial
<220> FEATURE:
<223> OTHER INFORMATION: Synthetic polynucleotide

<400> SEQUENCE: 18
cagattcagc tggttcagtc tggcgccgaa gtgaagaaac ctggcgcctc tgtgaaggtg     60
tcctgcaagg ccagcggcta cagcttcacc ggctacaaca tgaactgggt ccgacaggcc    120
cctggcaaga gcctggaatg gatcggcgac atcaacccct actacggcgc caccacctac    180
```

```
aaccagaaat tcaagggcag agtgaccctg accgtggaca ccagcacaag caccgcctac    240
atggaactga gcagcctgag aagcgaggac accgccgtgt actactgtgc cagaagaggc    300
gactacggcg attacgaagg ctggtacttc gacgtgtggg gccagggcac aatggtcaca    360
gttagctct                                                            369
```

<210> SEQ ID NO 19
<211> LENGTH: 123
<212> TYPE: PRT
<213> ORGANISM: Artificial
<220> FEATURE:
<223> OTHER INFORMATION: Synthetic polypeptide

<400> SEQUENCE: 19

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Lys Ser Leu Glu Trp Ile
        35                  40                  45

Gly Asp Ile Asn Pro Tyr Tyr Gly Ala Thr Thr Tyr Asn Gln Lys Phe
    50                  55                  60

Lys Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Gln Gly Thr Met Val Thr Val Ser Ser
        115                 120
```

<210> SEQ ID NO 20
<211> LENGTH: 321
<212> TYPE: DNA
<213> ORGANISM: artificial
<220> FEATURE:
<223> OTHER INFORMATION: Synthetic polynucleotide

<400> SEQUENCE: 20

```
gacatccaga tgacacagag ccccagcagc ctgtctgcct ctgtgggaga cagagtgacc     60
atcacctgtc acgccagcca gaacatcaac gtgtggctga gctggtatca gcagaagcct    120
ggcaacgccc taagctgct gatctacaag gccagcaatc tgcacaccgg cgtgcccagc     180
agattttctg gctctggcag cggcaccgac ttcaccctga ccatatctag cctgcagcct    240
gaggacattg ccacctacta ctgtcagcag ggccagagct accccctaca atttggcgga    300
ggcaccaagc tggaaatcaa g                                              321
```

<210> SEQ ID NO 21
<211> LENGTH: 107
<212> TYPE: PRT
<213> ORGANISM: artificial
<220> FEATURE:
<223> OTHER INFORMATION: Synthetic polypeptide

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30
```

```
Leu Ser Trp Tyr Gln Gln Lys Pro Gly Asn Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105
```

<210> SEQ ID NO 22
<211> LENGTH: 369
<212> TYPE: DNA
<213> ORGANISM: artificial
<220> FEATURE:
<223> OTHER INFORMATION: Synthetic polynucleotide

<400> SEQUENCE: 22

```
gagattcagc tgcagcagtc tggcgccgaa gtgaagaaac ctggcgcctc cgtgaagatc      60
agctgtgaag ccagcggcta cagcttcacc ggctacaaca tgaactgggt caagcaggcc    120
cctggcaaga gcctggaatg gatcggcgac atcaacccct actacggcgc caccacctac    180
aaccagaagt tcaagggcag agccacactg accgtggaca ccagcacaag caccgcctac    240
atggaactga gcagcctgag aagcgaggac accgccgtgt actactgtgc cagaagaggc    300
gactacggcg attacgaagg ctggtacttc gacgtgtggg gccagggcac aatggtcaca    360
gttagctct                                                            369
```

<210> SEQ ID NO 23
<211> LENGTH: 123
<212> TYPE: PRT
<213> ORGANISM: artificial
<220> FEATURE:
<223> OTHER INFORMATION: Synthetic polypeptide

<400> SEQUENCE: 23

```
Glu Ile Gln Leu Gln Gln Ser Gly Ala Glu Val Lys Lys Pro Gly Ala
1               5                   10                  15

Ser Val Lys Ile Ser Cys Glu Ala Ser Gly Tyr Ser Phe Thr Gly Tyr
            20                  25                  30

Asn Met Asn Trp Val Lys Gln Ala Pro Gly Lys Ser Leu Glu Trp Ile
        35                  40                  45

Gly Asp Ile Asn Pro Tyr Tyr Gly Ala Thr Thr Tyr Asn Gln Lys Phe
    50                  55                  60

Lys Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Gln Gly Thr Met Val Thr Val Ser Ser
        115                 120
```

<210> SEQ ID NO 24
<211> LENGTH: 321
<212> TYPE: DNA
<213> ORGANISM: artificial

```
<220> FEATURE:
<223> OTHER INFORMATION: Synthetic polynucleotide

<400> SEQUENCE: 24
gacatccaga tgacacagag ccccagcagc ctgtctgcct ctgtgggaga cagagtgacc    60
atcacctgtc acgccagcca gaacatcaac gtgtggctga gctggtatca gcagaagcct   120
ggcaacgccc ctaagctgct gatctacaag gccagcaatc tgcacaccgg cgtgcccagc   180
agattttctg gctctggcag cggcaccgac ttcaccttca ccatatctag cctgcagcct   240
gaggacattg ccacctacta ctgtcagcag ggccagagct accccctaca atttggcgga   300
ggcaccaagc tggaaatcaa g                                             321

<210> SEQ ID NO 25
<211> LENGTH: 107
<212> TYPE: PRT
<213> ORGANISM: artificial
<220> FEATURE:
<223> OTHER INFORMATION: Synthetic polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Asn Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105

<210> SEQ ID NO 26
<211> LENGTH: 363
<212> TYPE: DNA
<213> ORGANISM: artificial
<220> FEATURE:
<223> OTHER INFORMATION: Synthetic polynucleotide

<400> SEQUENCE: 26
gatgttcaac tccagcagtc tgggactgtg ctggcacggc ctggggcttc agtgaagatg    60
tcctgcaagg cttctggcta cacctttacc agctactgga tacactgggt aaaacagagg   120
cctggacagg gtctggaatg gattggcgct atttatcctg gaaatagaga tactaactac   180
aaccagaagt tcaagggcaa ggccaaactg actacagtca catctgccag cactgcctac   240
atggagctca gcagcctgac aaatgaggac tctgcggtct attactgtac gggggccttt   300
gctggttact acgactggta cttcgatgtc tggggcgcag gaccacggt caccgtctcc   360 tca                                                                 363

<210> SEQ ID NO 27
<211> LENGTH: 121
<212> TYPE: PRT
<213> ORGANISM: artificial
<220> FEATURE:
<223> OTHER INFORMATION: Synthetic polypeptide
```

<400> SEQUENCE: 27

Asp Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Ala Ile Tyr Pro Gly Asn Arg Asp Thr Asn Tyr Asn Gln Lys Phe
    50                  55                  60

Lys Gly Lys Ala Lys Leu Thr Thr Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Gly Ala Phe Ala Gly Tyr Tyr Asp Trp Tyr Phe Asp Val Trp Gly
            100                 105                 110

Ala Gly Thr Thr Val Thr Val Ser Ser
        115                 120

<210> SEQ ID NO 28
<211> LENGTH: 8
<212> TYPE: PRT
<213> ORGANISM: artificial
<220> FEATURE:
<223> OTHER INFORMATION: Synthetic polypeptide

<400> SEQUENCE: 28

Gly Tyr Thr Phe Thr Ser Tyr Trp
1               5

<210> SEQ ID NO 29
<211> LENGTH: 5
<212> TYPE: PRT
<213> ORGANISM: Artificial
<220> FEATURE:
<223> OTHER INFORMATION: Synthetic polypeptide

<400> SEQUENCE: 29

Ser Tyr Trp Ile His
1               5

<210> SEQ ID NO 30
<211> LENGTH: 10
<212> TYPE: PRT
<213> ORGANISM: Artificial
<220> FEATURE:
<223> OTHER INFORMATION: Synthetic polypeptide

<400> SEQUENCE: 30

Gly Tyr Thr Phe Thr Ser Tyr Trp Ile His
1               5                   10

<210> SEQ ID NO 31
<211> LENGTH: 8
<212> TYPE: PRT
<213> ORGANISM: artificial
<220> FEATURE:
<223> OTHER INFORMATION: Synthetic polypeptide

<400> SEQUENCE: 31

Ile Tyr Pro Gly Asn Arg Asp Thr
1               5

<210> SEQ ID NO 32
<211> LENGTH: 17
<212> TYPE: PRT
<213> ORGANISM: Artificial
<220> FEATURE:
<223> OTHER INFORMATION: Synthetic polypeptide

<400> SEQUENCE: 32

Ala Ile Tyr Pro Gly Asn Arg Asp Thr Asn Tyr Asn Gln Lys Phe Lys
1               5                   10                  15

Gly

<210> SEQ ID NO 33
<211> LENGTH: 14
<212> TYPE: PRT
<213> ORGANISM: artificial
<220> FEATURE:
<223> OTHER INFORMATION: Synthetic polypeptide

<400> SEQUENCE: 33

Thr Gly Ala Phe Ala Gly Tyr Tyr Asp Trp Tyr Phe Asp Val
1               5                   10

<210> SEQ ID NO 34
<211> LENGTH: 12
<212> TYPE: PRT
<213> ORGANISM: Artificial
<220> FEATURE:
<223> OTHER INFORMATION: Synthetic polypeptide

<400> SEQUENCE: 34

Ala Phe Ala Gly Tyr Tyr Asp Trp Tyr Phe Asp Val
1               5                   10

<210> SEQ ID NO 35
<211> LENGTH: 333
<212> TYPE: DNA
<213> ORGANISM: artificial
<220> FEATURE:
<223> OTHER INFORMATION: Synthetic polynucleotide

<400> SEQUENCE: 35
gacattgtgc tgacccaatc tccagcttct ttggctgtgt ctctagggca gagggccacc      60
atctcctgca aggccagcca aggtgttgat tatgctggtg atagttatat gaactggtac     120
caacagaaac aggacagcc acccaaactc ctcatctatg ttgcatccga tctggattct     180
gggatcccag ccaggtttag tggcagtggg tctgggacaa acttcaccct caacatccat     240
cctgtggagg aggaggatgc tgcaacctat tactgtcagc aaagttatga ggatcctcgg     300
acgttcggtg aggcaccac gctggaaatc caa                                   333

<210> SEQ ID NO 36
<211> LENGTH: 111
<212> TYPE: PRT
<213> ORGANISM: artificial
<220> FEATURE:
<223> OTHER INFORMATION: Synthetic polypeptide

<400> SEQUENCE: 36

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Gly Val Asp Tyr Ala
            20                  25                  30

```
Gly Asp Ser Tyr Met Asn Trp Tyr Gln Gln Lys Pro Gly Gln Pro Pro
            35                  40                  45

Lys Leu Leu Ile Tyr Val Ala Ser Asp Leu Asp Ser Gly Ile Pro Ala
 50                  55                  60

Arg Phe Ser Gly Ser Gly Ser Gly Thr Asn Phe Thr Leu Asn Ile His
 65                  70                  75                  80

Pro Val Glu Glu Glu Asp Ala Ala Thr Tyr Tyr Cys Gln Gln Ser Tyr
                 85                  90                  95

Glu Asp Pro Arg Thr Phe Gly Gly Gly Thr Thr Leu Glu Ile Gln
            100                 105                 110
```

<210> SEQ ID NO 37
<211> LENGTH: 10
<212> TYPE: PRT
<213> ORGANISM: artificial
<220> FEATURE:
<223> OTHER INFORMATION: Synthetic polypeptide

<400> SEQUENCE: 37

```
Gln Gly Val Asp Tyr Ala Gly Asp Ser Tyr
 1               5                  10
```

<210> SEQ ID NO 38
<211> LENGTH: 15
<212> TYPE: PRT
<213> ORGANISM: Artificial
<220> FEATURE:
<223> OTHER INFORMATION: Synthetic polypeptide

<400> SEQUENCE: 38

```
Lys Ala Ser Gln Gly Val Asp Tyr Ala Gly Asp Ser Tyr Met Asn
 1               5                  10                  15
```

<210> SEQ ID NO 39
<211> LENGTH: 7
<212> TYPE: PRT
<213> ORGANISM: artificial
<220> FEATURE:
<223> OTHER INFORMATION: Synthetic polypeptide

<400> SEQUENCE: 39

```
Val Ala Ser Asp Leu Asp Ser
 1               5
```

<210> SEQ ID NO 40
<211> LENGTH: 9
<212> TYPE: PRT
<213> ORGANISM: artificial
<220> FEATURE:
<223> OTHER INFORMATION: Synthetic polypeptide

<400> SEQUENCE: 40

```
Gln Gln Ser Tyr Glu Asp Pro Arg Thr
 1               5
```

<210> SEQ ID NO 41
<211> LENGTH: 9
<212> TYPE: PRT
<213> ORGANISM: Artificial
<220> FEATURE:
<223> OTHER INFORMATION: Synthetic polypeptide

<400> SEQUENCE: 41

```
Gln Gln Ser Tyr Glu Asp Pro Arg Thr
 1               5
```

<210> SEQ ID NO 42
<211> LENGTH: 363
<212> TYPE: DNA
<213> ORGANISM: artificial
<220> FEATURE:
<223> OTHER INFORMATION: Synthetic polynucleotide

<400> SEQUENCE: 42

```
caagttcagc tgcagcagtc tggcgccgaa gtgaaaaaac tggcgcctc cgtgaagatg        60 agctgcaagg ccagcggcta ccttcacc agctactgga ttcactgggt ccgacaggcc      120
cctggacaag gcttggaatg gatgggcgcc atctatcccg gcaaccggga caccaactac      180
aaccagaaat tcaagggcag agtgaccctg accaccgaca catctgccag caccgcctac      240
atggaactga gcagcctgag aagcgaggac accgccgtgt actactgtac aggcgccttt      300
gccggctact acgactggta ctttgacgtg tggggccagg gcaccaccgt gacagttagt      360
tct                                                                   363
```

<210> SEQ ID NO 43
<211> LENGTH: 121
<212> TYPE: PRT
<213> ORGANISM: artificial
<220> FEATURE:
<223> OTHER INFORMATION: Synthetic polypeptide

<400> SEQUENCE: 43

```
Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Ala Ile Tyr Pro Gly Asn Arg Asp Thr Asn Tyr Asn Gln Lys Phe
    50                  55                  60

Lys Gly Arg Val Thr Leu Thr Thr Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Gly Ala Phe Ala Gly Tyr Tyr Asp Trp Tyr Phe Asp Val Trp Gly
            100                 105                 110

Gln Gly Thr Thr Val Thr Val Ser Ser
        115                 120
```

<210> SEQ ID NO 44
<211> LENGTH: 333
<212> TYPE: DNA
<213> ORGANISM: artificial
<220> FEATURE:
<223> OTHER INFORMATION: Synthetic polynucleotide

<400> SEQUENCE: 44

```
gacattgtgc tgacacagag ccccgatagc ctggccgtgt ctctgggaga aagagccacc        60
atcaactgca aggccagcca gggcgttgac tacgccggcg acagctacat gaactggtat      120
cagcagaagc ccggccagcc tcctaagctg ctgatctacg tggccagcga tctggacagc      180 ggcatcccg atagatttc cggctctggc tccggcaccg acttcaccct acaatcagt        240 tccctgcagg ccgaggacgt ggccacctac tattgtcagc agagctacga ggaccccga        300
``` accttttggcg gcggaaccac actggaaatc aag    333

<210> SEQ ID NO 45
<211> LENGTH: 111
<212> TYPE: PRT
<213> ORGANISM: artificial
<220> FEATURE:
<223> OTHER INFORMATION: Synthetic polypeptide

<400> SEQUENCE: 45

```
Asp Ile Val Leu Thr Gln Ser Pro Asp Ser Leu Ala Val Ser Leu Gly
1               5                   10                  15
Glu Arg Ala Thr Ile Asn Cys Lys Ala Ser Gln Gly Val Asp Tyr Ala
            20                  25                  30
Gly Asp Ser Tyr Met Asn Trp Tyr Gln Gln Lys Pro Gly Gln Pro Pro
        35                  40                  45
Lys Leu Leu Ile Tyr Val Ala Ser Asp Leu Asp Ser Gly Ile Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Thr Tyr Tyr Cys Gln Gln Ser Tyr
                85                  90                  95
Glu Asp Pro Arg Thr Phe Gly Gly Gly Thr Thr Leu Glu Ile Lys
            100                 105                 110
```

<210> SEQ ID NO 46
<211> LENGTH: 364
<212> TYPE: DNA
<213> ORGANISM: artificial
<220> FEATURE:
<223> OTHER INFORMATION: Synthetic polynucleotide

<400> SEQUENCE: 46
caagttcagc tgcagcagtc tggcgccgtg gtcaaaaaac ctggcgcctc cgtgaagatg    60
agctgcaagg ccagcggcta caccttcacc agctactgga ttcactgggt caagcaggcc   120
cctggacagg gccttgaatg gatcggagcc atctatcccg gcaaccggga caccaactac   180
aaccagaagt tcaagggcag agccacactg accaccgata cctctgccag caccgcctac   240
atggaactga gcagcctgac cagcgaggac accgccgtgt attactgtac aggcgccttc   300
gccggctact acgactggta ctttgatgtg tggggccagg gcaccaccgt gacagttagt   360
tctg   364

<210> SEQ ID NO 47
<211> LENGTH: 121
<212> TYPE: PRT
<213> ORGANISM: artificial
<220> FEATURE:
<223> OTHER INFORMATION: Synthetic polypeptide

<400> SEQUENCE: 47

```
Gln Val Gln Leu Gln Gln Ser Gly Ala Val Val Lys Lys Pro Gly Ala
1               5                   10                  15
Ser Val Lys Met Ser Cys Lys Ala Ser Gly Tyr Thr Phe Thr Ser Tyr
            20                  25                  30
Trp Ile His Trp Val Lys Gln Ala Pro Gly Gln Gly Leu Glu Trp Ile
        35                  40                  45
Gly Ala Ile Tyr Pro Gly Asn Arg Asp Thr Asn Tyr Asn Gln Lys Phe
    50                  55                  60
```

```
Lys Gly Arg Ala Thr Leu Thr Thr Asp Thr Ser Ala Ser Thr Ala Tyr
 65                  70                  75                  80

Met Glu Leu Ser Ser Leu Thr Ser Glu Asp Thr Ala Val Tyr Tyr Cys
                 85                  90                  95

Thr Gly Ala Phe Ala Gly Tyr Tyr Asp Trp Tyr Phe Asp Val Trp Gly
            100                 105                 110

Gln Gly Thr Thr Val Thr Val Ser Ser
        115                 120

<210> SEQ ID NO 48
<211> LENGTH: 333
<212> TYPE: DNA
<213> ORGANISM: artificial
<220> FEATURE:
<223> OTHER INFORMATION: Synthetic polynucleotide

<400> SEQUENCE: 48
gacattgtgc tgacacagag ccccgatagc ctggccgtgt ctctgggaga aagagccacc    60
atcaactgca aggccagcca gggcgttgac tacgccggcg acagctacat gaactggtat   120
cagcagaagc ccggccagcc tcctaagctg ctgatctacg tggccagcga tctggatagc   180
ggcgtgcccg atagattttc tggcagcggc tctggcaccg acttcaccct gacaattagc   240
tccctgcagg ccgaggatgt ggccacctac tactgtcagc agagctacga ggaccccaga   300
acctttggcg gcggaaccac actggaaatc aag                                333

<210> SEQ ID NO 49
<211> LENGTH: 111
<212> TYPE: PRT
<213> ORGANISM: artificial
<220> FEATURE:
<223> OTHER INFORMATION: Synthetic polypeptide

<400> SEQUENCE: 49

Asp Ile Val Leu Thr Gln Ser Pro Asp Ser Leu Ala Val Ser Leu Gly
  1               5                  10                  15

Glu Arg Ala Thr Ile Asn Cys Lys Ala Ser Gln Gly Val Asp Tyr Ala
             20                  25                  30

Gly Asp Ser Tyr Met Asn Trp Tyr Gln Gln Lys Pro Gly Gln Pro Pro
         35                  40                  45

Lys Leu Leu Ile Tyr Val Ala Ser Asp Leu Asp Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Thr Tyr Tyr Cys Gln Gln Ser Tyr
                 85                  90                  95

Glu Asp Pro Arg Thr Phe Gly Gly Gly Thr Thr Leu Glu Ile Lys
            100                 105                 110

<210> SEQ ID NO 50
<211> LENGTH: 628
<212> TYPE: PRT
<213> ORGANISM: artificial
<220> FEATURE:
<223> OTHER INFORMATION: Synthetic polypeptide

<400> SEQUENCE: 50

Glu Ile Gln Leu Gln Gln Ser Gly Ala Glu Leu Val Lys Pro Arg Ala
  1               5                  10                  15

Ser Val Lys Ile Ser Cys Glu Ala Ser Gly Tyr Ser Phe Thr Gly Tyr
```

```
            20                  25                  30
Asn Met Asn Trp Val Lys Gln Ser Pro Gly Lys Ser Leu Glu Trp Ile
        35                  40                  45

Gly Asp Ile Asn Pro Tyr Tyr Gly Ala Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Ala Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445
```

```
Leu Ser Pro Gly Lys Leu Gly Gly Gly Gly Gly Gly Ser
    450                 455                 460

Gly Gly Gly Gly Ser Pro Gly Gln Gly Thr Gln Ser Glu Asn Ser Cys
465                 470                 475                 480

Thr His Phe Pro Gly Asn Leu Pro Asn Met Leu Arg Asp Leu Arg Asp
                485                 490                 495

Ala Phe Ser Arg Val Lys Thr Phe Phe Gln Met Lys Asp Gln Leu Asp
                500                 505                 510

Asn Leu Leu Lys Glu Ser Leu Leu Glu Asp Phe Lys Gly Tyr Leu
            515                 520                 525

Gly Cys Gln Ala Leu Ser Glu Met Ile Gln Phe Tyr Leu Glu Glu Val
530                 535                 540

Met Pro Gln Ala Glu Asn Gln Asp Pro Asp Ile Lys Ala His Val Asn
545                 550                 555                 560

Ser Leu Gly Glu Asn Leu Lys Thr Leu Arg Leu Arg Leu Arg Arg Cys
                565                 570                 575

His Arg Phe Leu Pro Cys Glu Asn Lys Ser Lys Ala Val Glu Gln Val
                580                 585                 590

Lys Asn Ala Phe Asn Lys Leu Gln Glu Lys Gly Ile Tyr Lys Ala Met
            595                 600                 605

Ser Glu Phe Asp Ile Phe Ile Asn Tyr Ile Glu Ala Tyr Met Thr Met
610                 615                 620

Lys Ile Arg Asn
625

<210> SEQ ID NO 51
<211> LENGTH: 802
<212> TYPE: PRT
<213> ORGANISM: artificial
<220> FEATURE:
<223> OTHER INFORMATION: Synthetic polypeptide

<400> SEQUENCE: 51

Glu Ile Gln Leu Gln Gln Ser Gly Ala Glu Leu Val Lys Pro Arg Ala
1               5                   10                  15

Ser Val Lys Ile Ser Cys Glu Ala Ser Gly Tyr Ser Phe Thr Gly Tyr
                20                  25                  30

Asn Met Asn Trp Val Lys Gln Ser Pro Gly Lys Ser Leu Glu Trp Ile
            35                  40                  45

Gly Asp Ile Asn Pro Tyr Tyr Gly Ala Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Gly Asp Tyr Gly Asp Tyr Glu Gly Trp Tyr Phe Asp Val
                100                 105                 110

Trp Gly Ala Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Leu Gly Gly Gly Ser Gly Gly Gly Gly Ser
450                 455                 460

Gly Gly Gly Gly Ser Pro Gly Gln Gly Thr Gln Ser Glu Asn Ser Cys
465                 470                 475                 480

Thr His Phe Pro Gly Asn Leu Pro Asn Met Leu Arg Asp Leu Arg Asp
                485                 490                 495

Ala Phe Ser Arg Val Lys Thr Phe Phe Gln Met Lys Asp Gln Leu Asp
            500                 505                 510

Asn Leu Leu Leu Lys Glu Ser Leu Leu Glu Asp Phe Lys Gly Tyr Leu
        515                 520                 525

Gly Cys Gln Ala Leu Ser Glu Met Ile Gln Phe Tyr Leu Glu Glu Val
    530                 535                 540

Met Pro Gln Ala Glu Asn Gln Asp Pro Asp Ile Lys Ala His Val Asn
545                 550                 555                 560

Ser Leu Gly Glu Asn Leu Lys Thr Leu Arg Leu Arg Leu Arg Arg Cys
                565                 570                 575

His Arg Phe Leu Pro Cys Glu Asn Lys Ser Lys Ala Val Glu Gln Val
            580                 585                 590
```

```
Lys Asn Ala Phe Asn Lys Leu Gln Glu Lys Gly Ile Tyr Lys Ala Met
            595                 600                 605

Ser Glu Phe Asp Ile Phe Ile Asn Tyr Ile Glu Ala Tyr Met Thr Met
610                 615                 620

Lys Ile Arg Asn Gly Gly Gly Ser Gly Gly Gly Gly Ser Gly Gly
625                 630                 635                 640

Gly Gly Ser Pro Gly Gln Gly Thr Gln Ser Glu Asn Ser Cys Thr His
                645                 650                 655

Phe Pro Gly Asn Leu Pro Asn Met Leu Arg Asp Leu Arg Asp Ala Phe
            660                 665                 670

Ser Arg Val Lys Thr Phe Phe Gln Met Lys Asp Gln Leu Asp Asn Leu
            675                 680                 685

Leu Leu Lys Glu Ser Leu Leu Glu Asp Phe Lys Gly Tyr Leu Gly Cys
            690                 695                 700

Gln Ala Leu Ser Glu Met Ile Gln Phe Tyr Leu Glu Glu Val Met Pro
705                 710                 715                 720

Gln Ala Glu Asn Gln Asp Pro Asp Ile Lys Ala His Val Asn Ser Leu
                725                 730                 735

Gly Glu Asn Leu Lys Thr Leu Arg Leu Arg Leu Arg Arg Cys His Arg
            740                 745                 750

Phe Leu Pro Cys Glu Asn Lys Ser Lys Ala Val Glu Gln Val Lys Asn
            755                 760                 765

Ala Phe Asn Lys Leu Gln Glu Lys Gly Ile Tyr Lys Ala Met Ser Glu
            770                 775                 780

Phe Asp Ile Phe Ile Asn Tyr Ile Glu Ala Tyr Met Thr Met Lys Ile
785                 790                 795                 800

Arg Asn

<210> SEQ ID NO 52
<211> LENGTH: 628
<212> TYPE: PRT
<213> ORGANISM: artificial
<220> FEATURE:
<223> OTHER INFORMATION: Synthetic polypeptide

<400> SEQUENCE: 52

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Asn Met Asn Trp Val Arg Gln Ala Pro Gly Lys Ser Leu Glu Trp Ile
            35                  40                  45

Gly Asp Ile Asn Pro Tyr Tyr Gly Ala Thr Thr Tyr Asn Gln Lys Phe
        50                  55                  60

Lys Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
```

-continued

```
            145                 150                 155                 160
        Thr Val Ser Trp Asn Ser Gly Ala Leu Thr Ser Gly Val His Thr Phe
                        165                 170                 175
        Pro Ala Val Leu Gln Ser Ser Gly Leu Tyr Ser Leu Ser Ser Val Val
                        180                 185                 190
        Thr Val Pro Ser Ser Ser Leu Gly Thr Gln Thr Tyr Ile Cys Asn Val
                        195                 200                 205
        Asn His Lys Pro Ser Asn Thr Lys Val Asp Lys Lys Val Glu Pro Lys
                        210                 215                 220
        Ser Cys Asp Lys Thr His Thr Cys Pro Pro Cys Pro Ala Pro Glu Leu
        225                 230                 235                 240
        Leu Gly Gly Pro Ser Val Phe Leu Phe Pro Pro Lys Pro Lys Asp Thr
                        245                 250                 255
        Leu Met Ile Ser Arg Thr Pro Glu Val Thr Cys Val Val Val Asp Val
                        260                 265                 270
        Ser His Glu Asp Pro Glu Val Lys Phe Asn Trp Tyr Val Asp Gly Val
                        275                 280                 285
        Glu Val His Asn Ala Lys Thr Lys Pro Arg Glu Glu Gln Tyr Asn Ser
                        290                 295                 300
        Thr Tyr Arg Val Val Ser Val Leu Thr Val Leu His Gln Asp Trp Leu
        305                 310                 315                 320
        Asn Gly Lys Glu Tyr Lys Cys Lys Val Ser Asn Lys Ala Leu Pro Ala
                        325                 330                 335
        Pro Ile Glu Lys Thr Ile Ser Lys Ala Lys Gly Gln Pro Arg Glu Pro
                        340                 345                 350
        Gln Val Tyr Thr Leu Pro Pro Ser Arg Glu Glu Met Thr Lys Asn Gln
                        355                 360                 365
        Val Ser Leu Thr Cys Leu Val Lys Gly Phe Tyr Pro Ser Asp Ile Ala
        370                 375                 380
        Val Glu Trp Glu Ser Asn Gly Gln Pro Glu Asn Asn Tyr Lys Thr Thr
        385                 390                 395                 400
        Pro Pro Val Leu Asp Ser Asp Gly Ser Phe Phe Leu Tyr Ser Lys Leu
                        405                 410                 415
        Thr Val Asp Lys Ser Arg Trp Gln Gln Gly Asn Val Phe Ser Cys Ser
                        420                 425                 430
        Val Met His Glu Ala Leu His Asn His Tyr Thr Gln Lys Ser Leu Ser
                        435                 440                 445
        Leu Ser Pro Gly Lys Leu Gly Gly Gly Ser Gly Gly Gly Gly Ser
        450                 455                 460
        Gly Gly Gly Gly Ser Pro Gly Gln Gly Thr Gln Ser Glu Asn Ser Cys
        465                 470                 475                 480
        Thr His Phe Pro Gly Asn Leu Pro Asn Met Leu Arg Asp Leu Arg Asp
                        485                 490                 495
        Ala Phe Ser Arg Val Lys Thr Phe Phe Gln Met Lys Asp Gln Leu Asp
                        500                 505                 510
        Asn Leu Leu Leu Lys Glu Ser Leu Leu Glu Asp Phe Lys Gly Tyr Leu
                        515                 520                 525
        Gly Cys Gln Ala Leu Ser Glu Met Ile Gln Phe Tyr Leu Glu Glu Val
                        530                 535                 540
        Met Pro Gln Ala Glu Asn Gln Asp Pro Asp Ile Lys Ala His Val Asn
        545                 550                 555                 560
        Ser Leu Gly Glu Asn Leu Lys Thr Leu Arg Leu Arg Leu Arg Arg Cys
                        565                 570                 575
```

His Arg Phe Leu Pro Cys Glu Asn Lys Ser Lys Ala Val Glu Gln Val
            580                 585                 590

Lys Asn Ala Phe Asn Lys Leu Gln Glu Lys Gly Ile Tyr Lys Ala Met
            595                 600                 605

Ser Glu Phe Asp Ile Phe Ile Asn Tyr Ile Glu Ala Tyr Met Thr Met
            610                 615                 620

Lys Ile Arg Asn
625

<210> SEQ ID NO 53
<211> LENGTH: 628
<212> TYPE: PRT
<213> ORGANISM: artificial
<220> FEATURE:
<223> OTHER INFORMATION: Synthetic polypeptide

<400> SEQUENCE: 53

Glu Ile Gln Leu Gln Gln Ser Gly Ala Glu Val Lys Lys Pro Gly Ala
1               5                   10                  15

Ser Val Lys Ile Ser Cys Glu Ala Ser Gly Tyr Ser Phe Thr Gly Tyr
            20                  25                  30

Asn Met Asn Trp Val Lys Gln Ala Pro Gly Lys Ser Leu Glu Trp Ile
            35                  40                  45

Gly Asp Ile Asn Pro Tyr Tyr Gly Ala Thr Thr Tyr Asn Gln Lys Phe
50                  55                  60

Lys Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Gly Asp Tyr Gly Asp Tyr Glu Gly Trp Tyr Phe Asp Val
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Leu Gly Gly Gly Ser Gly Gly Gly Gly Ser
450                 455                 460

Gly Gly Gly Gly Ser Pro Gly Gln Gly Thr Gln Ser Glu Asn Ser Cys
465                 470                 475                 480

Thr His Phe Pro Gly Asn Leu Pro Asn Met Leu Arg Asp Leu Arg Asp
            485                 490                 495

Ala Phe Ser Arg Val Lys Thr Phe Phe Gln Met Lys Asp Gln Leu Asp
            500                 505                 510

Asn Leu Leu Leu Lys Glu Ser Leu Leu Glu Asp Phe Lys Gly Tyr Leu
            515                 520                 525

Gly Cys Gln Ala Leu Ser Glu Met Ile Gln Phe Tyr Leu Glu Glu Val
            530                 535                 540

Met Pro Gln Ala Glu Asn Gln Asp Pro Asp Ile Lys Ala His Val Asn
545                 550                 555                 560

Ser Leu Gly Glu Asn Leu Lys Thr Leu Arg Leu Arg Leu Arg Arg Cys
            565                 570                 575

His Arg Phe Leu Pro Cys Glu Asn Lys Ser Lys Ala Val Glu Gln Val
            580                 585                 590

Lys Asn Ala Phe Asn Lys Leu Gln Glu Lys Gly Ile Tyr Lys Ala Met
            595                 600                 605

Ser Glu Phe Asp Ile Phe Ile Asn Tyr Ile Glu Ala Tyr Met Thr Met
            610                 615                 620

Lys Ile Arg Asn
625

<210> SEQ ID NO 54
<211> LENGTH: 626
<212> TYPE: PRT
<213> ORGANISM: artificial
<220> FEATURE:
<223> OTHER INFORMATION: Synthetic polypeptide

<400> SEQUENCE: 54

Asp Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30
```

```
Trp Ile His Trp Val Lys Gln Arg Pro Gly Gln Gly Leu Glu Trp Ile
         35                  40                  45
Gly Ala Ile Tyr Pro Gly Asn Arg Asp Thr Asn Tyr Asn Gln Lys Phe
     50                  55                  60
Lys Gly Lys Ala Lys Leu Thr Thr Val Thr Ser Ala Ser Thr Ala Tyr
 65                  70                  75                  80
Met Glu Leu Ser Ser Leu Thr Asn Glu Asp Ser Ala Val Tyr Tyr Cys
                 85                  90                  95
Thr Gly Ala Phe Ala Gly Tyr Tyr Asp Trp Tyr Phe Asp Val Trp Gly
                100                 105                 110
Ala Gly Thr Thr Val Thr Val Ser Ser Ala Ser Thr Lys Gly Pro Ser
             115                 120                 125
Val Phe Pro Leu Ala Pro Ser Ser Lys Ser Thr Ser Gly Gly Thr Ala
         130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

```
Pro Gly Lys Leu Gly Gly Gly Ser Gly Gly Gly Ser Gly Gly
    450                 455                 460

Gly Gly Ser Pro Gly Gln Gly Thr Gln Ser Glu Asn Ser Cys Thr His
465                 470                 475                 480

Phe Pro Gly Asn Leu Pro Asn Met Leu Arg Asp Leu Arg Asp Ala Phe
                485                 490                 495

Ser Arg Val Lys Thr Phe Phe Gln Met Lys Asp Gln Leu Asp Asn Leu
            500                 505                 510

Leu Leu Lys Glu Ser Leu Leu Glu Asp Phe Lys Gly Tyr Leu Gly Cys
        515                 520                 525

Gln Ala Leu Ser Glu Met Ile Gln Phe Tyr Leu Glu Glu Val Met Pro
530                 535                 540

Gln Ala Glu Asn Gln Asp Pro Asp Ile Lys Ala His Val Asn Ser Leu
545                 550                 555                 560

Gly Glu Asn Leu Lys Thr Leu Arg Leu Arg Leu Arg Arg Cys His Arg
                565                 570                 575

Phe Leu Pro Cys Glu Asn Lys Ser Lys Ala Val Glu Gln Val Lys Asn
            580                 585                 590

Ala Phe Asn Lys Leu Gln Glu Lys Gly Ile Tyr Lys Ala Met Ser Glu
        595                 600                 605

Phe Asp Ile Phe Ile Asn Tyr Ile Glu Ala Tyr Met Thr Met Lys Ile
    610                 615                 620

Arg Asn
625

<210> SEQ ID NO 55
<211> LENGTH: 800
<212> TYPE: PRT
<213> ORGANISM: artificial
<220> FEATURE:
<223> OTHER INFORMATION: Synthetic polypeptide

<400> SEQUENCE: 55

Asp Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Ala Ile Tyr Pro Gly Asn Arg Asp Thr Asn Tyr Asn Gln Lys Phe
    50                  55                  60

Lys Gly Lys Ala Lys Leu Thr Thr Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Gly Ala Phe Ala Gly Tyr Tyr Asp Trp Tyr Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Leu Gly Gly Gly Ser Gly Gly Gly Ser Gly Gly
    450                 455                 460

Gly Gly Ser Pro Gly Gln Gly Thr Gln Ser Glu Asn Ser Cys Thr His
465                 470                 475                 480

Phe Pro Gly Asn Leu Pro Asn Met Leu Arg Asp Leu Arg Asp Ala Phe
                485                 490                 495

Ser Arg Val Lys Thr Phe Phe Gln Met Lys Asp Gln Leu Asp Asn Leu
            500                 505                 510

Leu Leu Lys Glu Ser Leu Leu Glu Asp Phe Lys Gly Tyr Leu Gly Cys
        515                 520                 525

Gln Ala Leu Ser Glu Met Ile Gln Phe Tyr Leu Glu Glu Val Met Pro
    530                 535                 540

Gln Ala Glu Asn Gln Asp Pro Asp Ile Lys Ala His Val Asn Ser Leu
545                 550                 555                 560

Gly Glu Asn Leu Lys Thr Leu Arg Leu Arg Leu Arg Arg Cys His Arg
                565                 570                 575

Phe Leu Pro Cys Glu Asn Lys Ser Lys Ala Val Glu Gln Val Lys Asn
            580                 585                 590

Ala Phe Asn Lys Leu Gln Glu Lys Gly Ile Tyr Lys Ala Met Ser Glu

```
              595                 600                 605
Phe Asp Ile Phe Ile Asn Tyr Ile Glu Ala Tyr Met Thr Met Lys Ile
610                 615                 620
Arg Asn Gly Gly Gly Ser Gly Gly Gly Ser Gly Gly Gly Gly
625                 630                 635                 640
Ser Pro Gly Gln Gly Thr Gln Ser Glu Asn Ser Cys Thr His Phe Pro
                645                 650                 655
Gly Asn Leu Pro Asn Met Leu Arg Asp Leu Arg Asp Ala Phe Ser Arg
                660                 665                 670
Val Lys Thr Phe Phe Gln Met Lys Asp Gln Leu Asp Asn Leu Leu Leu
                675                 680                 685
Lys Glu Ser Leu Leu Glu Asp Phe Lys Gly Tyr Leu Gly Cys Gln Ala
690                 695                 700
Leu Ser Glu Met Ile Gln Phe Tyr Leu Glu Glu Val Met Pro Gln Ala
705                 710                 715                 720
Glu Asn Gln Asp Pro Asp Ile Lys Ala His Val Asn Ser Leu Gly Glu
                725                 730                 735
Asn Leu Lys Thr Leu Arg Leu Arg Leu Arg Arg Cys His Arg Phe Leu
                740                 745                 750
Pro Cys Glu Asn Lys Ser Lys Ala Val Glu Gln Val Lys Asn Ala Phe
                755                 760                 765
Asn Lys Leu Gln Glu Lys Gly Ile Tyr Lys Ala Met Ser Glu Phe Asp
770                 775                 780
Ile Phe Ile Asn Tyr Ile Glu Ala Tyr Met Thr Met Lys Ile Arg Asn
785                 790                 795                 800

<210> SEQ ID NO 56
<211> LENGTH: 626
<212> TYPE: PRT
<213> ORGANISM: artificial
<220> FEATURE:
<223> OTHER INFORMATION: Synthetic polypeptide

<400> SEQUENCE: 56

Gln Val Gln Leu Gln Gln Ser Gly Ala Glu Val Lys Lys Pro Gly Ala
1               5                   10                  15
Ser Val Lys Met Ser Cys Lys Ala Ser Gly Tyr Thr Phe Thr Ser Tyr
                20                  25                  30
Trp Ile His Trp Val Arg Gln Ala Pro Gly Gln Gly Leu Glu Trp Met
            35                  40                  45
Gly Ala Ile Tyr Pro Gly Asn Arg Asp Thr Asn Tyr Asn Gln Lys Phe
        50                  55                  60
Lys Gly Arg Val Thr Leu Thr Thr Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Gly Ala Phe Ala Gly Tyr Tyr Asp Trp Tyr Phe Asp Val Trp Gly
                100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
```

```
            165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys Leu Gly Gly Gly Ser Gly Gly Gly Ser Gly Gly
            450                 455                 460
Gly Gly Ser Pro Gly Gln Gly Thr Gln Ser Glu Asn Ser Cys Thr His
465                 470                 475                 480
Phe Pro Gly Asn Leu Pro Asn Met Leu Arg Asp Leu Arg Asp Ala Phe
                485                 490                 495
Ser Arg Val Lys Thr Phe Phe Gln Met Lys Asp Gln Leu Asp Asn Leu
            500                 505                 510
Leu Leu Lys Glu Ser Leu Leu Glu Asp Phe Lys Gly Tyr Leu Gly Cys
            515                 520                 525
Gln Ala Leu Ser Glu Met Ile Gln Phe Tyr Leu Glu Glu Val Met Pro
            530                 535                 540
Gln Ala Glu Asn Gln Asp Pro Asp Ile Lys Ala His Val Asn Ser Leu
545                 550                 555                 560
Gly Glu Asn Leu Lys Thr Leu Arg Leu Arg Leu Arg Arg Cys His Arg
                565                 570                 575
Phe Leu Pro Cys Glu Asn Lys Ser Lys Ala Val Glu Gln Val Lys Asn
            580                 585                 590
```

```
Ala Phe Asn Lys Leu Gln Glu Lys Gly Ile Tyr Lys Ala Met Ser Glu
            595                 600                 605

Phe Asp Ile Phe Ile Asn Tyr Ile Glu Ala Tyr Met Thr Met Lys Ile
610                 615                 620

Arg Asn
625

<210> SEQ ID NO 57
<211> LENGTH: 626
<212> TYPE: PRT
<213> ORGANISM: artificial
<220> FEATURE:
<223> OTHER INFORMATION: Synthetic polypeptide

<400> SEQUENCE: 57

Gln Val Gln Leu Gln Gln Ser Gly Ala Val Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Ala Pro Gly Gln Gly Leu Glu Trp Ile
        35                  40                  45

Gly Ala Ile Tyr Pro Gly Asn Arg Asp Thr Asn Tyr Asn Gln Lys Phe
    50                  55                  60

Lys Gly Arg Ala Thr Leu Thr Thr Asp Thr Ser Ala Ser Thr Ala Tyr
65                  70                  75                  80

Met Glu Leu Ser Ser Leu Thr Ser Glu Asp Thr Ala Val Tyr Tyr Cys
                85                  90                  95

Thr Gly Ala Phe Ala Gly Tyr Tyr Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Leu Gly Gly Gly Ser Gly Gly Gly Ser Gly Gly
    450                 455                 460

Gly Gly Ser Pro Gly Gln Gly Thr Gln Ser Glu Asn Ser Cys Thr His
465                 470                 475                 480

Phe Pro Gly Asn Leu Pro Asn Met Leu Arg Asp Leu Arg Asp Ala Phe
                485                 490                 495

Ser Arg Val Lys Thr Phe Phe Gln Met Lys Asp Gln Leu Asp Asn Leu
            500                 505                 510

Leu Leu Lys Glu Ser Leu Leu Glu Asp Phe Lys Gly Tyr Leu Gly Cys
        515                 520                 525

Gln Ala Leu Ser Glu Met Ile Gln Phe Tyr Leu Glu Glu Val Met Pro
        530                 535                 540

Gln Ala Glu Asn Gln Asp Pro Asp Ile Lys Ala His Val Asn Ser Leu
545                 550                 555                 560

Gly Glu Asn Leu Lys Thr Leu Arg Leu Arg Leu Arg Arg Cys His Arg
                565                 570                 575

Phe Leu Pro Cys Glu Asn Lys Ser Lys Ala Val Glu Gln Val Lys Asn
            580                 585                 590

Ala Phe Asn Lys Leu Gln Glu Lys Gly Ile Tyr Lys Ala Met Ser Glu
        595                 600                 605

Phe Asp Ile Phe Ile Asn Tyr Ile Glu Ala Tyr Met Thr Met Lys Ile
        610                 615                 620

Arg Asn
625

<210> SEQ ID NO 58
<211> LENGTH: 453
<212> TYPE: PRT
<213> ORGANISM: artificial
<220> FEATURE:
<223> OTHER INFORMATION: Synthetic polypeptide

<400> SEQUENCE: 58

Glu Ile Gln Leu Gln Gln Ser Gly Ala Glu Leu Val Lys Pro Arg Ala
1               5                   10                  15

Ser Val Lys Ile Ser Cys Glu Ala Ser Gly Tyr Ser Phe Thr Gly Tyr
            20                  25                  30

Asn Met Asn Trp Val Lys Gln Ser Pro Gly Lys Ser Leu Glu Trp Ile
        35                  40                  45

```
Gly Asp Ile Asn Pro Tyr Tyr Gly Ala Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Ala Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 59
<211> LENGTH: 214
<212> TYPE: PRT
<213> ORGANISM: artificial
<220> FEATURE:
<223> OTHER INFORMATION: Synthetic polypeptide

<400> SEQUENCE: 59

```
Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 453
<212> TYPE: PRT
<213> ORGANISM: artificial
<220> FEATURE:
<223> OTHER INFORMATION: Synthetic polypeptide

<400> SEQUENCE: 60

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Lys Ser Leu Glu Trp Ile
        35                  40                  45

Gly Asp Ile Asn Pro Tyr Tyr Gly Ala Thr Thr Tyr Asn Gln Lys Phe
    50                  55                  60

Lys Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Arg Gly Asp Tyr Gly Asp Tyr Glu Gly Trp Tyr Phe Asp Val
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
435                 440                 445

Leu Ser Pro Gly Lys
    450

<210> SEQ ID NO 61
<211> LENGTH: 214
<212> TYPE: PRT
<213> ORGANISM: artificial
<220> FEATURE:
<223> OTHER INFORMATION: Synthetic polypeptide

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Asn Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 453
<212> TYPE: PRT
<213> ORGANISM: artificial
<220> FEATURE:
<223> OTHER INFORMATION: Synthetic polypeptide

<400> SEQUENCE: 62

Glu Ile Gln Leu Gln Gln Ser Gly Ala Glu Val Lys Lys Pro Gly Ala
1               5                   10                  15

Ser Val Lys Ile Ser Cys Glu Ala Ser Gly Tyr Ser Phe Thr Gly Tyr
            20                  25                  30

Asn Met Asn Trp Val Lys Gln Ala Pro Gly Lys Ser Leu Glu Trp Ile
        35                  40                  45

Gly Asp Ile Asn Pro Tyr Tyr Gly Ala Thr Thr Tyr Asn Gln Lys Phe
50                  55                  60

Lys Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Gly Asp Tyr Glu Gly Trp Tyr Phe Asp Val
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 63
<211> LENGTH: 214
<212> TYPE: PRT
<213> ORGANISM: artificial
<220> FEATURE:
<223> OTHER INFORMATION: Synthetic polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Asn Ala Pro Lys Leu Leu Ile
        35                  40                  45
```

```
Tyr Lys Ala Ser Asn Leu His Thr Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Gln Ser Tyr Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 64
<211> LENGTH: 451
<212> TYPE: PRT
<213> ORGANISM: artificial
<220> FEATURE:
<223> OTHER INFORMATION: Synthetic polypeptide

<400> SEQUENCE: 64

Asp Val Gln Leu Gln Gln Ser Gly Thr Val Leu Ala Arg Pro Gly Ala
 1               5                  10                  15

Ser Val Lys Met Ser Cys Lys Ala Ser Gly Tyr Thr Phe Thr Ser Tyr
                 20                  25                  30

Trp Ile His Trp Val Lys Gln Arg Pro Gly Gln Gly Leu Glu Trp Ile
             35                  40                  45

Gly Ala Ile Tyr Pro Gly Asn Arg Asp Thr Asn Tyr Asn Gln Lys Phe
         50                  55                  60

Lys Gly Lys Ala Lys Leu Thr Thr Val Thr Ser Ala Ser Thr Ala Tyr
 65                  70                  75                  80

Met Glu Leu Ser Ser Leu Thr Asn Glu Asp Ser Ala Val Tyr Tyr Cys
                 85                  90                  95

Thr Gly Ala Phe Ala Gly Tyr Tyr Asp Trp Tyr Phe Asp Val Trp Gly
            100                 105                 110

Ala Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 65
<211> LENGTH: 218
<212> TYPE: PRT
<213> ORGANISM: artificial
<220> FEATURE:
<223> OTHER INFORMATION: Synthetic polypeptide

<400> SEQUENCE: 65

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Gly Val Asp Tyr Ala
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asp Leu Asp Ser Gly Ile Pro Ala
    50                  55                  60

Arg Phe Ser Gly Ser Gly Ser Gly Thr Asn Phe Thr Leu Asn Ile His
65                  70                  75                  80

Pro Val Glu Glu Glu Asp Ala Ala Thr Tyr Tyr Cys Gln Gln Ser Tyr
                85                  90                  95
```

```
Glu Asp Pro Arg Thr Phe Gly Gly Gly Thr Leu Glu Ile Gln Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 66
<211> LENGTH: 451
<212> TYPE: PRT
<213> ORGANISM: artificial
<220> FEATURE:
<223> OTHER INFORMATION: Synthetic polypeptide

<400> SEQUENCE: 66

```
Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Ala Ile Tyr Pro Gly Asn Arg Asp Thr Asn Tyr Asn Gln Lys Phe
    50                  55                  60

Lys Gly Arg Val Thr Leu Thr Thr Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Gly Ala Phe Ala Gly Tyr Tyr Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 67
<211> LENGTH: 218
<212> TYPE: PRT
<213> ORGANISM: artificial
<220> FEATURE:
<223> OTHER INFORMATION: Synthetic polypeptide

<400> SEQUENCE: 67

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Gly Val Asp Tyr Ala
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asp Leu Asp Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Thr Tyr Tyr Cys Gln Gln Ser Tyr
                85                  90                  95

Glu Asp Pro Arg Thr Phe Gly Gly Gly Thr Thr Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
210                 215
```

<210> SEQ ID NO 68
<211> LENGTH: 451
<212> TYPE: PRT
<213> ORGANISM: artificial
<220> FEATURE:
<223> OTHER INFORMATION: Synthetic polypeptide

<400> SEQUENCE: 68

```
Gln Val Gln Leu Gln Gln Ser Gly Ala Val Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Ala Pro Gly Gln Gly Leu Glu Trp Ile
        35                  40                  45

Gly Ala Ile Tyr Pro Gly Asn Arg Asp Thr Asn Tyr Asn Gln Lys Phe
    50                  55                  60

Lys Gly Arg Ala Thr Leu Thr Thr Asp Thr Ser Ala Ser Thr Ala Tyr
65                  70                  75                  80

Met Glu Leu Ser Ser Leu Thr Ser Glu Asp Thr Ala Val Tyr Tyr Cys
                85                  90                  95

Thr Gly Ala Phe Ala Gly Tyr Tyr Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

-continued

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 69
<211> LENGTH: 218
<212> TYPE: PRT
<213> ORGANISM: artificial
<220> FEATURE:
<223> OTHER INFORMATION: Synthetic polypeptide

<400> SEQUENCE: 69

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Gly Val Asp Tyr Ala
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asp Leu Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Thr Tyr Tyr Cys Gln Gln Ser Tyr
                85                  90                  95

Glu Asp Pro Arg Thr Phe Gly Gly Gly Thr Thr Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 70
<211> LENGTH: 972
<212> TYPE: PRT
<213> ORGANISM: Homo sapiens

<400> SEQUENCE: 70

Met Gly Pro Gly Val Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala

-continued

```
                340                 345                 350
Asn Ala Thr Thr Lys Asp Thr Tyr Arg His Thr Phe Thr Leu Ser Leu
            355                 360                 365
Pro Arg Leu Lys Pro Ser Glu Ala Gly Arg Tyr Ser Phe Leu Ala Arg
            370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
            435                 440                 445
Val Trp Asp Asp Pro Tyr Pro Glu Val Leu Ser Gln Glu Pro Phe His
            450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
            485                 490                 495
Ala Phe Ile Pro Ile Ser Ala Gly Ala His Thr His Pro Pro Asp Glu
                500                 505                 510
Phe Leu Phe Thr Pro Val Val Ala Cys Met Ser Ile Met Ala Leu
            515                 520                 525
Leu Leu Leu Leu Leu Leu Leu Leu Tyr Lys Tyr Lys Gln Lys Pro
            530                 535                 540
Lys Tyr Gln Val Arg Trp Lys Ile Ile Glu Ser Tyr Glu Gly Asn Ser
545                 550                 555                 560
Tyr Thr Phe Ile Asp Pro Thr Gln Leu Pro Tyr Asn Glu Lys Trp Glu
                565                 570                 575
Phe Pro Arg Asn Asn Leu Gln Phe Gly Lys Thr Leu Gly Ala Gly Ala
            580                 585                 590
Phe Gly Lys Val Val Glu Ala Thr Ala Phe Gly Leu Gly Lys Glu Asp
            595                 600                 605
Ala Val Leu Lys Val Ala Val Lys Met Leu Lys Ser Thr Ala His Ala
            610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
                660                 665                 670
Asn Phe Leu Arg Arg Lys Ala Glu Ala Met Leu Gly Pro Ser Leu Ser
            675                 680                 685
Pro Gly Gln Asp Pro Glu Gly Gly Val Asp Tyr Lys Asn Ile His Leu
            690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
            740                 745                 750
Arg Asp Leu Leu His Phe Ser Ser Gln Val Ala Gln Gly Met Ala Phe
            755                 760                 765
```

-continued

Leu Ala Ser Lys Asn Cys Ile His Arg Asp Val Ala Ala Arg Asn Val
        770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 71
<211> LENGTH: 976
<212> TYPE: PRT
<213> ORGANISM: Macaca fascicularis

<400> SEQUENCE: 71

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
            20                  25                  30

Lys Pro Gly Glu Thr Val Thr Leu Arg Cys Val Gly Asn Gly Ser Val
        35                  40                  45

Glu Trp Asp Gly Pro Ile Ser Pro His Trp Thr Leu Tyr Ser Asp Gly
50                  55                  60

Pro Ser Ser Val Leu Thr Thr Asn Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Lys Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Leu Arg
    130                 135                 140

Gly Arg Pro Leu Leu Arg His Thr Asn Tyr Ser Phe Ser Pro Trp His
145                 150                 155                 160

Gly Phe Ile Ile His Arg Ala Lys Phe Ile Gln Gly Gln Asp Tyr Gln

```
            165                 170                 175
Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
            195                 200                 205

Pro Ala Glu Leu Val Arg Ile Arg Gly Glu Ala Ala Gln Ile Val Cys
210             215                 220

Ser Ala Ser Asn Ile Asp Val Asp Phe Asp Val Phe Leu Gln His Asn
225             230                 235                 240

Thr Thr Lys Leu Ala Ile Pro Gln Arg Ser Asp Phe His Asp Asn Arg
                245                 250                 255

Tyr Gln Lys Val Leu Thr Leu Ser Leu Gly Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asp Leu Ser
290                 295                 300

Ser Glu Gln Asn Leu Ile Gln Glu Val Thr Val Gly Glu Gly Leu Asn
305             310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ala Gly His Thr Asp Arg Cys Asp Glu Ala Gln Val Leu Gln
            435                 440                 445

Val Trp Val Asp Pro His Pro Glu Val Leu Ser Gln Glu Pro Phe Gln
            450                 455                 460

Lys Val Thr Val Gln Ser Leu Leu Thr Ala Glu Thr Leu Glu His Asn
465             470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala Arg Thr His Pro Pro Asp Glu
            500                 505                 510

Phe Leu Phe Thr Pro Val Val Ala Cys Met Ser Val Met Ala Leu
            515                 520                 525

Leu Leu Leu Leu Leu Leu Leu Leu Tyr Lys Tyr Lys Gln Lys Pro
            530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590
```

```
Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Ala Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Trp Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
            770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
            850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Leu Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Gly Ser Ser Ser Ser Ser Ser
930                 935                 940

Glu Pro Glu Glu Glu Ser Ser Ser Glu His Leu Ala Cys Cys Glu Gln
945                 950                 955                 960

Gly Asp Ile Ala Gln Pro Leu Leu Gln Pro Asn Asn Tyr Gln Phe Cys
                965                 970                 975

<210> SEQ ID NO 72
<211> LENGTH: 179
<212> TYPE: PRT
<213> ORGANISM: artificial
<220> FEATURE:
```

<223> OTHER INFORMATION: Synthetic polypeptide

<400> SEQUENCE: 72

```
His His His His His His His His Ser Gly Gly Gly Ser Gly Gly
1               5                   10                  15
Gly Ile Glu Gly Arg Glu Glu Val Ser Glu Tyr Cys Ser His Met Ile
            20                  25                  30
Gly Ser Gly His Leu Gln Ser Leu Gln Arg Leu Ile Asp Ser Gln Met
        35                  40                  45
Glu Thr Ser Cys Gln Ile Thr Phe Glu Phe Val Asp Gln Glu Gln Leu
    50                  55                  60
Lys Asp Pro Val Cys Tyr Leu Lys Lys Ala Phe Leu Leu Val Gln Asp
65                  70                  75                  80
Ile Met Glu Asp Thr Met Arg Phe Arg Asp Asn Thr Pro Asn Ala Ile
                85                  90                  95
Ala Ile Val Gln Leu Gln Glu Leu Ser Leu Arg Leu Lys Ser Cys Phe
            100                 105                 110
Thr Lys Asp Tyr Glu Glu His Asp Lys Ala Cys Val Arg Thr Phe Tyr
        115                 120                 125
Glu Thr Pro Leu Gln Leu Leu Glu Lys Val Lys Asn Val Phe Asn Glu
    130                 135                 140
Thr Lys Asn Leu Leu Asp Lys Asp Trp Asn Ile Phe Ser Lys Asn Cys
145                 150                 155                 160
Asn Asn Ser Phe Ala Glu Cys Ser Ser Gln Gly His Glu Arg Gln Ser
                165                 170                 175
Glu Gly Ser
```

<210> SEQ ID NO 73
<211> LENGTH: 406
<212> TYPE: PRT
<213> ORGANISM: artificial
<220> FEATURE:
<223> OTHER INFORMATION: Synthetic polypeptide

<400> SEQUENCE: 73

```
Ser Pro Gly Gln Gly Thr Gln Ser Glu Asn Ser Cys Thr His Phe Pro
1               5                   10                  15
Gly Asn Leu Pro Asn Met Leu Arg Asp Leu Arg Asp Ala Phe Ser Arg
            20                  25                  30
Val Lys Thr Phe Phe Gln Met Lys Asp Gln Leu Asp Asn Leu Leu Leu
        35                  40                  45
Lys Glu Ser Leu Leu Glu Asp Phe Lys Gly Tyr Leu Gly Cys Gln Ala
    50                  55                  60
Leu Ser Glu Met Ile Gln Phe Tyr Leu Glu Glu Val Met Pro Gln Ala
65                  70                  75                  80
Glu Asn Gln Asp Pro Asp Ile Lys Ala His Val Asn Ser Leu Gly Glu
                85                  90                  95
Asn Leu Lys Thr Leu Arg Leu Arg Leu Arg Arg Cys His Arg Phe Leu
            100                 105                 110
Pro Cys Glu Asn Lys Ser Lys Ala Val Glu Gln Val Lys Asn Ala Phe
        115                 120                 125
Asn Lys Leu Gln Glu Lys Gly Ile Tyr Lys Ala Met Ser Glu Phe Asp
    130                 135                 140
Ile Phe Ile Asn Tyr Ile Glu Ala Tyr Met Thr Met Lys Ile Arg Asn
145                 150                 155                 160
```

Gly Gly Gly Gly Ser Gly Gly Gly Ser Gly Gly Gly Ser Pro
            165             170             175

Lys Ser Cys Asp Lys Thr His Thr Cys Pro Pro Cys Pro Ala Pro Glu
        180                 185                 190

Leu Leu Gly Gly Pro Ser Val Phe Leu Phe Pro Pro Lys Pro Lys Asp
            195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
            245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Arg Glu
    290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
            325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
        355                 360                 365

Leu Thr Val Asp Lys Ser Arg Trp Gln Gln Gly Asn Val Phe Ser Cys
    370                 375                 380

Ser Val Met His Glu Ala Leu His Asn His Tyr Thr Gln Lys Ser Leu
385                 390                 395                 400

Ser Leu Ser Pro Gly Lys
            405

<210> SEQ ID NO 74
<211> LENGTH: 580
<212> TYPE: PRT
<213> ORGANISM: artificial
<220> FEATURE:
<223> OTHER INFORMATION: Synthetic polypeptide

<400> SEQUENCE: 74

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
            85                  90                  95

Asn Leu Lys Thr Leu Arg Leu Arg Leu Arg Arg Cys His Arg Phe Leu
        100                 105                 110

-continued

```
Pro Cys Glu Asn Lys Ser Lys Ala Val Glu Gln Val Lys Asn Ala Phe
            115                 120                 125
Asn Lys Leu Gln Glu Lys Gly Ile Tyr Lys Ala Met Ser Glu Phe Asp
        130                 135                 140
Ile Phe Ile Asn Tyr Ile Glu Ala Tyr Met Thr Met Lys Ile Arg Asn
145                 150                 155                 160
Gly Gly Gly Gly Ser Gly Gly Gly Ser Gly Gly Gly Gly Ser Pro
                165                 170                 175
Gly Gln Gly Thr Gln Ser Glu Asn Ser Cys Thr His Phe Pro Gly Asn
            180                 185                 190
Leu Pro Asn Met Leu Arg Asp Leu Arg Asp Ala Phe Ser Arg Val Lys
        195                 200                 205
Thr Phe Phe Gln Met Lys Asp Gln Leu Asp Asn Leu Leu Leu Lys Glu
    210                 215                 220
Ser Leu Leu Glu Asp Phe Lys Gly Tyr Leu Gly Cys Gln Ala Leu Ser
225                 230                 235                 240
Glu Met Ile Gln Phe Tyr Leu Glu Glu Val Met Pro Gln Ala Glu Asn
                245                 250                 255
Gln Asp Pro Asp Ile Lys Ala His Val Asn Ser Leu Gly Glu Asn Leu
            260                 265                 270
Lys Thr Leu Arg Leu Arg Leu Arg Arg Cys His Arg Phe Leu Pro Cys
        275                 280                 285
Glu Asn Lys Ser Lys Ala Val Glu Gln Val Lys Asn Ala Phe Asn Lys
    290                 295                 300
Leu Gln Glu Lys Gly Ile Tyr Lys Ala Met Ser Glu Phe Asp Ile Phe
305                 310                 315                 320
Ile Asn Tyr Ile Glu Ala Tyr Met Thr Met Lys Ile Arg Asn Gly Gly
                325                 330                 335
Gly Gly Ser Gly Gly Gly Ser Gly Gly Gly Ser Pro Lys Ser
            340                 345                 350
Cys Asp Lys Thr His Thr Cys Pro Pro Cys Pro Ala Pro Glu Leu Leu
        355                 360                 365
Gly Gly Pro Ser Val Phe Leu Phe Pro Pro Lys Pro Lys Asp Thr Leu
    370                 375                 380
Met Ile Ser Arg Thr Pro Glu Val Thr Cys Val Val Val Asp Val Ser
385                 390                 395                 400
His Glu Asp Pro Glu Val Lys Phe Asn Trp Tyr Val Asp Gly Val Glu
                405                 410                 415
Val His Asn Ala Lys Thr Lys Pro Arg Glu Glu Gln Tyr Asn Ser Thr
            420                 425                 430
Tyr Arg Val Val Ser Val Leu Thr Val Leu His Gln Asp Trp Leu Asn
        435                 440                 445
Gly Lys Glu Tyr Lys Cys Lys Val Ser Asn Lys Ala Leu Pro Ala Pro
    450                 455                 460
Ile Glu Lys Thr Ile Ser Lys Ala Lys Gly Gln Pro Arg Glu Pro Gln
465                 470                 475                 480
Val Tyr Thr Leu Pro Pro Ser Arg Asp Glu Leu Thr Lys Asn Gln Val
                485                 490                 495
Ser Leu Thr Cys Leu Val Lys Gly Phe Tyr Pro Ser Asp Ile Ala Val
            500                 505                 510
Glu Trp Glu Ser Asn Gly Gln Pro Glu Asn Asn Tyr Lys Thr Thr Pro
        515                 520                 525
Pro Val Leu Asp Ser Asp Gly Ser Phe Phe Leu Tyr Ser Lys Leu Thr
```

```
                530                 535                 540
Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 75
<211> LENGTH: 160
<212> TYPE: PRT
<213> ORGANISM: Homo sapiens

<400> SEQUENCE: 75

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 76
<211> LENGTH: 42
<212> TYPE: DNA
<213> ORGANISM: artificial
<220> FEATURE:
<223> OTHER INFORMATION: Synthetic polynucleotide

<400> SEQUENCE: 76
gattacgcca agcttataga cagatggggg tgtcgttttg gc                     42

<210> SEQ ID NO 77
<211> LENGTH: 36
<212> TYPE: DNA
<213> ORGANISM: artificial
<220> FEATURE:
<223> OTHER INFORMATION: Synthetic polynucleotide

<400> SEQUENCE: 77
gattacgcca agcttggata cagttggtgc agcatc                            36

<210> SEQ ID NO 78
<211> LENGTH: 14
<212> TYPE: PRT
<213> ORGANISM: Artificial
<220> FEATURE:
```

<223> OTHER INFORMATION: Synthetic polypeptide

<400> SEQUENCE: 78

Gly Gly Gly Gly Ser Gly Gly Gly Gly Ser Gly Gly Gly Gly
1               5                   10